United States Patent
Pan et al.

(10) Patent No.: US 9,496,504 B2
(45) Date of Patent: Nov. 15, 2016

(54) MATERIALS FOR ORGANIC ELECTROLUMINESCENT DEVICES

(75) Inventors: Junyou Pan, Frankfurt Am Main (DE); Herwig Buchholz, Frankfurt Am Main (DE); Teresa Mujica-Fernaud, Darmstadt (DE); Irina Martynova, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 154 days.

(21) Appl. No.: 13/521,266

(22) PCT Filed: Dec. 17, 2010

(86) PCT No.: PCT/EP2010/007744
§ 371 (c)(1),
(2), (4) Date: Aug. 23, 2012

(87) PCT Pub. No.: WO2011/085781
PCT Pub. Date: Jul. 21, 2011

(65) Prior Publication Data
US 2012/0305851 A1    Dec. 6, 2012

(30) Foreign Application Priority Data
Jan. 16, 2010 (DE) .......................... 10 2010 004 803

(51) Int. Cl.
| | |
|---|---|
| H01L 51/50 | (2006.01) |
| H01L 51/00 | (2006.01) |
| C07D 209/86 | (2006.01) |
| C07D 251/22 | (2006.01) |
| C09B 11/04 | (2006.01) |
| C09B 57/00 | (2006.01) |
| C09B 57/10 | (2006.01) |

(Continued)

(52) U.S. Cl.
CPC .......... *H01L 51/0061* (2013.01); *C07D 209/86* (2013.01); *C07D 251/22* (2013.01); *C09B 11/04* (2013.01); *C09B 57/00* (2013.01); *C09B 57/007* (2013.01); *C09B 57/008* (2013.01); *C09B 57/10* (2013.01); *C09B 69/109* (2013.01); *H01L 51/0059* (2013.01); *H01L 51/0508* (2013.01); *H01L 51/42* (2013.01); *H01L 51/5012* (2013.01); *H01L 51/5048* (2013.01); *H01L 51/5096* (2013.01); *Y02E 10/549* (2013.01)

(58) Field of Classification Search
None
See application file for complete search history.

(56) References Cited

U.S. PATENT DOCUMENTS

2008/0036373 A1    2/2008  Itoh et al.
2009/0256468 A1*  10/2009  Kim et al. .................... 313/504

(Continued)

FOREIGN PATENT DOCUMENTS

| EP | 2080762 A1 | 7/2009 | |
|---|---|---|---|
| EP | 2141152 * | 1/2010 | ............ C09K 11/06 |

(Continued)

OTHER PUBLICATIONS

International Search Report for PCT/EP2010/007744 mailed Jun. 8, 2011.

(Continued)

*Primary Examiner* — Gregory Clark
(74) *Attorney, Agent, or Firm* — Drinker Biddle & Reath LLP

(57) ABSTRACT

The present invention relates to compounds of the formula (1) which are suitable for use in electronic devices, in particular organic electroluminescent devices, and to electronic devices which contain these compounds.

21 Claims, 1 Drawing Sheet

(51) Int. Cl.
*C09B 69/10* (2006.01)
*H01L 51/05* (2006.01)
*H01L 51/42* (2006.01)

(56) References Cited

U.S. PATENT DOCUMENTS

2010/0044695 A1 2/2010 Kai et al.
2010/0155712 A1* 6/2010 Kitamura ................ 257/40

FOREIGN PATENT DOCUMENTS

| EP | 2141152 A1 | 1/2010 |
|---|---|---|
| JP | 2008-037848 A | 2/2008 |
| JP | 2008-110946 A | 5/2008 |
| WO | WO-2008/056746 A1 | 5/2008 |
| WO | WO-2008/117826 A1 | 10/2008 |
| WO | WO-2008/123189 A1 | 10/2008 |

OTHER PUBLICATIONS

Schnabel et al., "The Synthesis of Substituted Melams", The Journal of Organic Chemistry, vol. 27, pp. 2514-2519 (1962).

Japanese Office Action from corresponding Japanese Patent Application No. 2012-548348 dated Oct. 28, 2014.

* cited by examiner

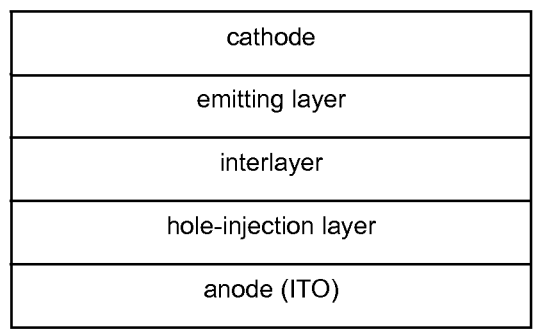

MATERIALS FOR ORGANIC ELECTROLUMINESCENT DEVICES

RELATED APPLICATIONS

This application is a national stage application (under 35 U.S.C. §371) of PCT/EP2010/007744, filed Dec. 17, 2010, which claims benefit of German Patent Application No. 10 2010 004 803.8, filed Jan. 16, 2010.

The present invention relates to materials for use in electronic devices, in particular in organic electroluminescent devices, and to electronic devices containing these materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., Appl. Phys. Lett. 1999, 75, 4-6). For quantum-mechanical reasons, an up to four-fold energy and power efficiency is possible using organometallic compounds as phosphorescence emitters. In general, however, there is still a need for improvement in OLEDs, in particular also in OLEDs which exhibit triplet emission (phosphorescence), for example with respect to efficiency, operating voltage and in particular lifetime. This applies, in particular, to OLEDs which emit in the relatively short-wave range, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in these materials for fluorescent OLEDs.

In accordance with the prior art, ketones (for example in accordance with WO 2004/093207 or in accordance with the unpublished application DE 102008033943.1) or phosphine oxides (for example in accordance with WO 05/003253), inter alia, are used as matrix materials for phosphorescent emitters. Furthermore, triazine derivatives are used as matrix materials for phosphorescent emitters (for example in accordance with WO 2007/063754 or WO 2008/056746). However, there is still a need for improvement, in particular with respect to the efficiency and lifetime of the device, on use of these matrix materials as in the case of other matrix materials.

The object of the present invention is the provision of compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, it is the object of the present invention to provide matrix materials which are also suitable for green- and blue-phosphorescent OLEDs. The object of the present invention is furthermore to provide matrix materials for phosphorescent emitters which have a small separation between the $S_1$ level and the $T_1$ level, since compounds of this type are particularly suitable for use as triplet matrix material.

Surprisingly, it has been found that certain compounds described in greater detail below achieve this object and result in significant improvements in the organic electroluminescent device, in particular with respect to the lifetime, the efficiency and the operating voltage. This applies to red-, green- and blue-phosphorescent electroluminescent devices, in particular on use of the compounds according to the invention as matrix material. The present invention therefore relates to these materials and to organic electroluminescent devices which contain compounds of this type.

The present invention therefore relates to a compound of the following formula (1),

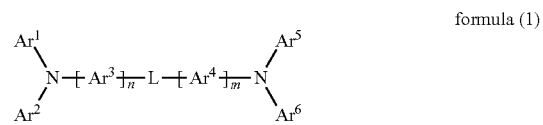

formula (1)

where the following applies to the symbols and indices used:

$Ar^1$, $Ar^2$ is on each occurrence, identically or differently, an aromatic or heteroaromatic ring system having 5 to 60 aromatic ring atoms, which may be substituted by one or more radicals R; $Ar^1$ and $Ar^2$ here may also be connected to one another by a single bond and thus form a carbazole;

$Ar^3$, $Ar^4$ is on each occurrence, identically or differently, a divalent aromatic or heteroaromatic ring system having 5 to 30 aromatic ring atoms, which may be substituted by one or more radicals R, with the proviso that $Ar^3$ and $Ar^4$ do not contain any aryl groups having more than two aromatic six-membered rings condensed directly onto one another;

$Ar^5$, $Ar^6$ stands, identically or differently on each occurrence, for a group of the following formula (2), where the dashed bond indicates the position of the link to N;

formula (2)

X is on each occurrence, identically or differently, CR or N, with the proviso that at least two groups X in $Ar^5$ stand for N, and with the proviso that in each case a maximum of three symbols X in the group of the formula (2) stand for N; and furthermore with the proviso that, if the formula (2) stands for a triazine, the radicals R are not equal to an alkoxy group, a thioalkoxy group, chlorine or a substituted or unsubstituted amino group;

L is a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which may be substituted by in each case one or more radicals R, where one or more $CH_2$ groups, which are preferably not adjacent, may be replaced by $Si(R)_2$, $Ge(R)_2$, $Sn(R)_2$, C=O, C=S, C=Se, C=NR, P(=O)R, S=O, $SO_2$, —O—, —S— or —CONR— and where one or more H atoms may be replaced by D, F, Cl, Br, I, CN or $NO_2$, or a divalent aromatic or heteroaromatic ring system having 5 to 30 aromatic ring atoms, which may be substituted by one or more radicals R, where L does not contain any aryl groups having more than two aromatic six-membered rings condensed directly onto one another, or L is $Si(R)_2$, $Ge(R)_2$, O, S, C(=O), S(=O), $SO_2$, $SF_4$, PR, P(=O)(R), $PF_3$, P(=S)(R), AsR, As(=O)(R), As(=S)(R), Sb, Sb(=O)(R), Sb(=S)(R), N(Ar), or L is a combination of two, three, four or five of the above-mentioned systems;

R is selected on each occurrence, identically or differently, from the group consisting of H, D, F, Cl, Br, I, CN, $NO_2$, $N(Ar)_2$, $N(R^1)_2$, $C(=O)Ar$, $C(=O)R^1$, $P(=O)(Ar)_2$, $B(R^1)_2$, $B(OR^1)_2$, $Si(R^1)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^1$, an aryloxy or heteroaryloxy group having 5 to 60 aromatic ring atoms, which may be substituted by one or more radicals $R^1$, or an aralkyl or heteroaralkyl group having 5 to 60 aromatic ring atoms, which may in each case be substituted by one or more radicals $R^1$, where two or more adjacent substituents R may optionally form a mono- or polycyclic, aliphatic, aromatic or heteroaromatic ring system, which may be substituted by one or more radicals $R^1$;

$R^1$ is selected on each occurrence, identically or differently, from the group consisting of H, D, F, Cl, Br, I, CN, $NO_2$, $N(Ar)_2$, $N(R^2)_2$, $C(=O)Ar$, $C(=O)R^2$, $P(=O)(Ar)_2$, $B(R^2)_2$, $B(OR^2)_2$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may be substituted by one or more radicals $R^2$, where two or more adjacent substituents $R^1$ may optionally form a mono- or polycyclic, aliphatic, aromatic or heteroaromatic ring system, which may be substituted by one or more radicals $R^2$;

Ar is on each occurrence, identically or differently, an aromatic or heteroaromatic ring system having 5-30 aromatic ring atoms, which may be substituted by one or more non-aromatic radicals $R^2$; two radicals Ar which are bonded to the same N atom or P atom may also be bridged to one another by a single bond or a bridge selected from $N(R^2)$, $C(R^2)_2$, O or S;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

m, n is on each occurrence, identically or differently, 0 or 1, where m=n=1 if L stands for O, S or N(Ar).

A BRIEF DESCRIPTION OF THE FIGURES

FIG. 1 illustrates OLED1 to OLED4 having a structure in accordance with the prior art.

A DETAILED DESCRIPTION OF THE INVENTION

An aryl group in the sense of this invention contains 6 to 60 C atoms; a heteroaryl group in the sense of this invention contains 1 to 59 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl or bipyridine, are, by contrast, not referred to as an aryl or heteroaryl group, but instead as an aromatic or heteroaromatic ring system.

An aromatic ring system in the sense of this invention contains 6 to 60 C atoms in the ring system. A heteroaromatic ring system in the sense of this invention contains 1 to 59 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is also intended to be taken to mean, in particular, a system in which, in addition, a plurality of aryl and/or heteroaryl groups are linked to one another directly or via a carbon atom. Thus, for example, systems such as biphenyl, terphenyl, fluorene, indenofluorene, 9,9'-spirobifluorene, 9,9-diarylfluorene, etc., in particular, are also intended to be taken to be aromatic ring systems in the sense of this invention.

For the purposes of the present invention, an aromatic or heteroaromatic ring system which has not more than two six-membered rings condensed directly onto one another is taken to mean an aromatic ring system which either contains only non-condensed aryl or heteroaryl groups, such as, for example, phenyl or pyridine, or which contains aryl or heteroaryl groups having precisely two aromatic six-membered rings condensed directly onto one another, such as, for example, naphthalene or quinoline, or which, if it contains relatively large condensed aryl- or heteroaryl groups, then only contains those in which not only six-membered aromatic rings, but also five-membered aromatic rings, are condensed on and in which not more than two six-membered rings are condensed directly onto one another. Thus, for example, anthracene, phenanthrene, pyrene, perylene, etc. are excluded from the definition of $Ar^3$, $Ar^4$ and L, since three, four or five aromatic six-membered rings therein are condensed directly onto one another; by contrast, fluorene, spirobifluorene, indenofluorene, carbazole, indenocarbazole or indolocarbazole, for example, are encompassed by the definition of $Ar^3$, $Ar^4$ and L, since in no aromatic six-membered rings in these groups are condensed directly onto one another, but instead only saturated (aliphatic) five-membered rings or heteroaromatic five-membered rings. This restriction regarding the condensed six-membered aryl groups is due to the fact that the triplet energy in systems having more than two six-membered rings condensed directly onto one another is significantly lower, meaning that such materials are not very suitable as matrix material for triplet emitters.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl and octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, benzphenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or transindenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the invention, $Ar^1$ and $Ar^2$ are not connected via a single bond and thus preferably, together with the nitrogen to which they are bonded, do not represent a carbazole or carbazole derivative.

Preferred embodiments of the group of the formula (2) are, for $Ar^5$, selected from the group consisting of 1,3,5-triazine, 1,2,4-triazine, pyrazine, pyrimidine and pyridazine and, for $Ar^6$, from the group consisting of 1,3,5-triazine, 1,2,4-triazine, pyrazine, pyrimidine, pyridazine, pyridine, and phenyl, where these groups may in each case be substituted by one or more radicals R. The radical R here is as defined above and, if $Ar^5$ stands for a triazine, does not represent an alkoxy group, thioalkoxy group, chlorine or substituted or unsubstituted amino group.

In a preferred embodiment of the invention, the group $Ar^6$ contains at least one nitrogen in the ring.

In a particularly preferred embodiment of the invention, two or three groups X in each group of the formula (2) stand, identically or differently on each occurrence, for N, and the remaining groups X stand for CR.

Preferred embodiments of the groups of the formula (2) which stand for $Ar^5$ are therefore, identically or differently on each occurrence, the groups of the following formulae (3) to (11),

formula (3)

formula (4)

formula (5)

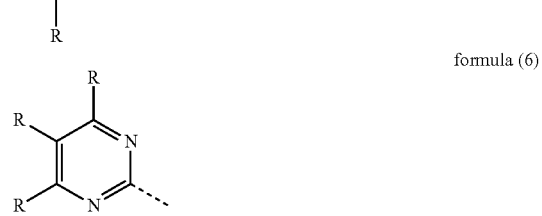

formula (6)

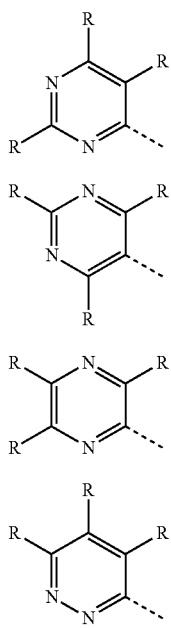

formula (7)

formula (8)

formula (9)

formula (10)

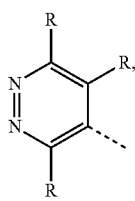

formula (11)

where the symbols used have the meanings given above; the dashed bond here indicates the position of the bond from the group to the nitrogen.

Preferred groups $Ar^6$, apart from the groups of the formulae (3) to (11) shown above, are the groups of the following formulae (12) to (15),

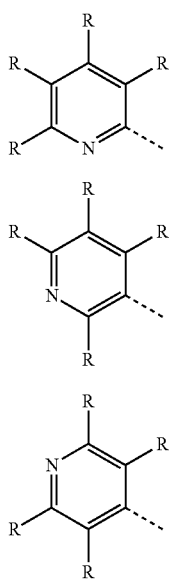

formula (12)

formula (13)

formula (14)

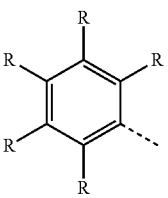

formula (15)

where the symbols used have the meanings given above; the dashed bond here indicates the position of the bond from the group to the nitrogen.

The groups $Ar^5$ of the above-mentioned formulae (3) to (11) can be combined with one another as desired with the groups $Ar^6$ of the above-mentioned formulae (3) to (15). The groups of the formulae (3), (6), (7) and (8) are particularly preferred.

Preferred groups —$NAr^5Ar^6$ in compounds of the formula (1) are the groups of the following formulae (16) to (27):

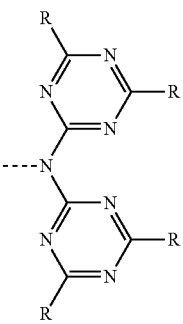

formula (16)

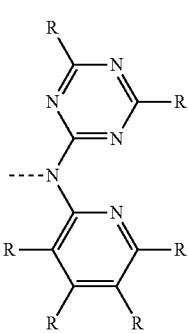

formula (17)

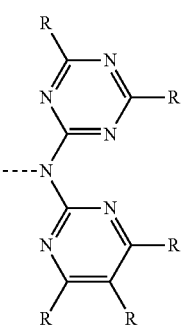

formula (18)

formula (19)
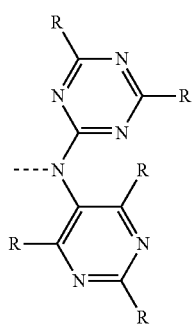

formula (20)
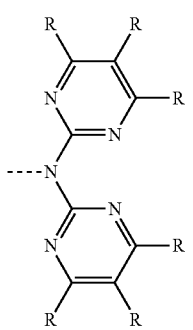

formula (21)
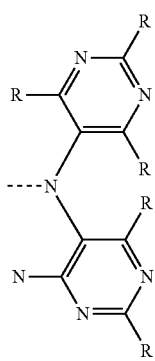

formula (22)
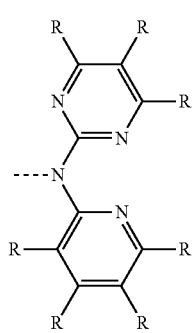

formula (23)
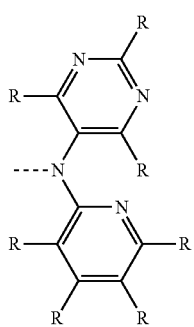

formula (24)
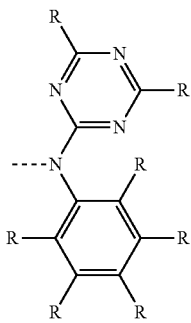

formula (25)
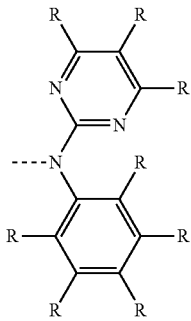

formula (26)
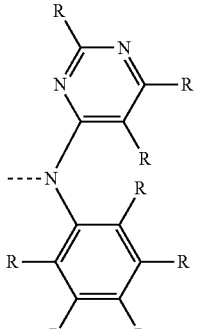

formula (27)
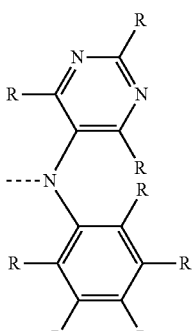

where the symbols used have the meanings given above, and the dashed bond indicates the bond from this group to L or $Ar^4$.

In a preferred embodiment of the invention, $Ar^1$ and $Ar^2$ stand, identically or differently on each occurrence, for an aromatic or heteroaromatic ring system having 5 to 30 aromatic ring atoms, particularly preferably having 5 to 24 aromatic ring atoms, in particular for an aromatic ring system, which may in each case also be substituted by one or more radicals R. The aromatic or heteroaromatic ring system here preferably contains not more than three, in particular not more than two, aromatic six-membered rings condensed directly onto one another. The groups $Ar^1$ and $Ar^2$ are preferably selected, identically or differently on each occurrence, from the following formulae (28) to (42),
formula (28)
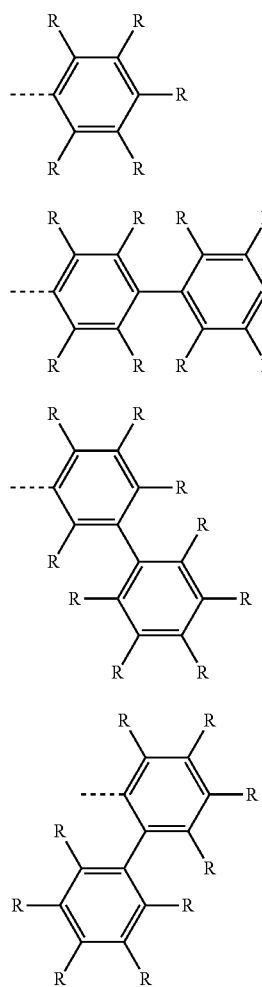
formula (29)
formula (30)
formula (31)
formula (32)
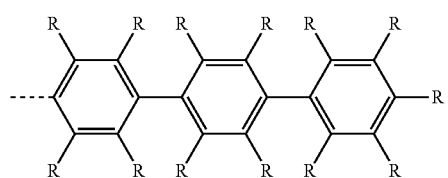
formula (33)
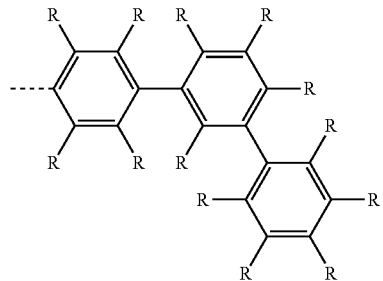
formula (34)
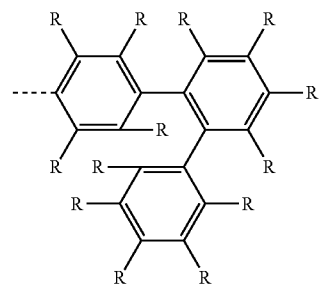
formula (35)
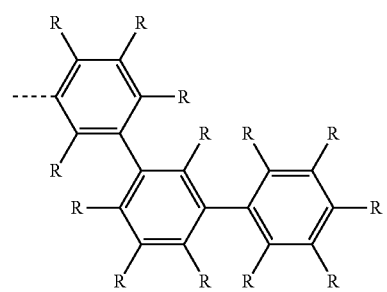
formula (36)
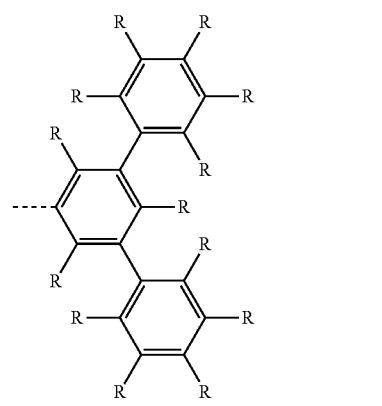
formula (37)
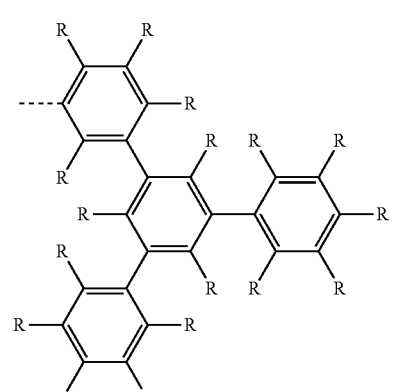
formula (38)
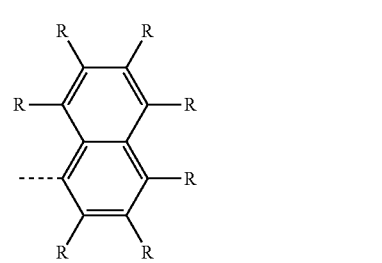

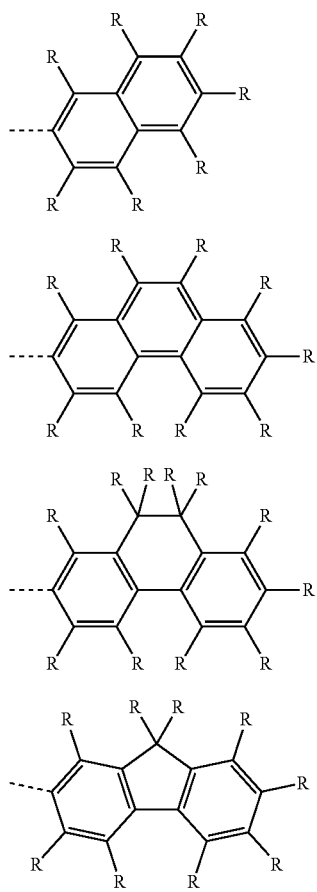

formula (39)

formula (40)

formula (41)

formula (42)

where the symbols used have the meanings given above, and the dashed bond indicates the bond from this group to the nitrogen.

The above-mentioned formulae (28) to (42) can be combined with one another as desired. The groups of the formulae (28), (29), (30), (33), (35), (36), (37) and (42) are particularly preferred.

In a preferred embodiment of the invention, at least one group $Ar^1$ or $Ar^2$ is a phenyl group or a meta- or para-biphenyl group, which may be substituted by one or more radicals R, i.e. a group of the above-mentioned formulae (28), (29) or (30).

Examples of preferred groups —$NAr^1Ar^2$ in compounds of the formula (1) are the groups of the following formulae (43) to (50):

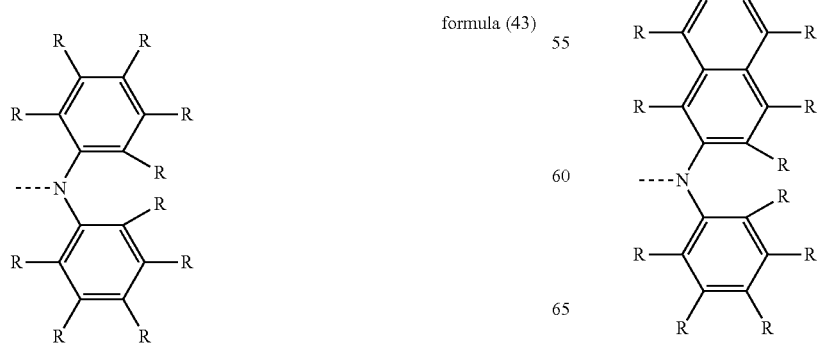

formula (43)

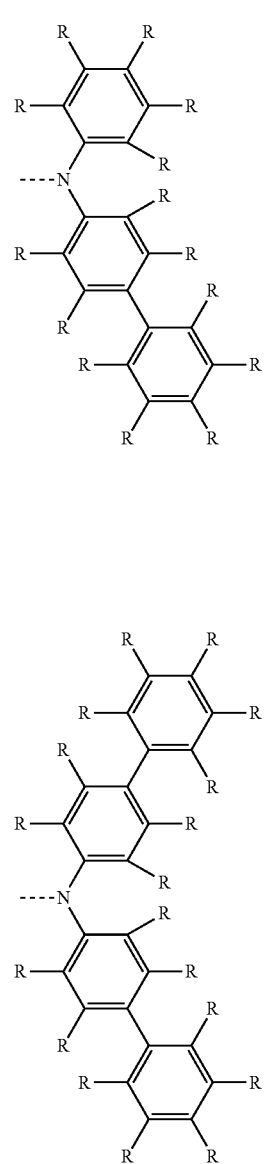

formula (44)

(formula 45)

formula (46)

-continued formula (47)

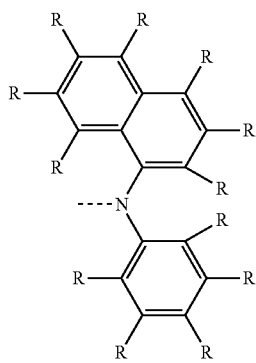

formula (48)

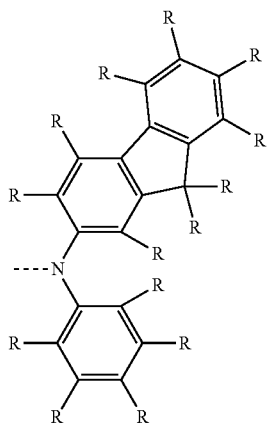

formula (49)

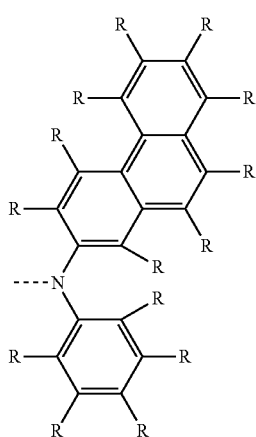

formula (50)

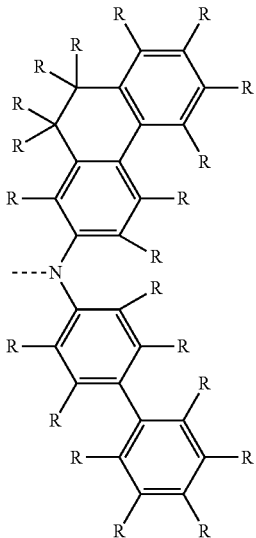

where the symbols used have the meanings given above, and the dashed bond indicates the bond from this group to $Ar^3$ or to L.

In a further preferred embodiment of the invention, if L is linked directly to one or both nitrogen atoms, i.e. if n=0 and/or m=0, L is a divalent straight-chain alkylene or alkylidene group having 1 to 10 C atoms, in particular 1 to 5 C atoms, or a branched or cyclic alkylene or alkylidene group having 3 to 10 C atoms, in particular 3 to 6 C atoms, which may be substituted by in each case one or more radicals R, where one or more $CH_2$ groups which are preferably not bonded directly to N and are preferably not adjacent may be replaced by $Si(R)_2$, C=O, P(=O)R, S=O, $SO_2$, —O—, —S— or —CONR— and where one or more H atoms may be replaced by D or F, or a divalent aromatic or heteroaromatic ring system having 5 to 24 aromatic ring atoms, which may also be substituted by one or more radicals R, or $Si(R)_2$, C(=O), S(=O), $SO_2$, P(=O)R or a combination of two or three of these systems. If L is not bonded directly to N, i.e. if m=n=1, L is, apart from the preferred embodiments mentioned above, preferably selected from O, S or N(Ar). L here, as defined above, does not contain any aryl groups having more than two aromatic six-membered rings condensed directly onto one another. L also preferably contains no naphthyl groups or other aryl groups having two aromatic six-membered rings condensed directly onto one another.

In a particularly preferred embodiment of the invention, L is, if L is linked directly to one or both nitrogen atoms, i.e. if n=0 and/or m=0, a divalent aromatic or heteroaromatic ring system having 6 to 24 aromatic ring atoms, which may be substituted by one or more radicals R, or $Si(R)_2$ or C(=O). If L is not bonded directly to N, i.e. if m=n=1, L is, apart from the particularly preferred embodiments mentioned above, particularly preferably selected from O, S or N(Ar).

If L stands for an aromatic or heteroaromatic ring system, L is then preferably selected from structures of the following formulae (51) to (144),

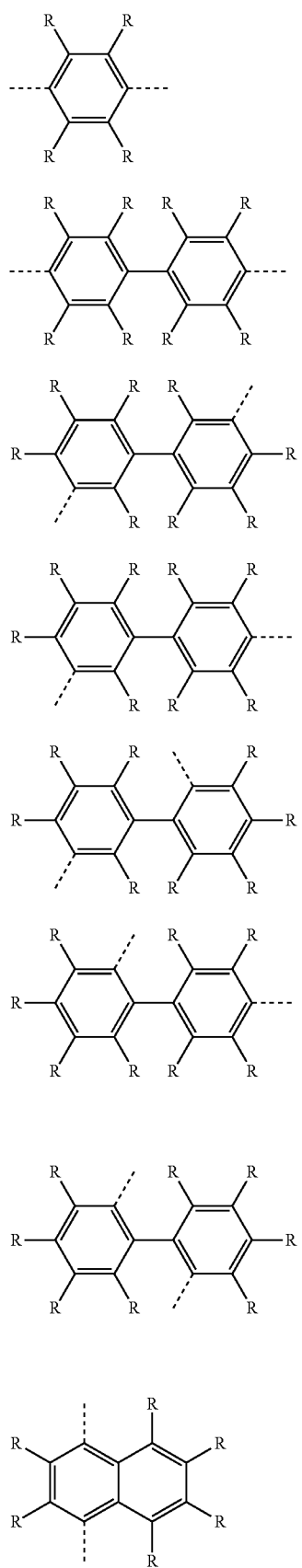
formula (51)
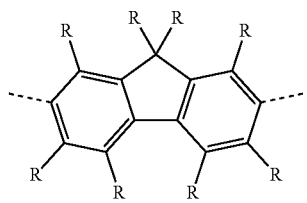
formula (52)
formula (53)
formula (54)
formula (55)
formula (56)
formula (57)
formula (58)
formula (59)
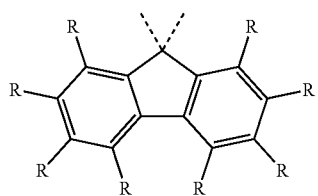
formula (60)
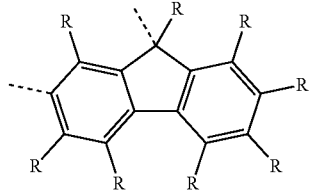
formula (61)
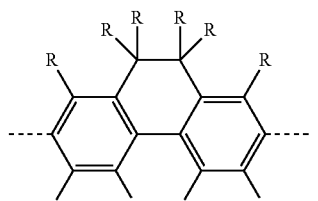
formula (62)
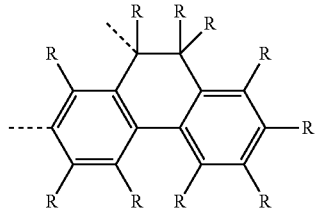
formula (63)
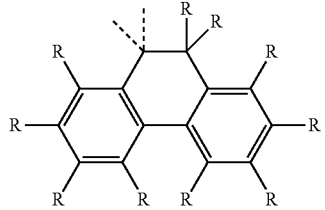
formula (64)
formula (65)
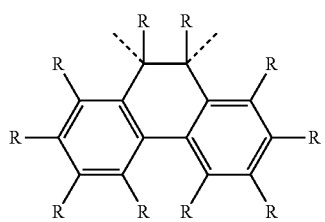

-continued
formula (66)
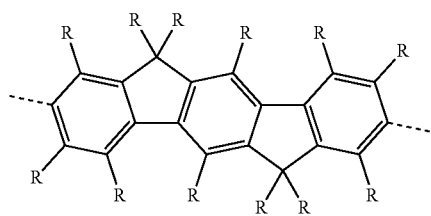
formula (67)
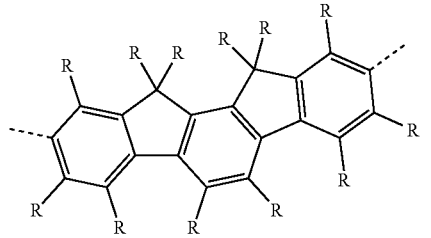
formula (68)
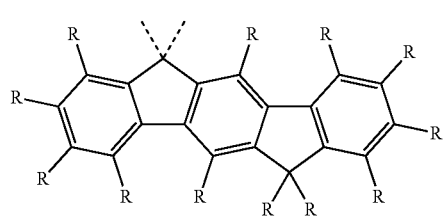
formula (69)
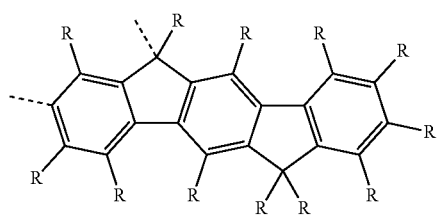
formula (70)
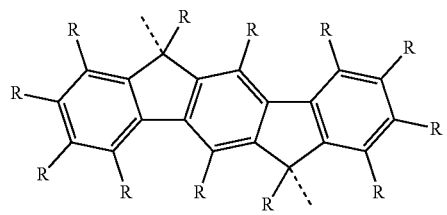
formula (71)
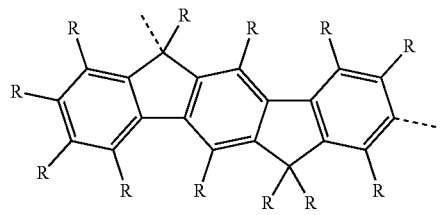
formula (72)
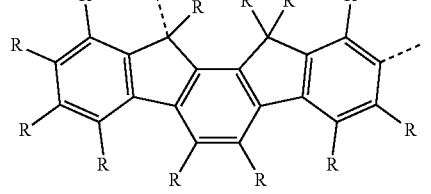
formula (73)
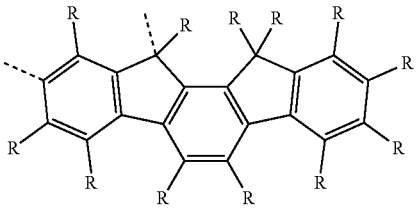
formula (74)
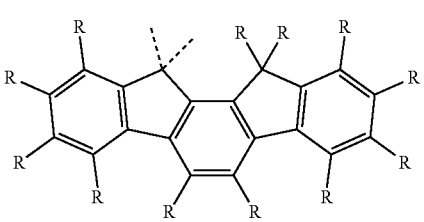
formula (75)
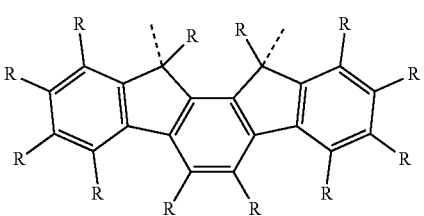
formula (76)
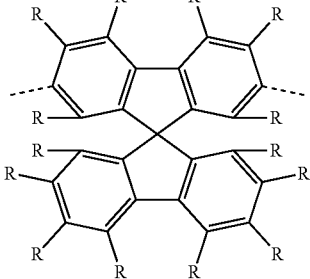
formula (77)
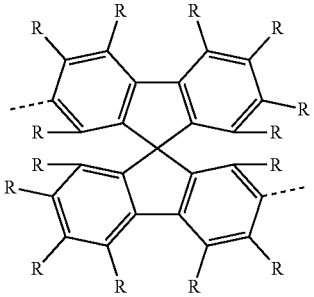
formula (78)
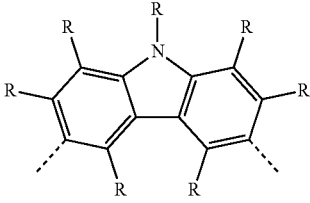

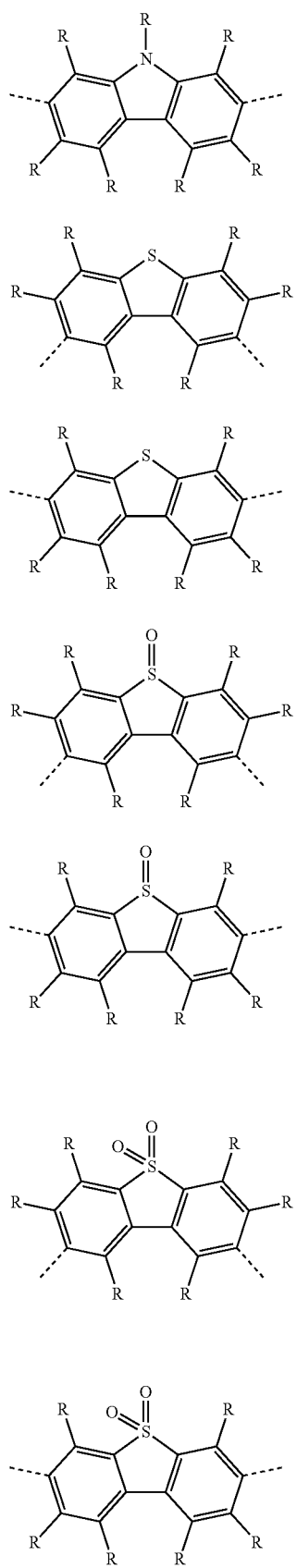
formula (79)
formula (80)
formula (81)
formula (82)
formula (83)
formula (84)
formula (85)
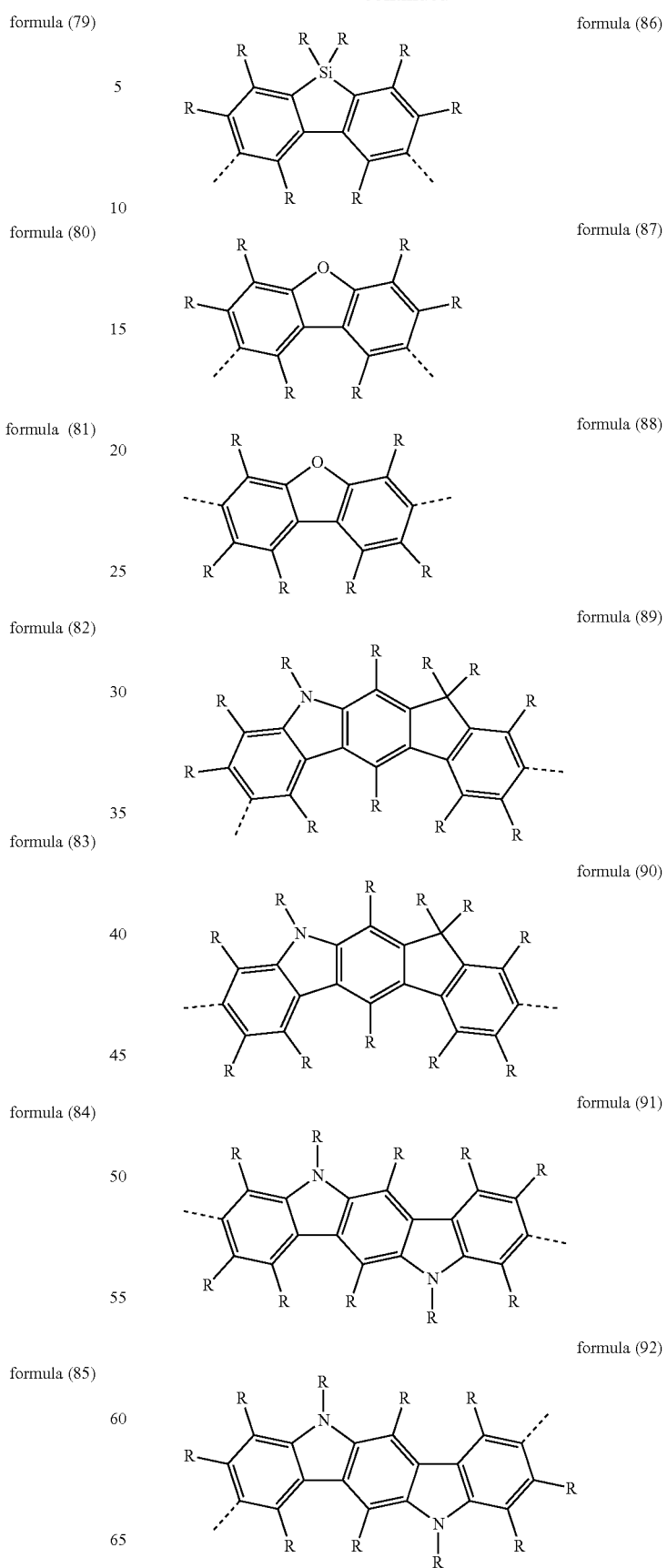
formula (86)
formula (87)
formula (88)
formula (89)
formula (90)
formula (91)
formula (92)

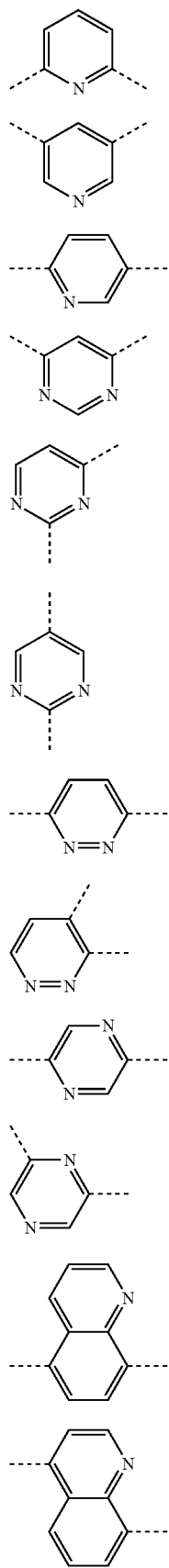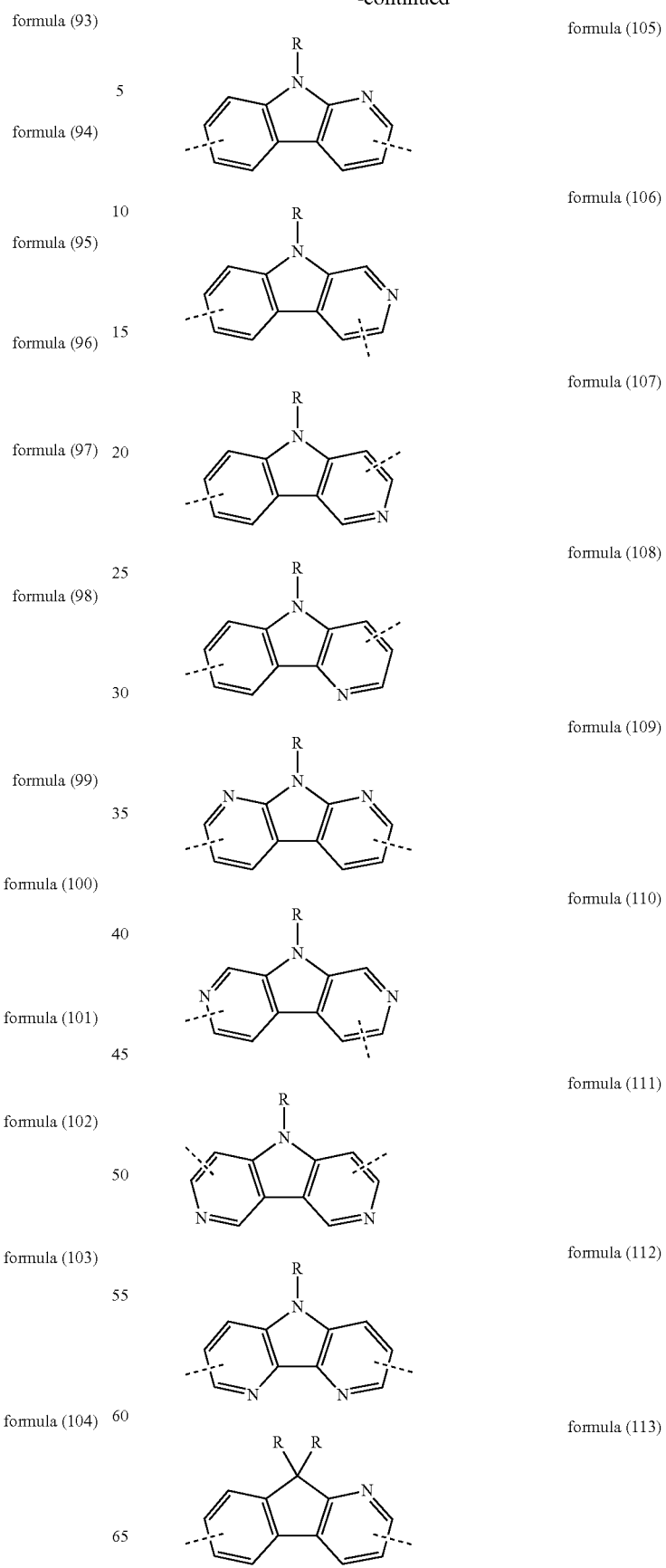

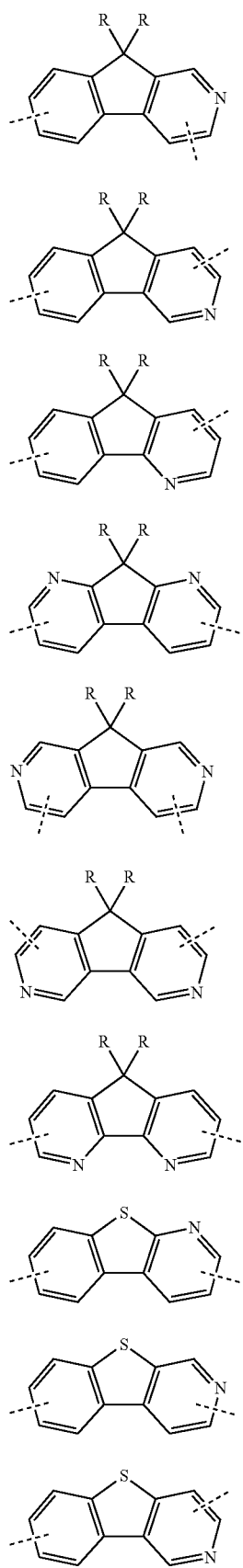
formula (114)
formula (115)
formula (116)
formula (117)
formula (118)
formula (119)
formula (120)
formula (121)
formula (122)
formula (123)
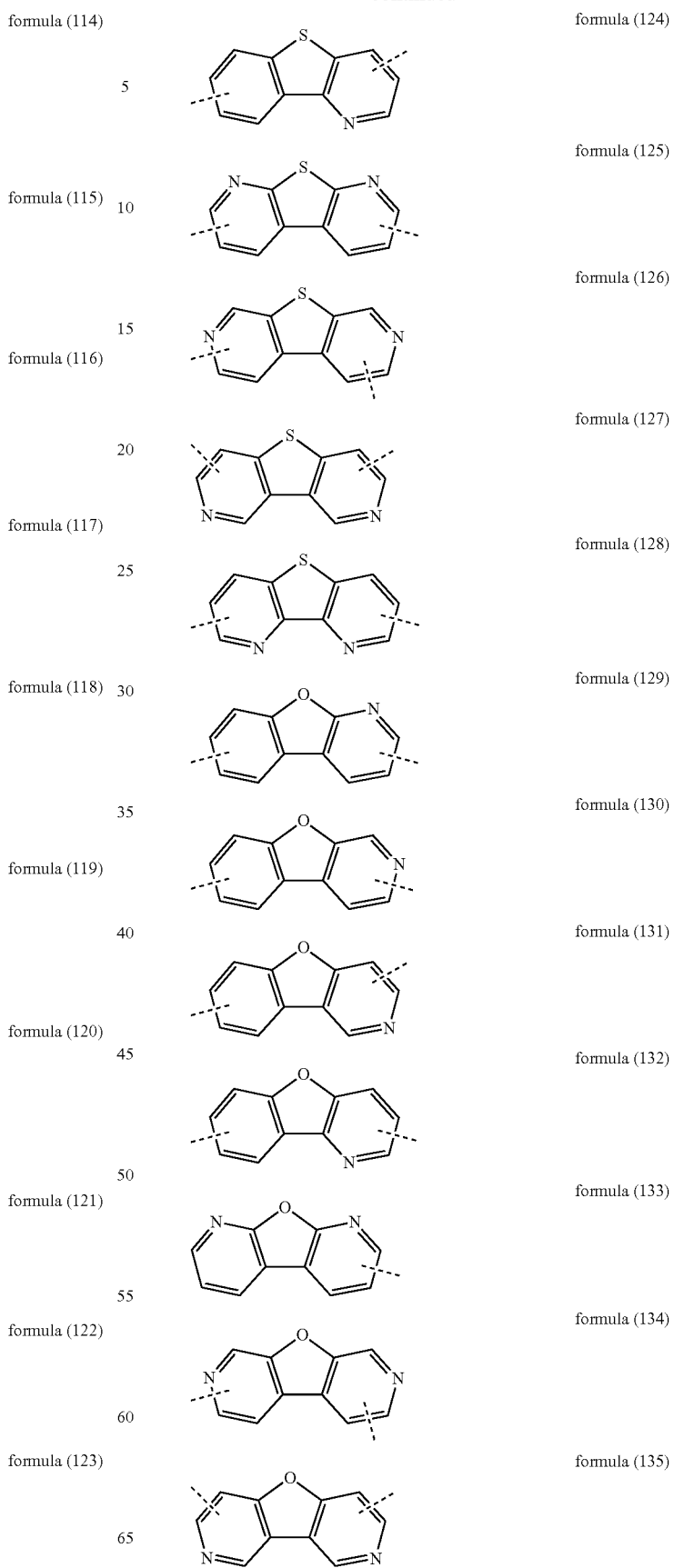
formula (124)
formula (125)
formula (126)
formula (127)
formula (128)
formula (129)
formula (130)
formula (131)
formula (132)
formula (133)
formula (134)
formula (135)

-continued formula (136)
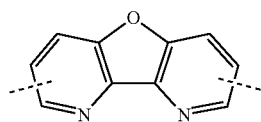

formula (137)
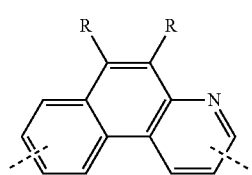

formula (138)
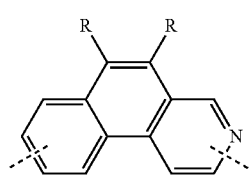

formula (139)
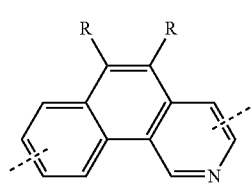

formula (140)
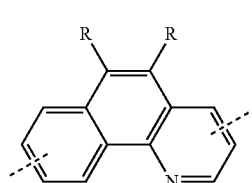

formula (141)
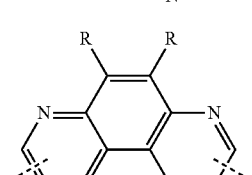

formula (142)
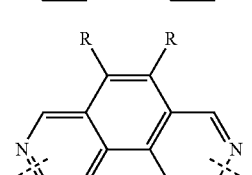

formula (143)
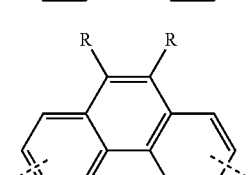

formula (144)
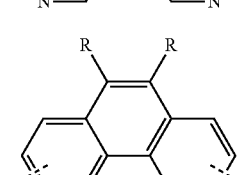

where the symbols used have the meanings given above, and the dashed bonds indicate the bonds to N or Ar$^3$ or Ar$^4$. If a precise position of the bond is not indicated, this means that the bond can be in any desired position.

In a further preferred embodiment of the invention, Ar$^3$ and Ar$^4$ are selected, identically or differently on each occurrence, from structures of the above-mentioned formulae (51) to (144).

In a further preferred embodiment of the invention, the indices m and n=1, i.e. the bridging unit has the structure —Ar$^3$-L-Ar$^4$—. The bridging unit L here preferably has a structure of the following formula (145):

$$—(CR_2)_p—(Y)_q—\qquad\text{formula (145)}$$

where R has the meaning given above, and furthermore:

Y is, identically or differently on each occurrence, CR$_2$, SiR$_2$, GeR$_2$, S, O or NR;

p is a number from 0 to 14, preferably 0, 1, 2, 3, 4, 5 or 6;

q is 0, 1, 2, 3 or 4, preferably 0, 1 or 2;

p+q>0;

with the proviso that a plurality of heteroatoms are not bonded directly to one another.

Examples of preferred groups Ar$^3$-L-Ar$^4$ are the following groups:

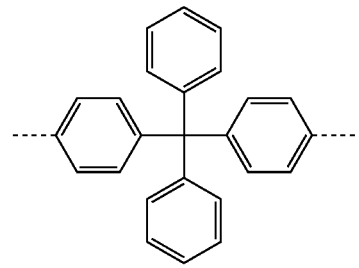

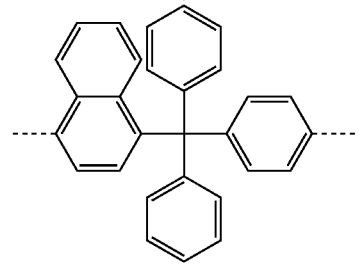

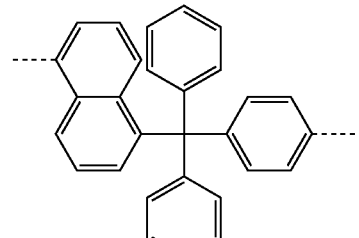

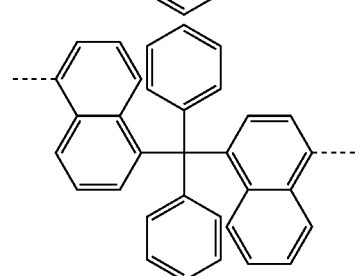

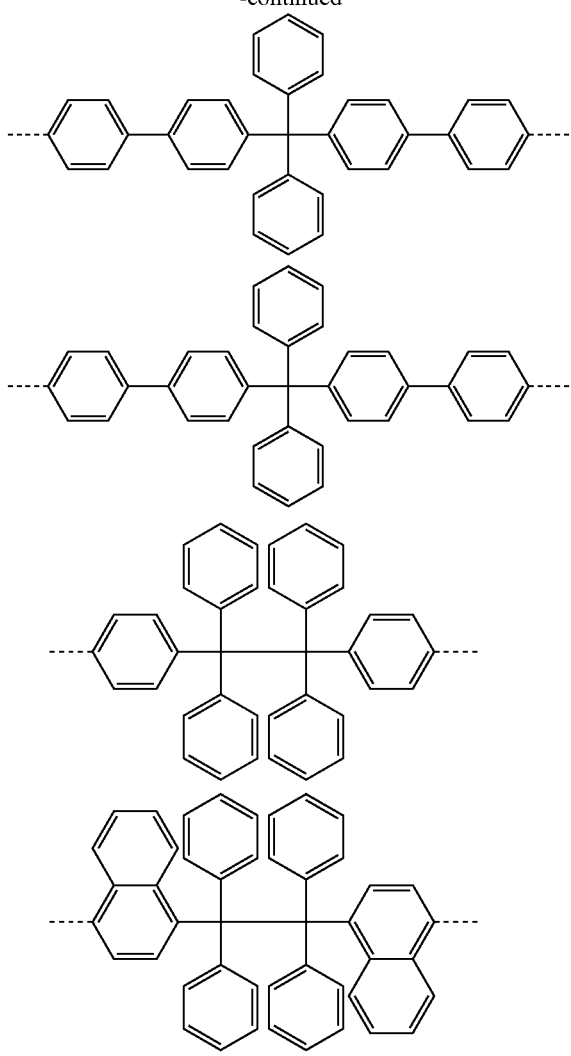
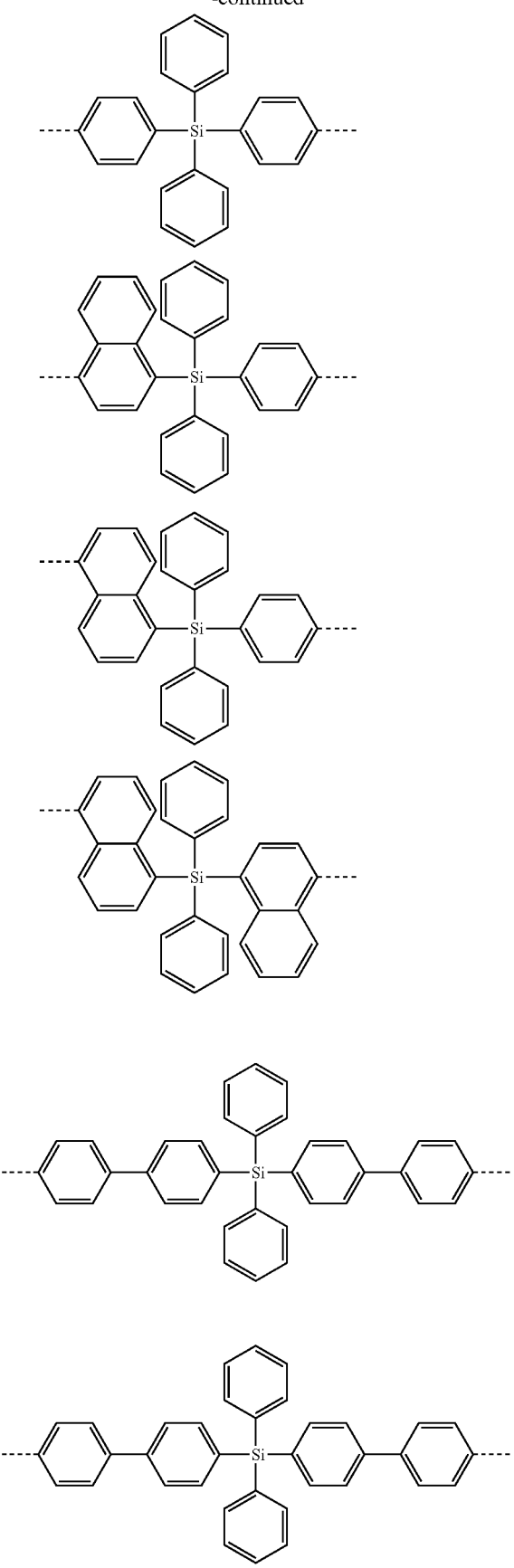

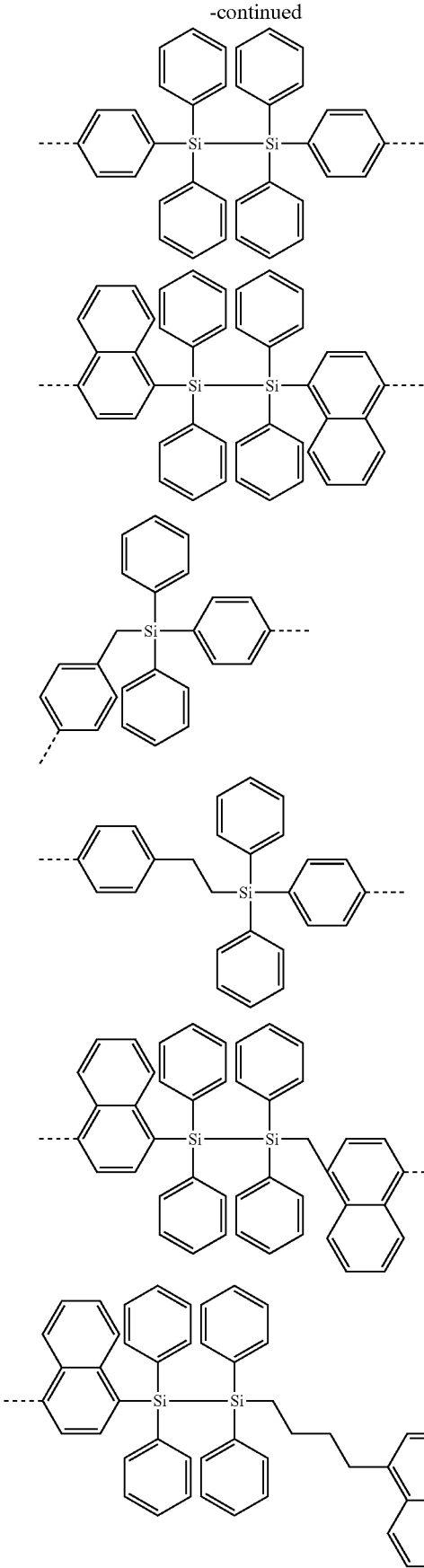
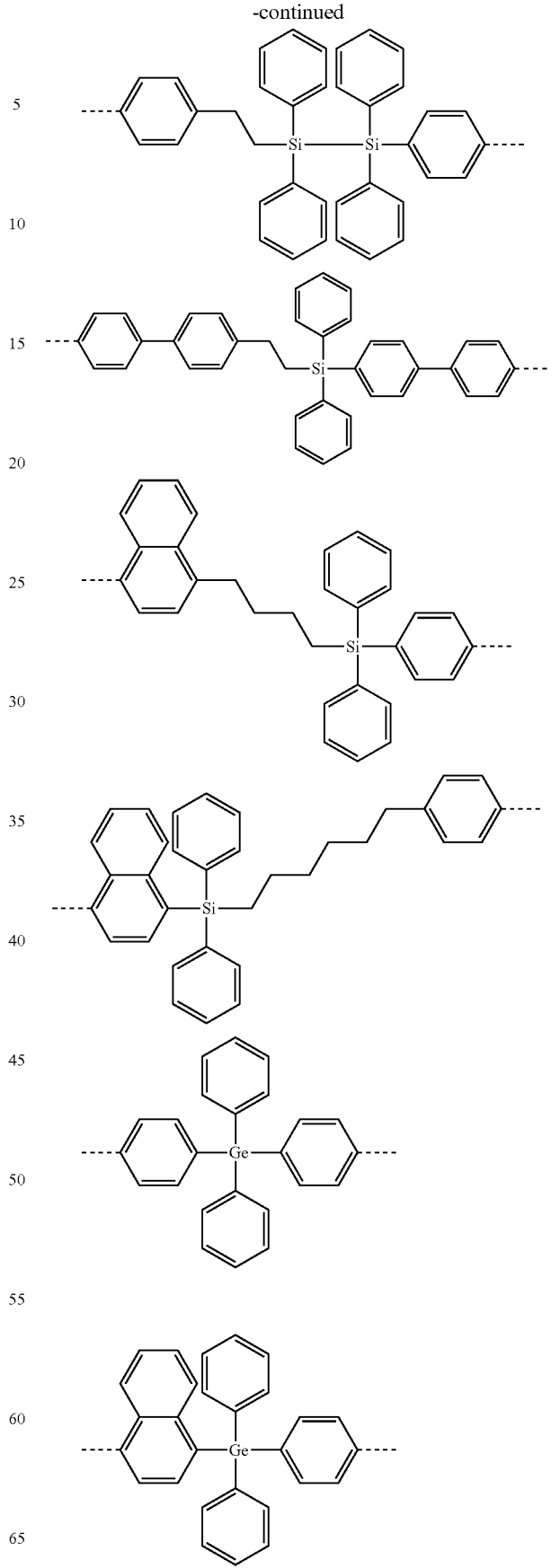

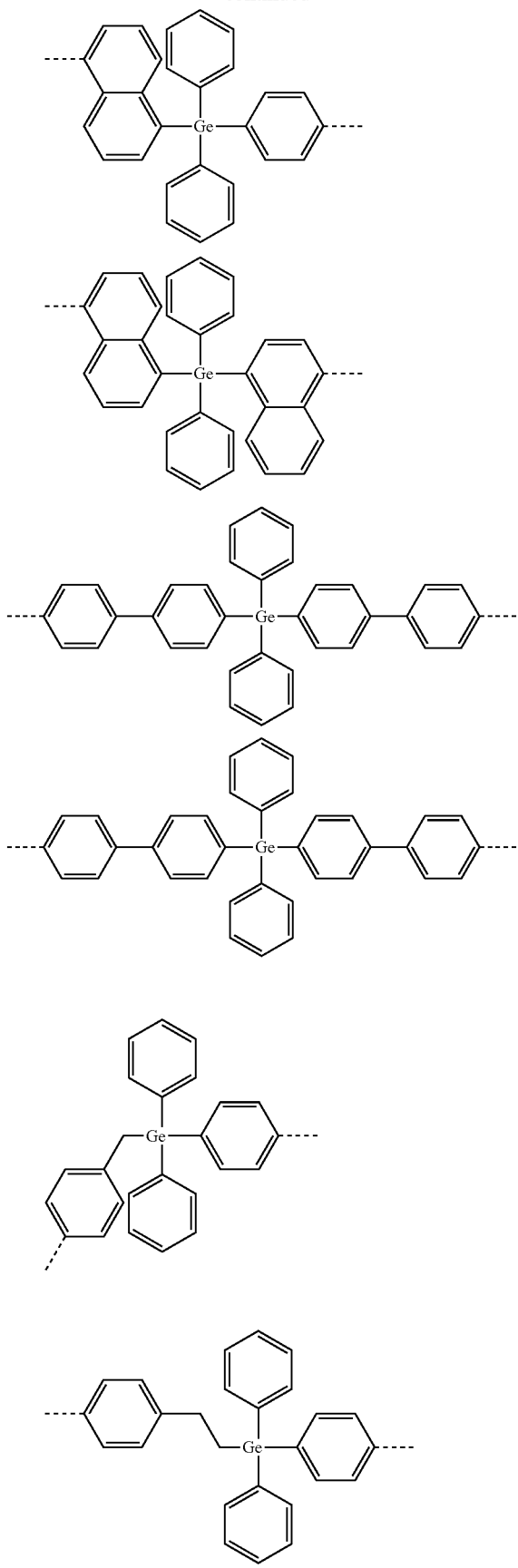

-continued

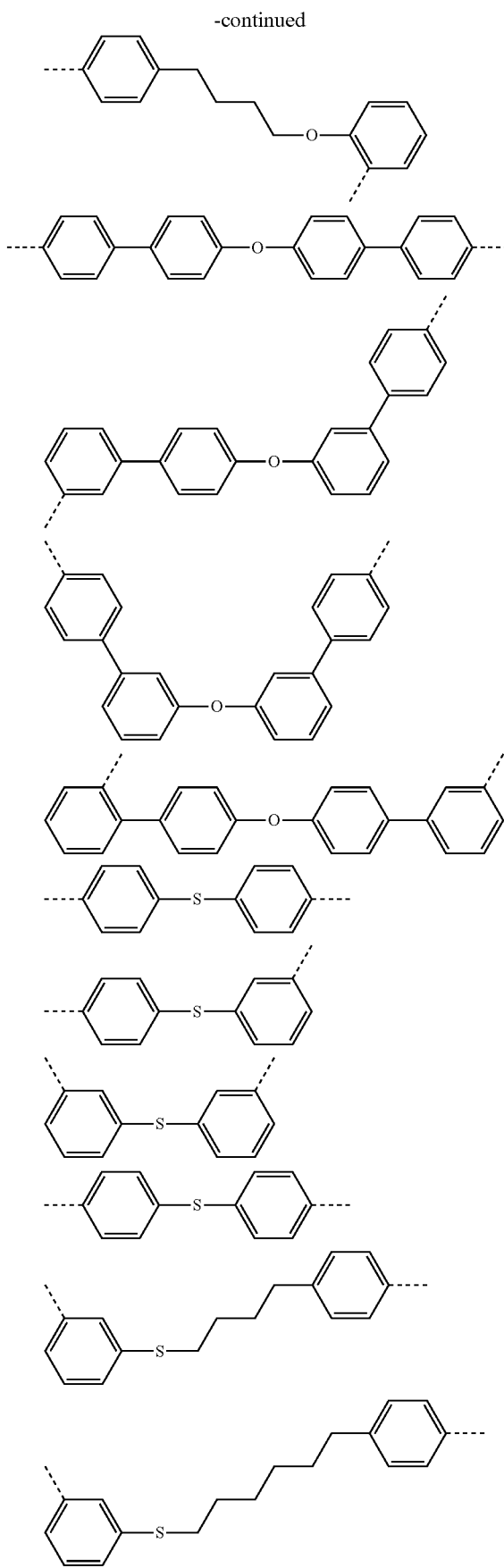

-continued

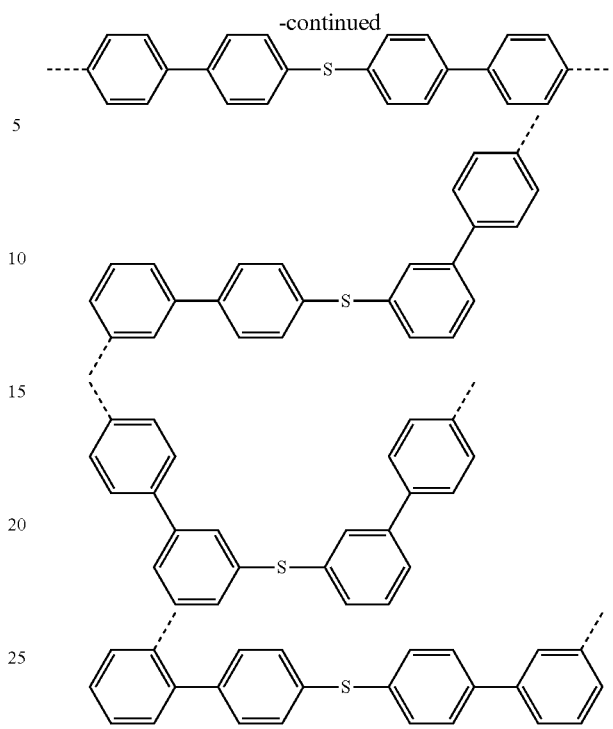

In a preferred embodiment of the invention, R is selected, identically or differently on each occurrence, from the group consisting of H, D, F, Cl, Br, CN, C(=O)Ar, a straight-chain alkyl or alkoxy group having 1 to 10 C atoms or a branched or cyclic alkyl or alkoxy group having 3 to 10 C atoms, each of which may be substituted by one or more radicals $R^1$, where one or more non-adjacent $CH_2$ groups may be replaced by O and where one or more H atoms may be replaced by D or F, an aromatic or heteroaromatic ring system having 5 to 30 aromatic ring atoms, which may in each case be substituted by one or more radicals $R^1$, or an aryloxy or heteroaryloxy group having 5 to 30 aromatic ring atoms, which may be substituted by one or more radicals $R^1$.

In a particularly preferred embodiment of the invention, R is selected, identically or differently on each occurrence, from the group consisting of H, D, F, CN, a straight-chain alkyl group having 1 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 18 aromatic ring atoms, which may in each case be substituted by one or more radicals $R^1$.

The radical R which is bonded to $Ar^5$ or $Ar^6$, i.e. which is bonded to the structure of the formula (2), is particularly preferably selected, identically or differently on each occurrence, from the group consisting of H, D or an aromatic or heteroaromatic ring system having 6 to 18 aromatic ring atoms, where the aromatic or heteroaromatic ring system is selected, in particular, from the group consisting of phenyl, ortho-, meta- or para-biphenyl, ortho-, meta-, para- or branched terphenyl and quaterphenyl.

For compounds which are processed by vacuum evaporation, the alkyl groups preferably have not more than four C atoms, particularly preferably not more than 1 C atom. For compounds which are processed from solution, compounds which are substituted by alkyl groups having up to 10 C atoms or which are substituted by oligoarylene groups, for example ortho-, meta-, para- or branched terphenyl or quaterphenyl groups, are also suitable.

In a preferred embodiment of the invention, $R^1$ is selected, identically or differently on each occurrence, from the group consisting of H, D, F, CN, a straight-chain alkyl group having 1 to 10 C atoms or a branched or cyclic alkyl group having 3 to 10 C atoms, where one or more H atoms may be replaced by D or F, or an aromatic or heteroaromatic ring system having 5 to 30 aromatic ring atoms, which may in each case be substituted by one or more radicals $R^2$.

In a particularly preferred embodiment of the invention, $R^1$ is selected, identically or differently on each occurrence, from the group consisting of H, D, F, CN, a straight-chain alkyl group having 1 to 5 C atoms or a branched or cyclic alkyl group having 3 to 5 C atoms, or an aromatic or heteroaromatic ring system having 5 to 18 aromatic ring atoms.

Examples of preferred compounds of the above-mentioned embodiments are the compounds of the following structures.

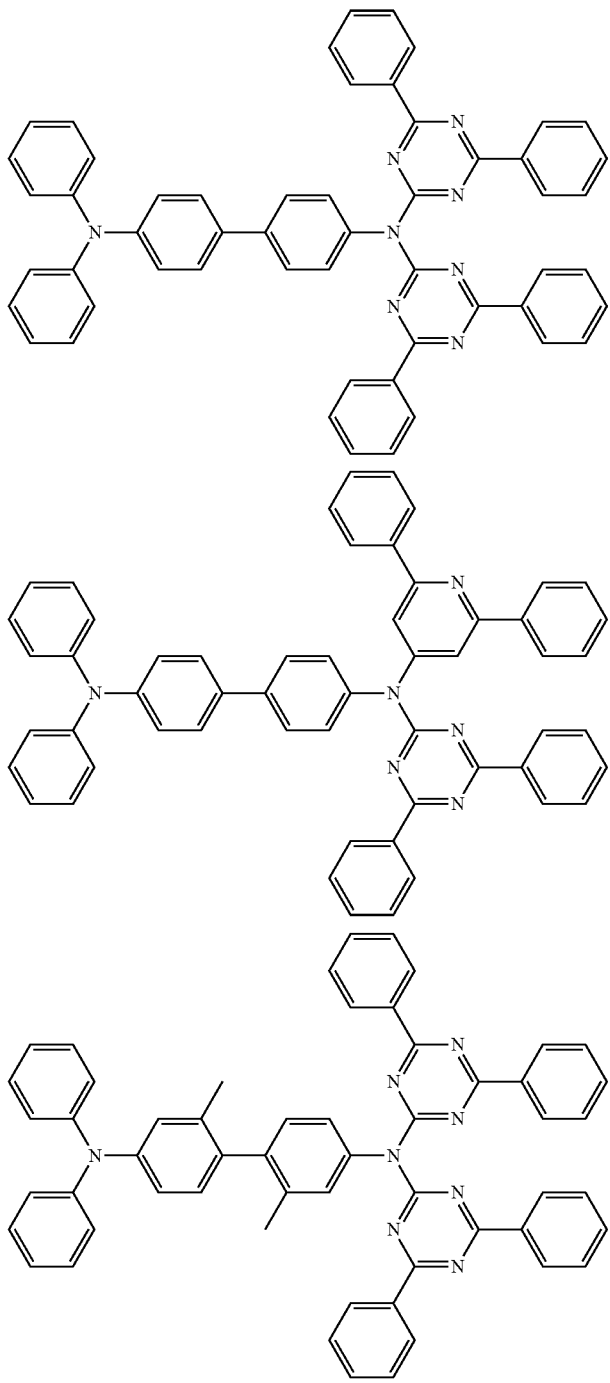

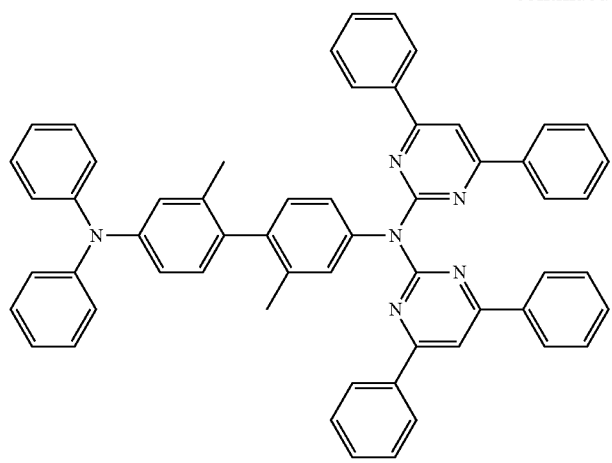
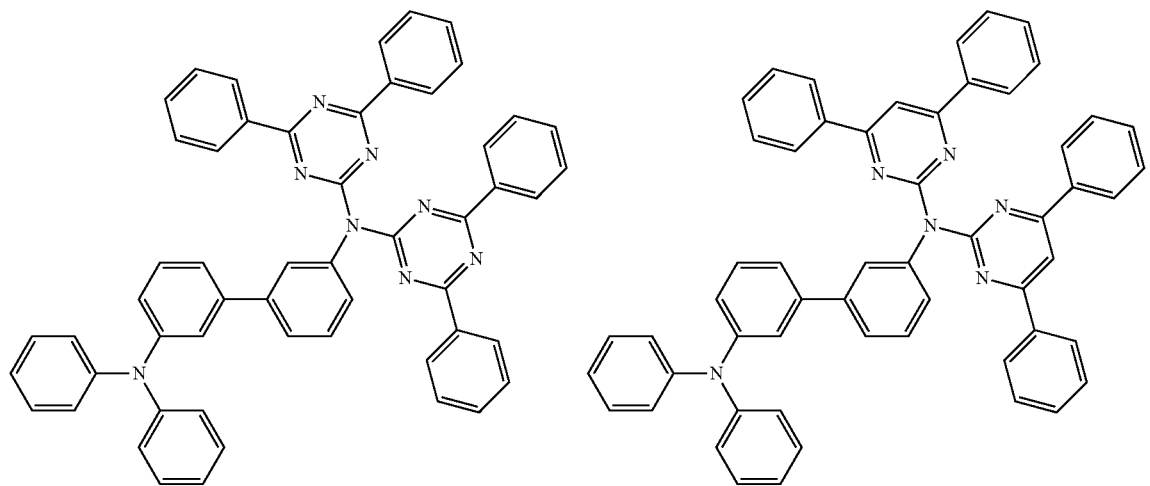
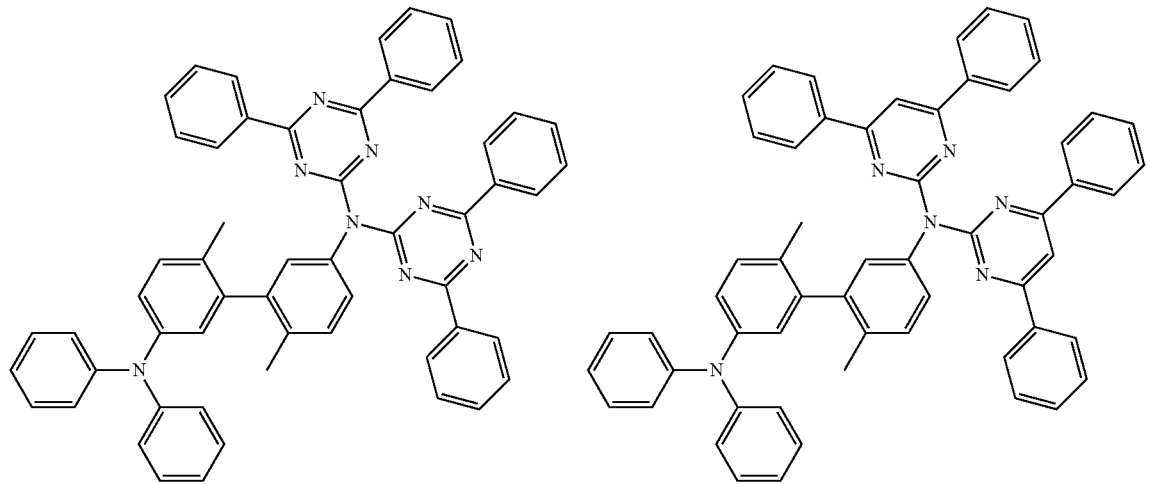

41 42
-continued
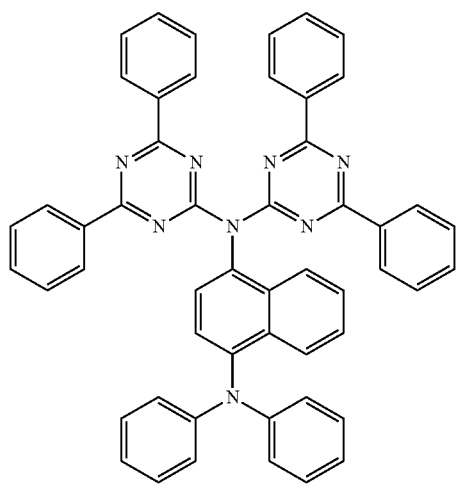
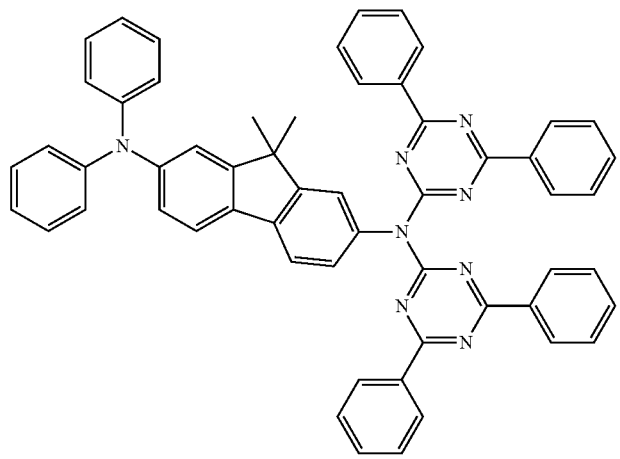
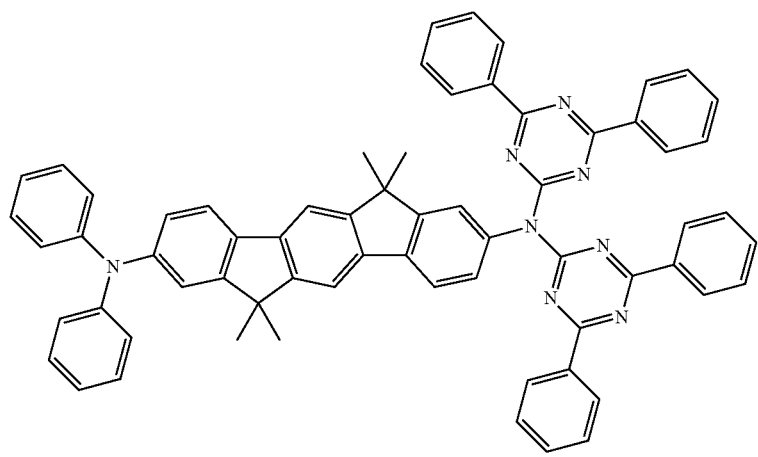
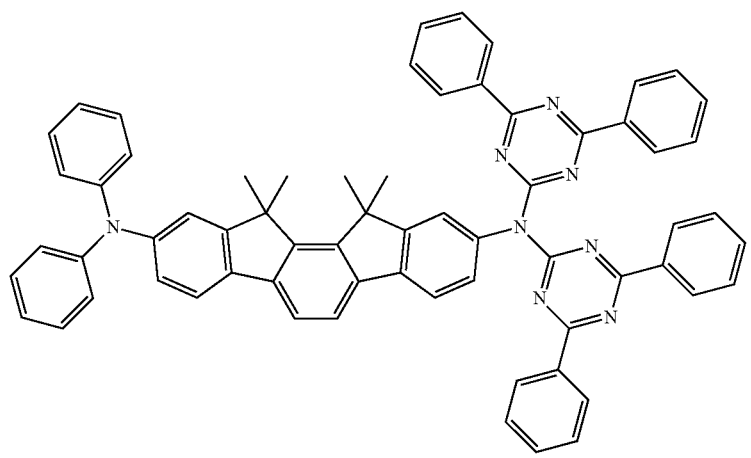

-continued
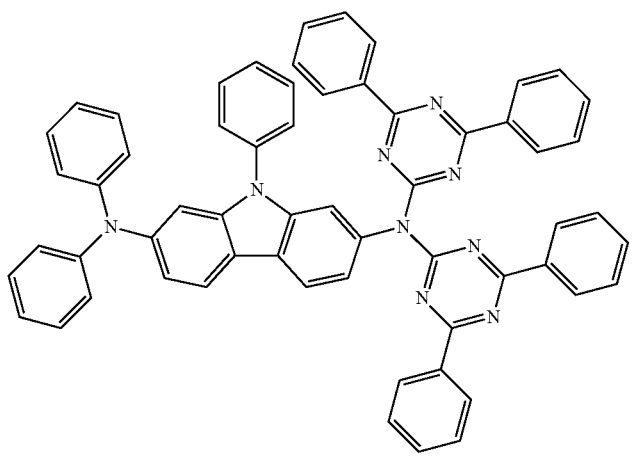
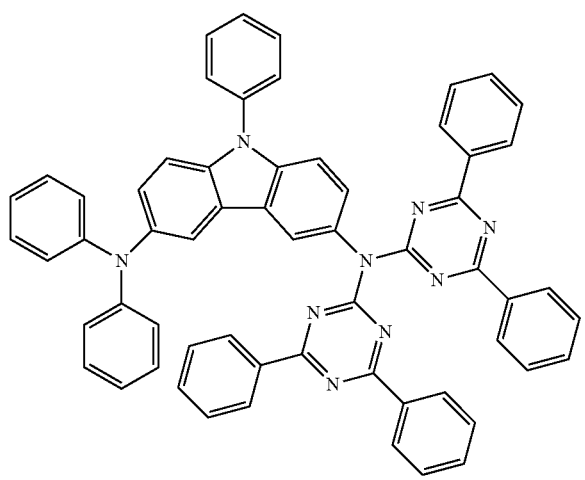
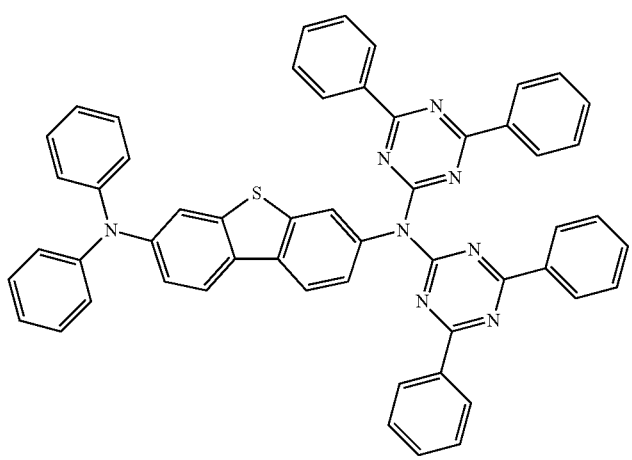

-continued
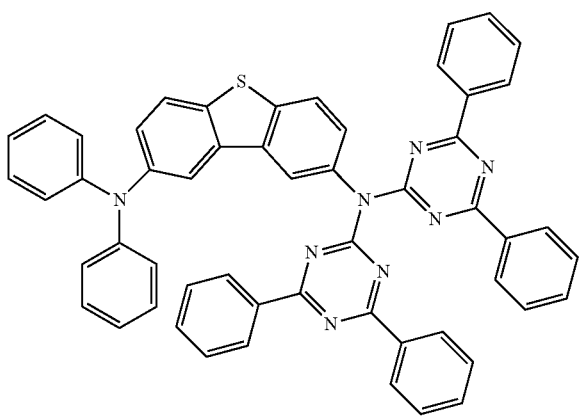
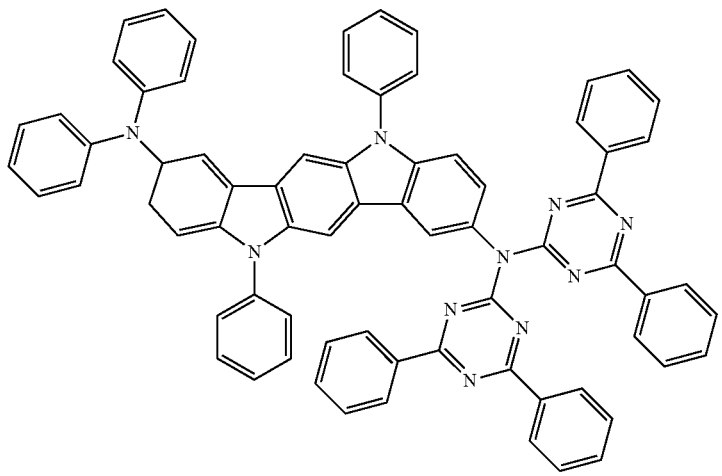
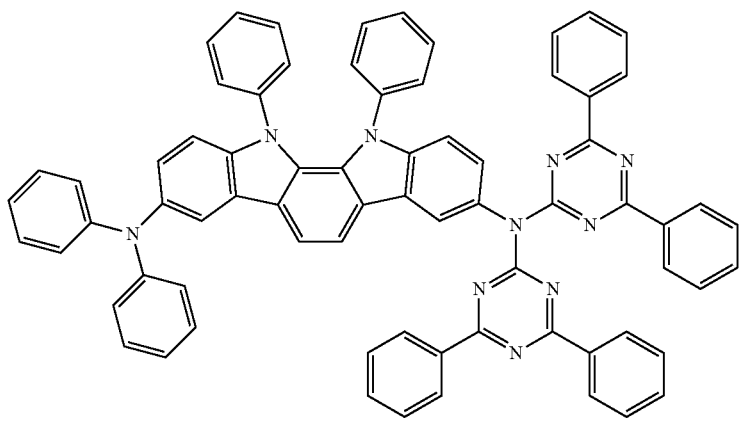

-continued
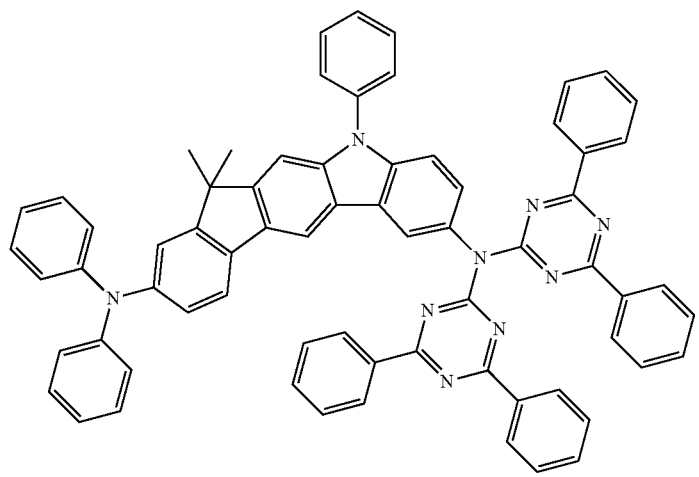
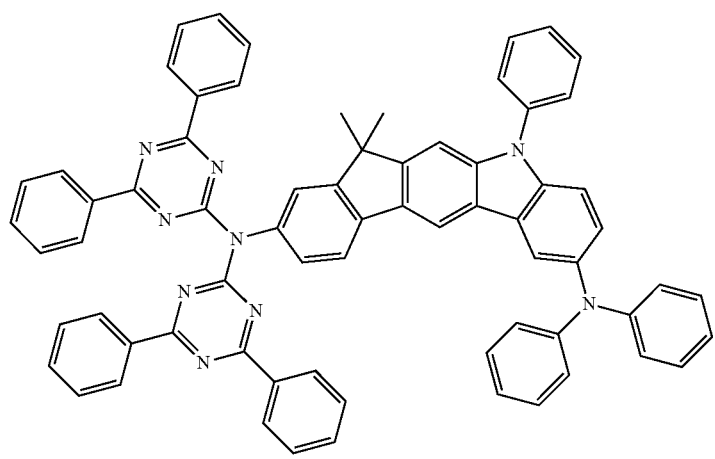
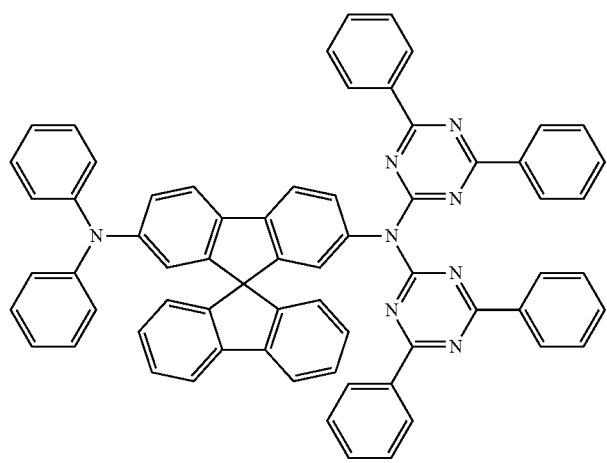

-continued
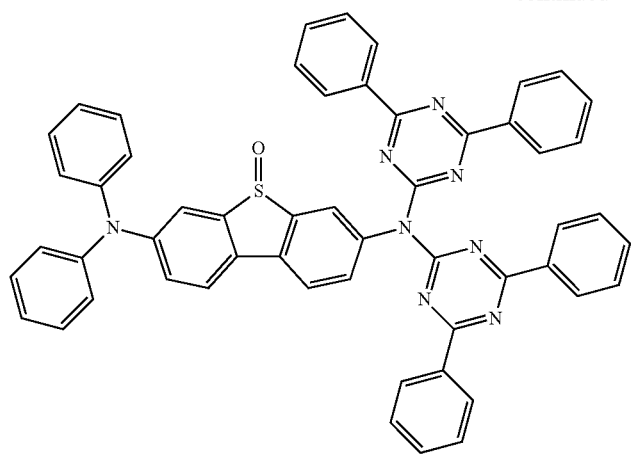
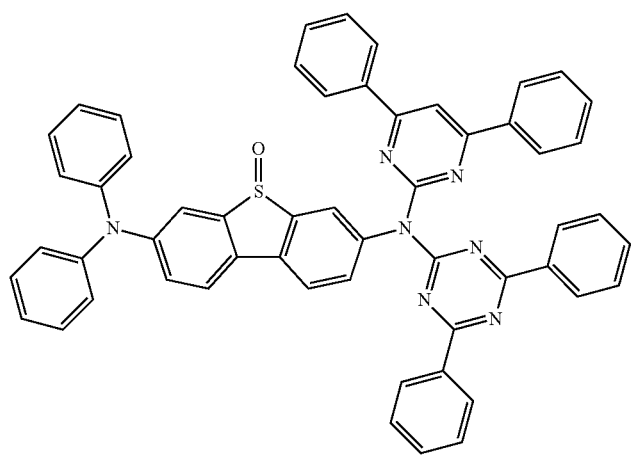
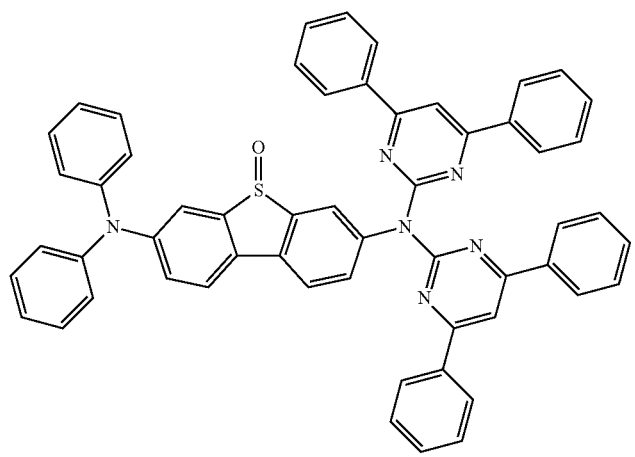

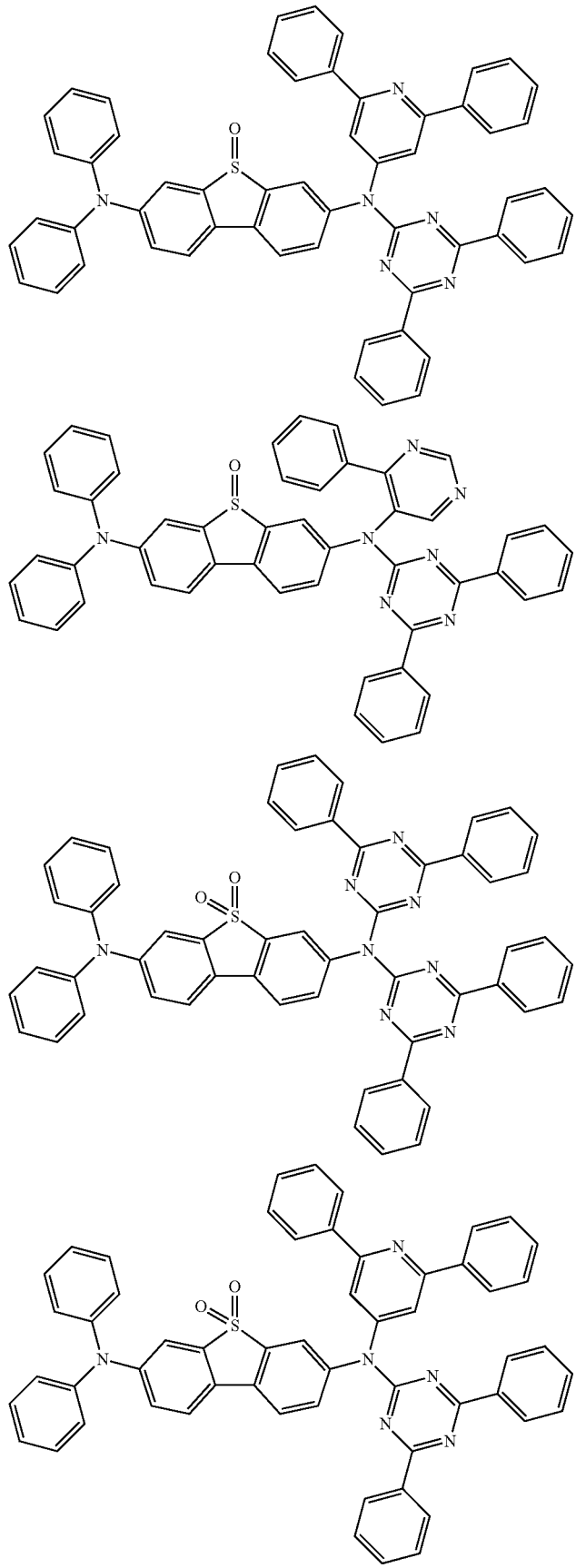

-continued
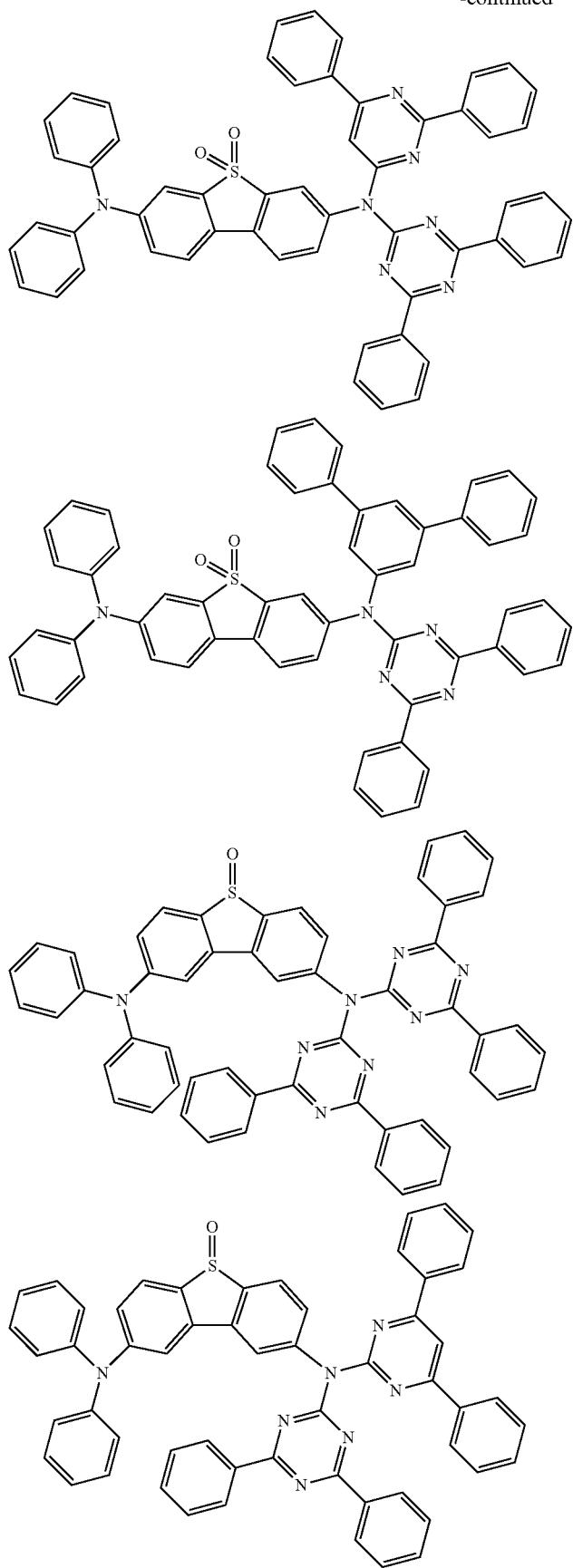

-continued
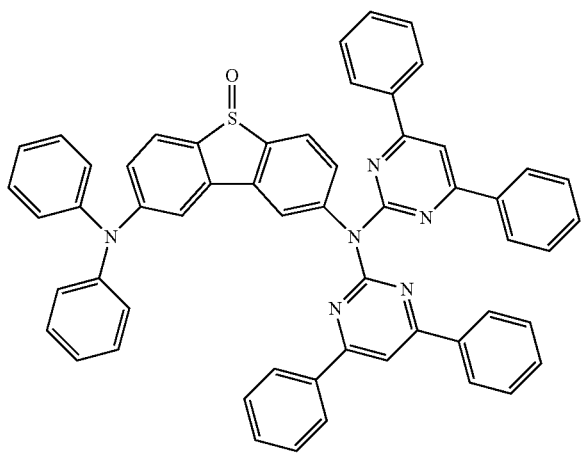
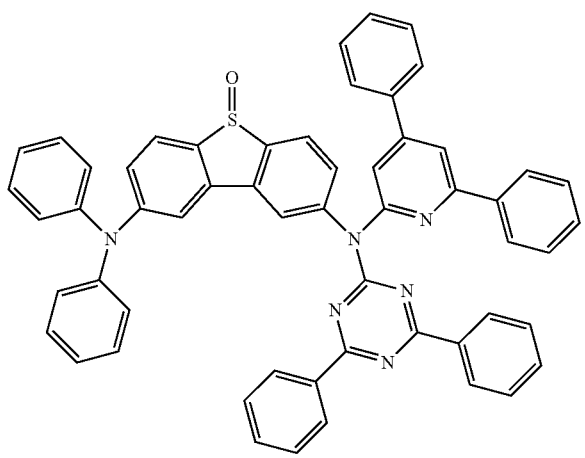
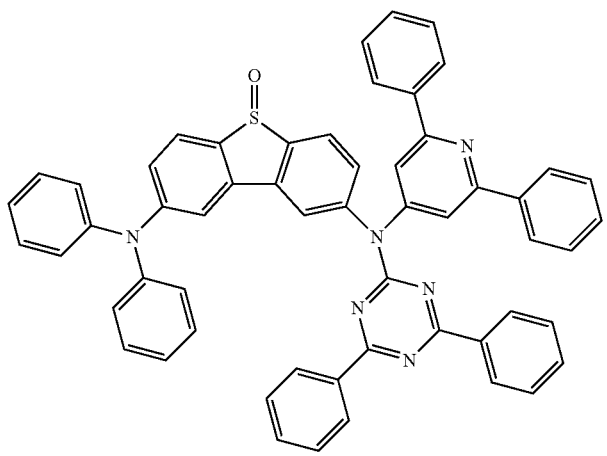

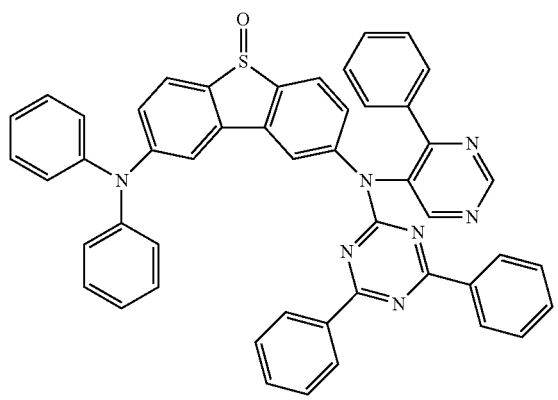
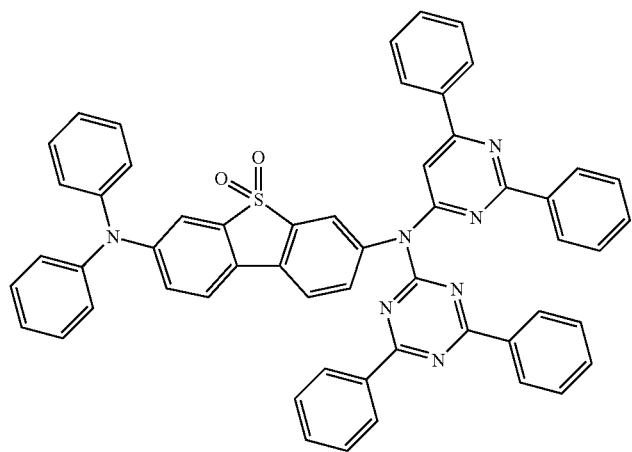
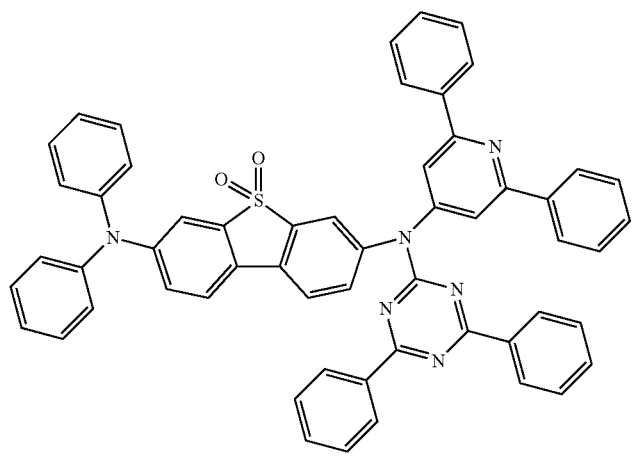

-continued
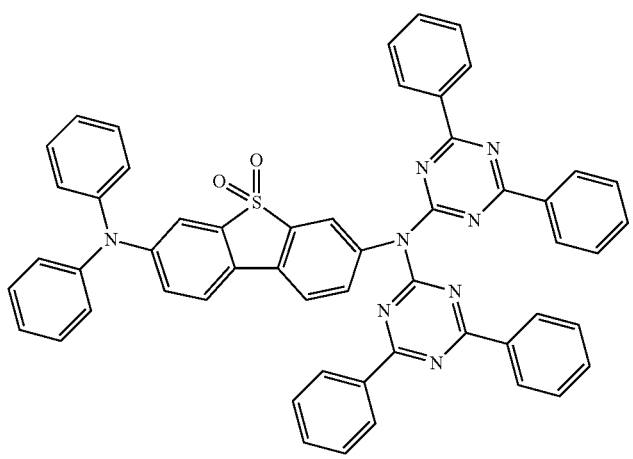
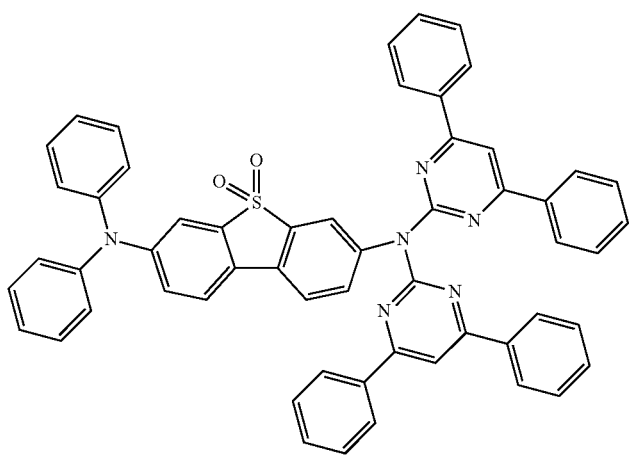
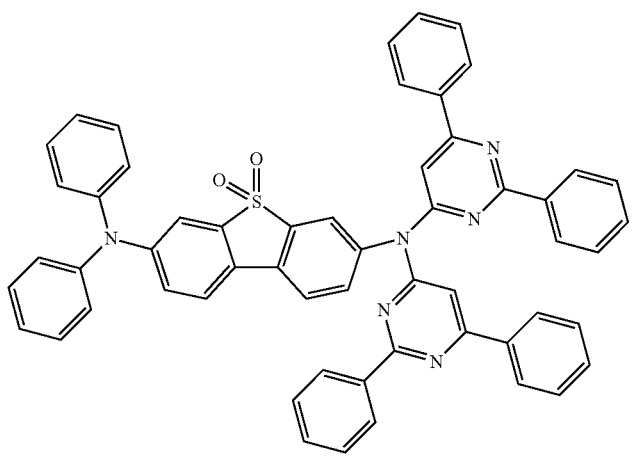

-continued
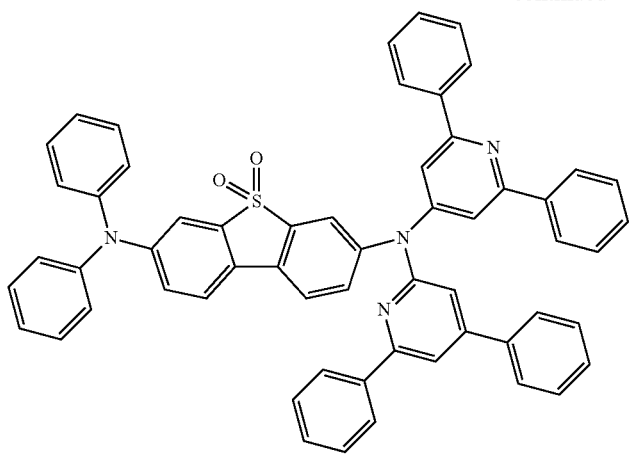
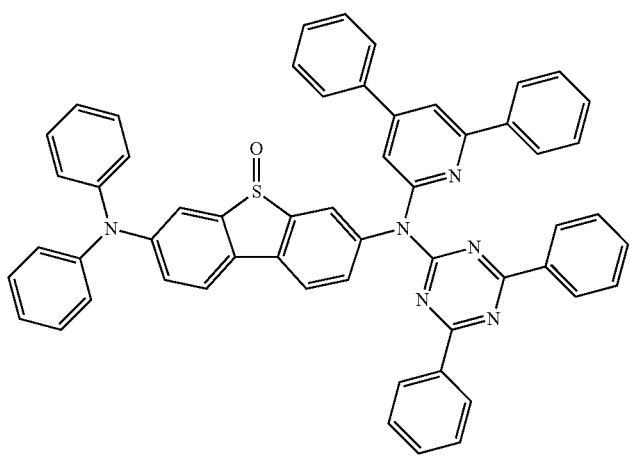
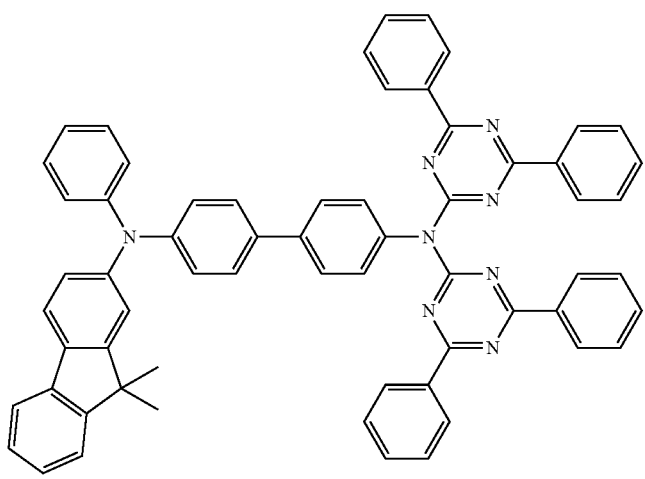

-continued
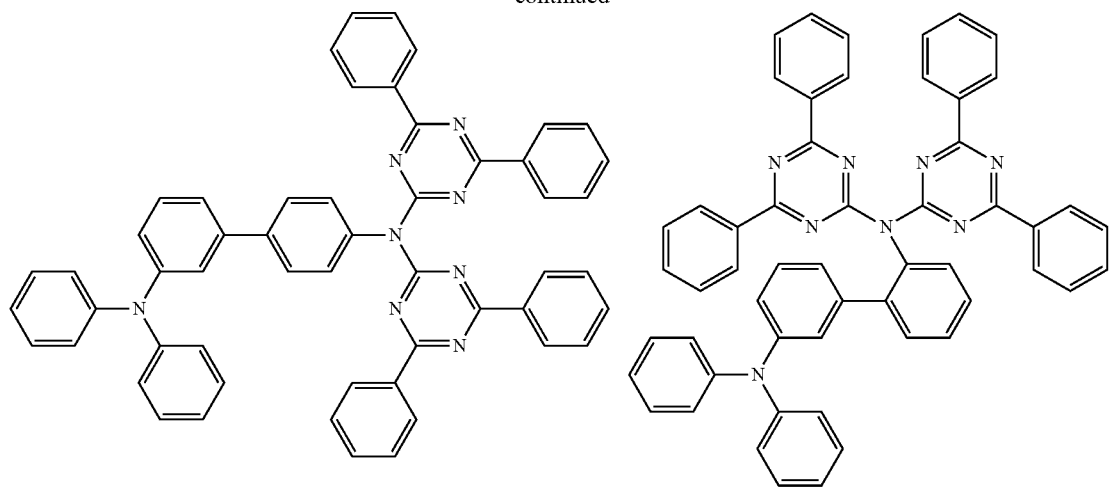
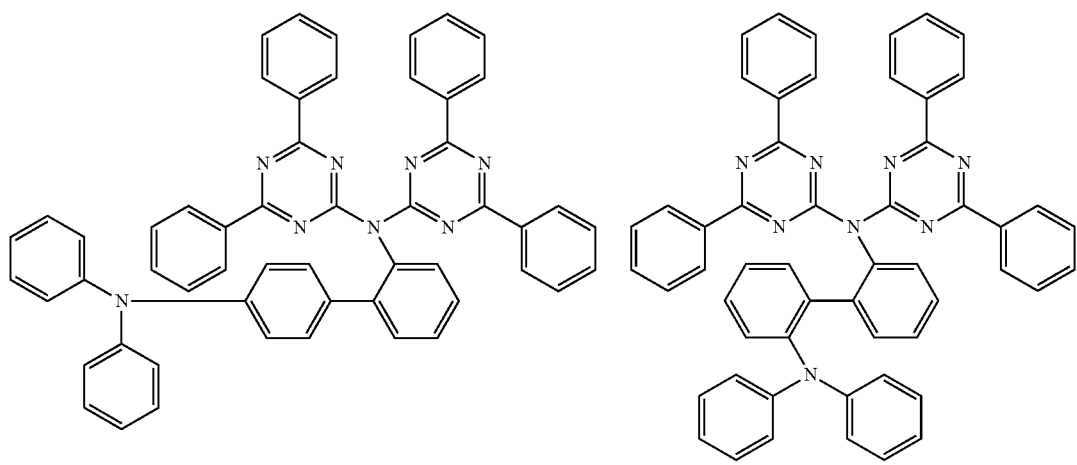
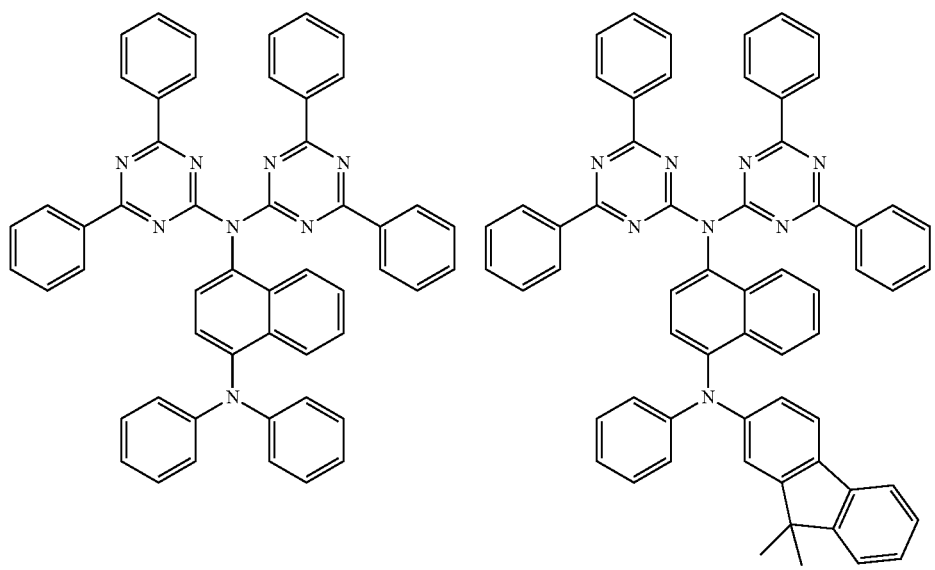

-continued
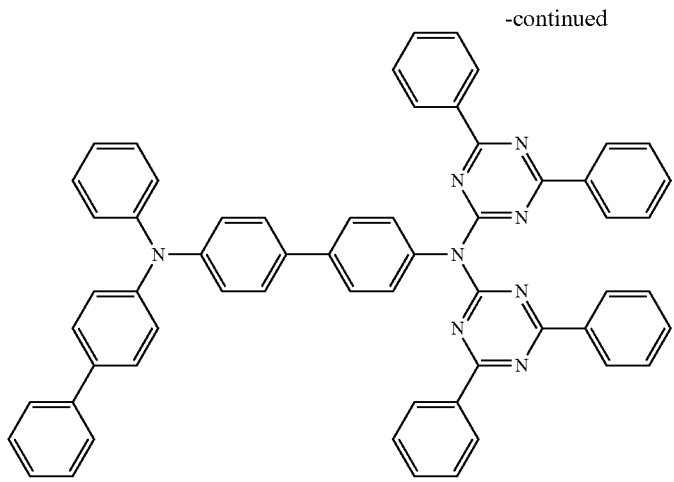
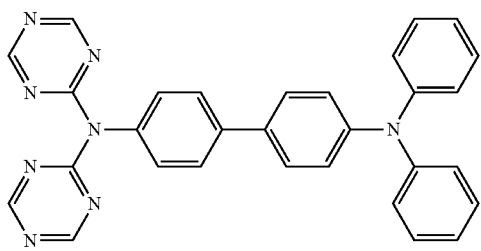
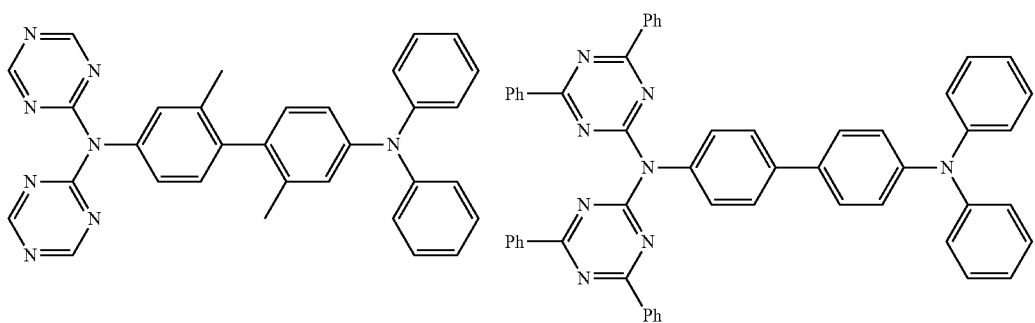
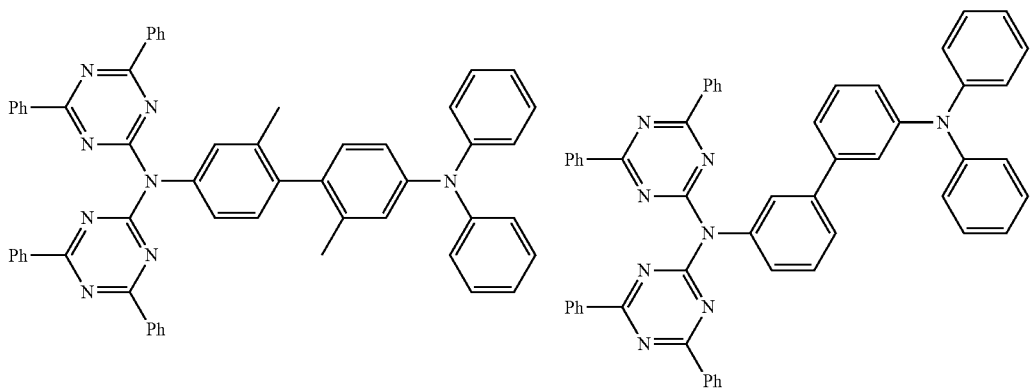

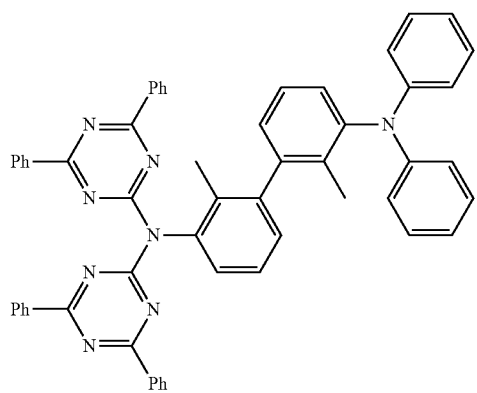
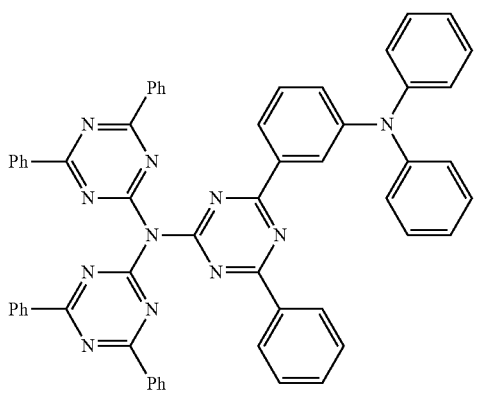
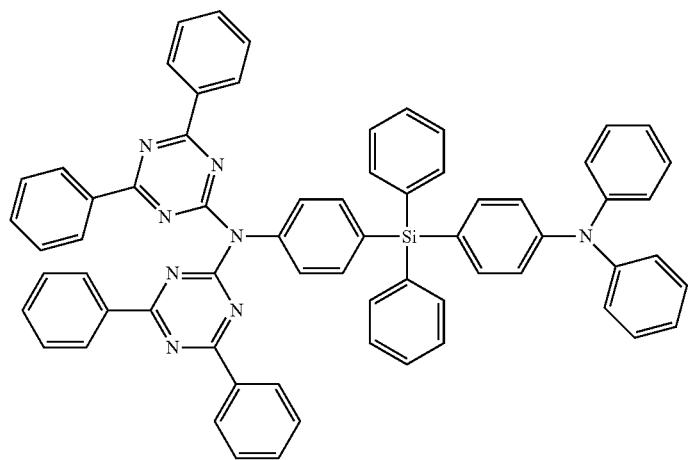
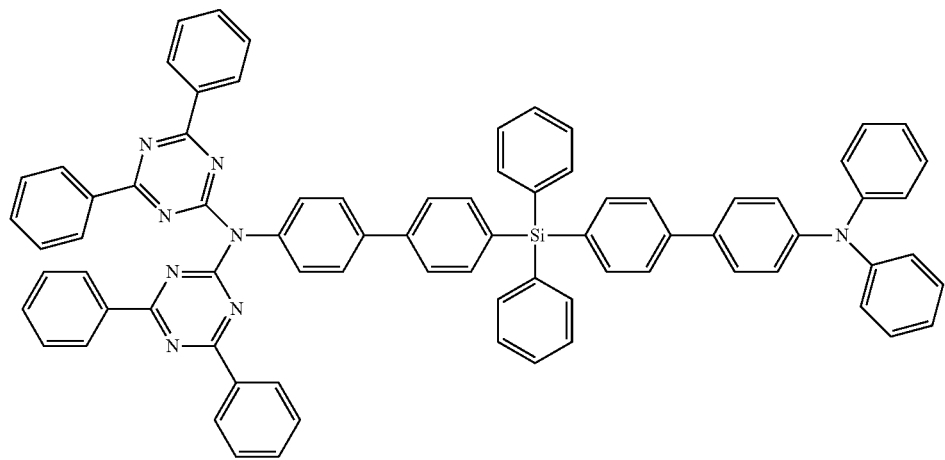

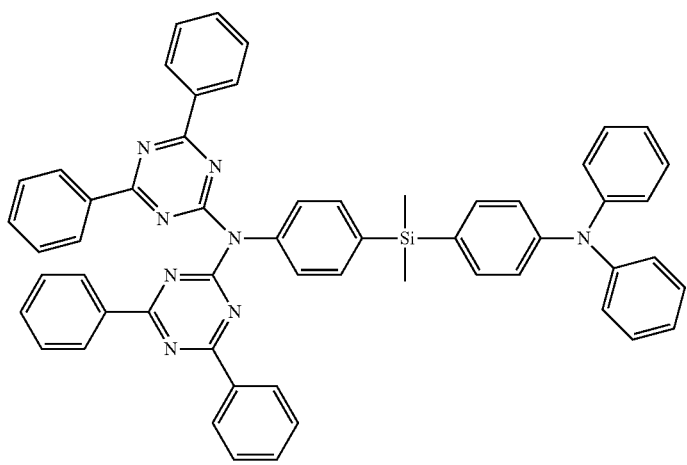
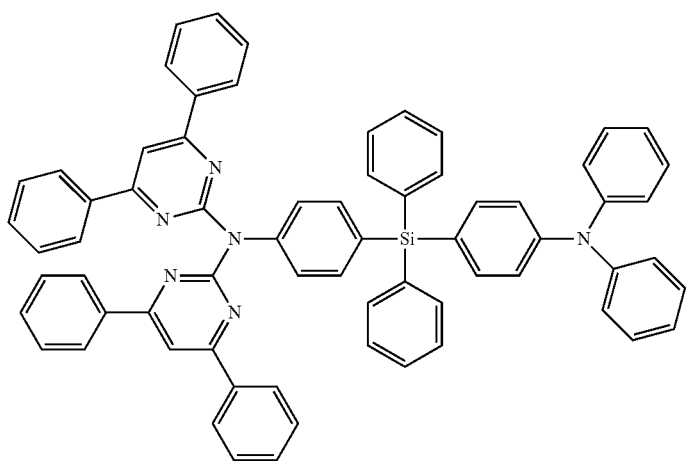
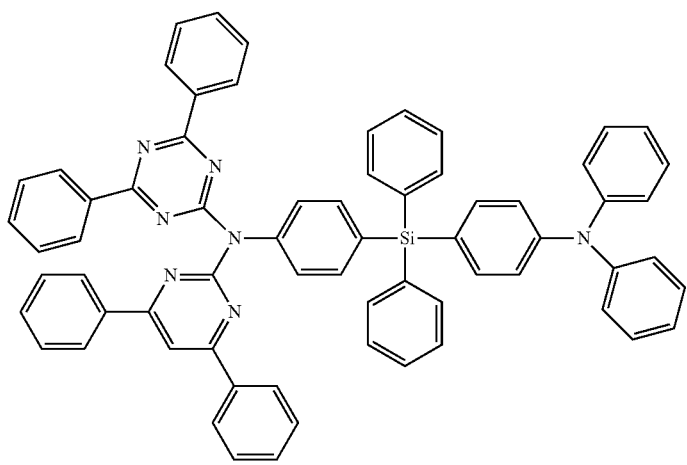

-continued
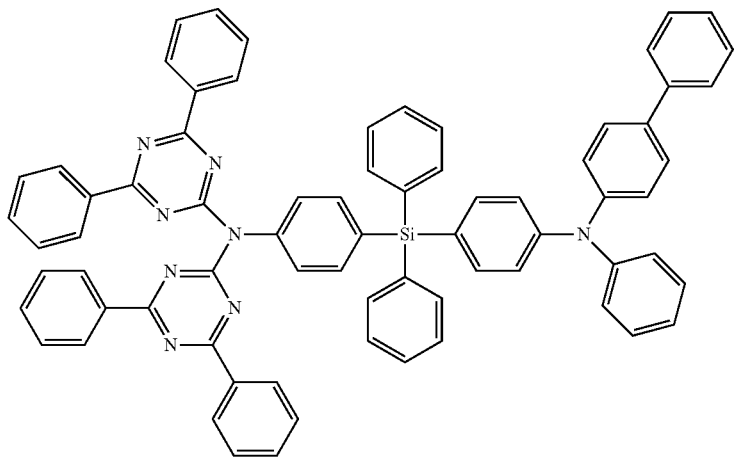
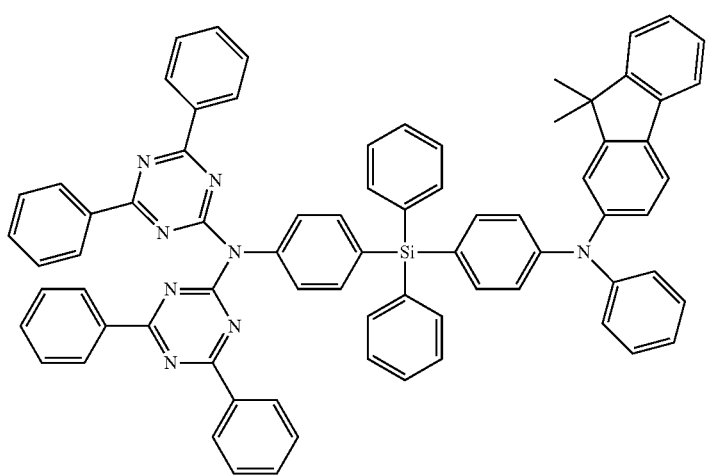
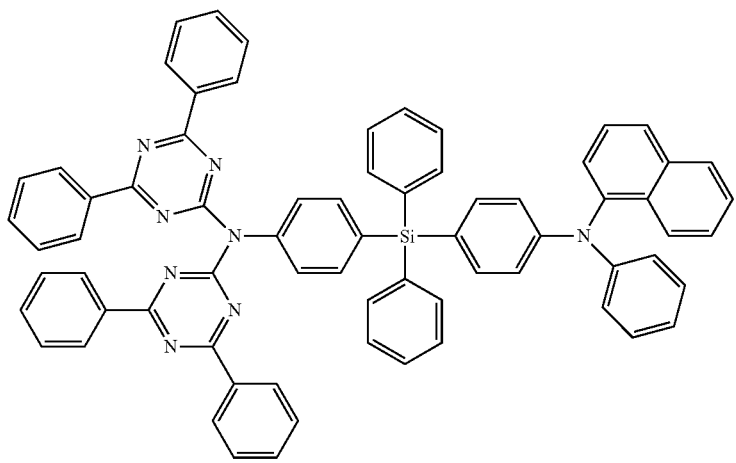

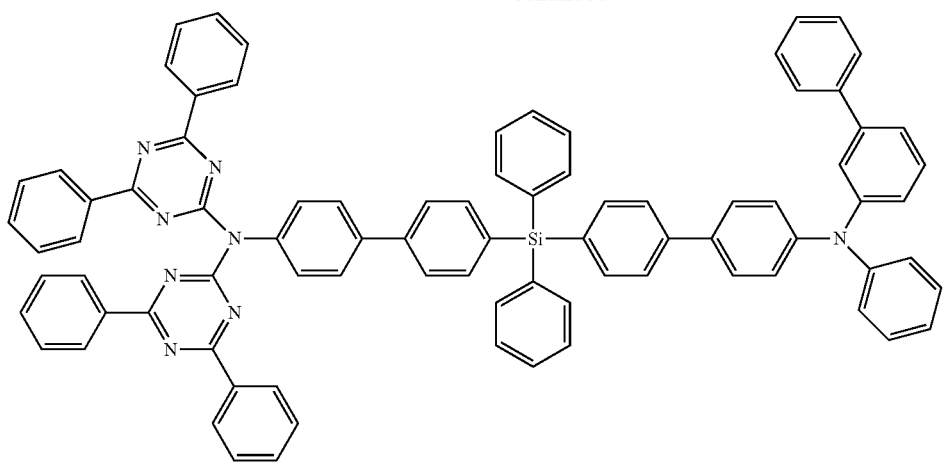
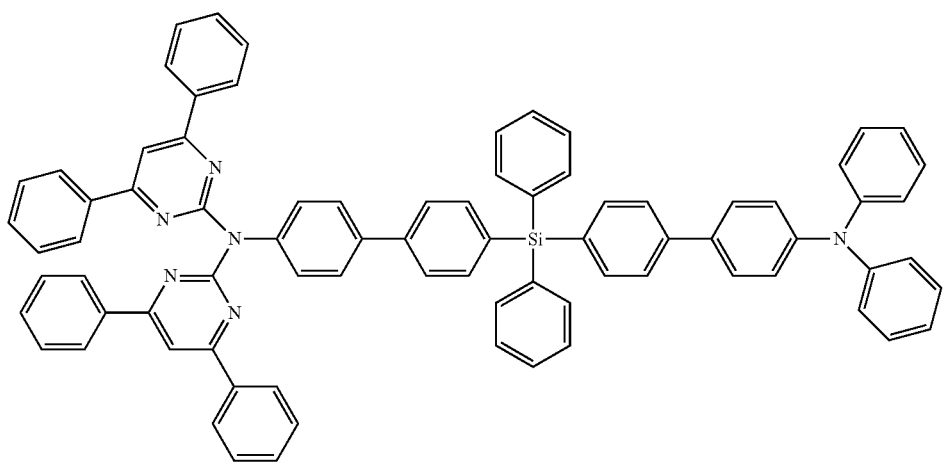
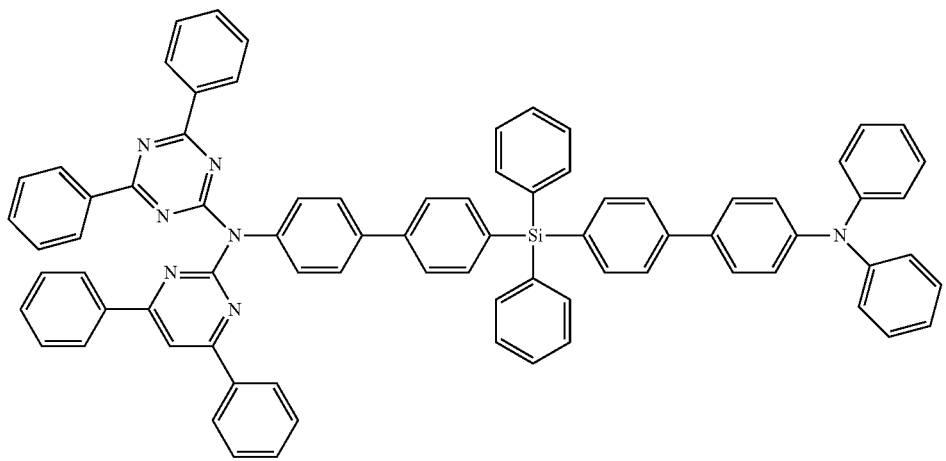

-continued
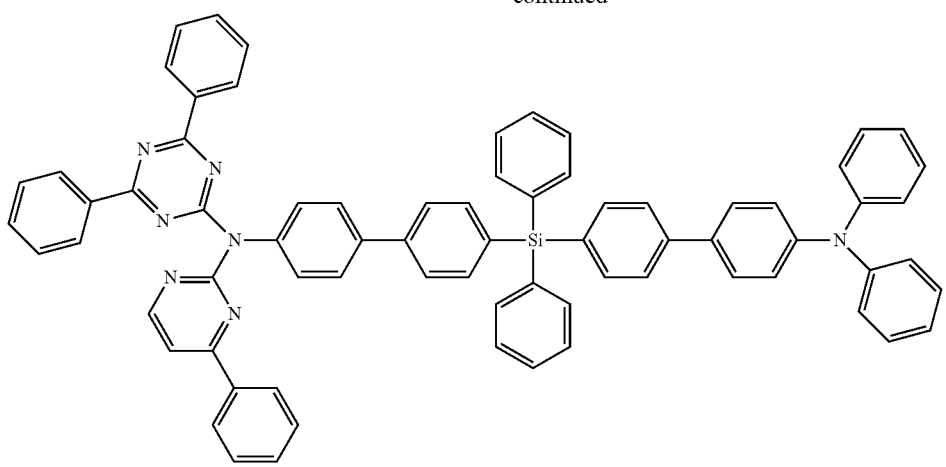
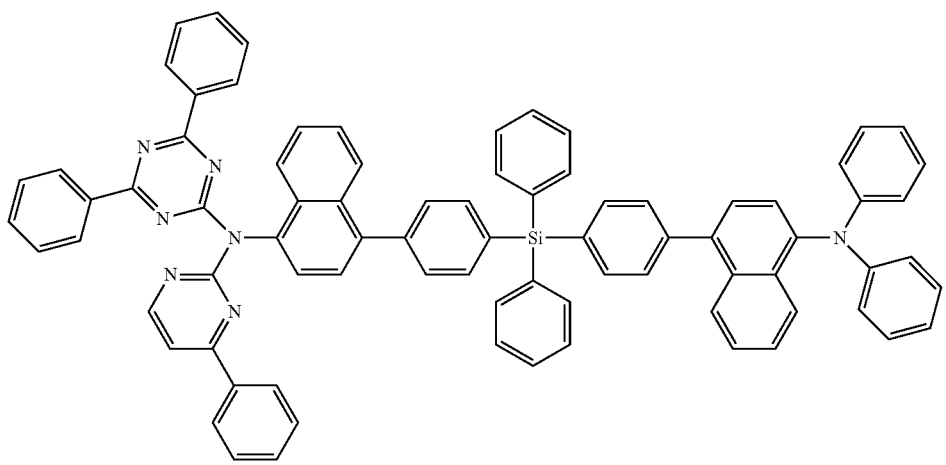
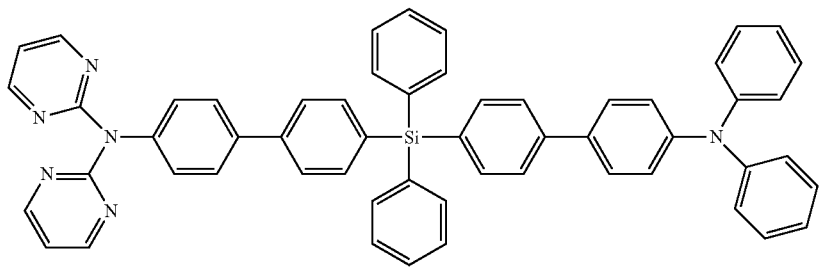
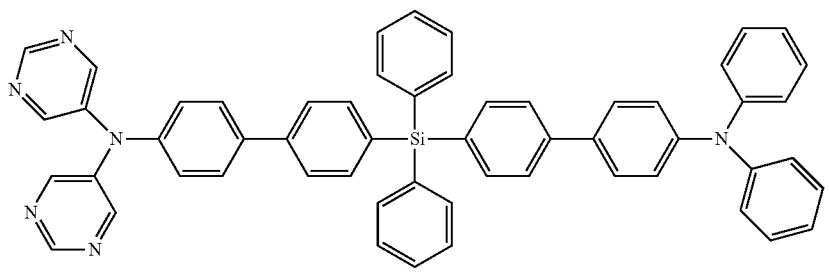

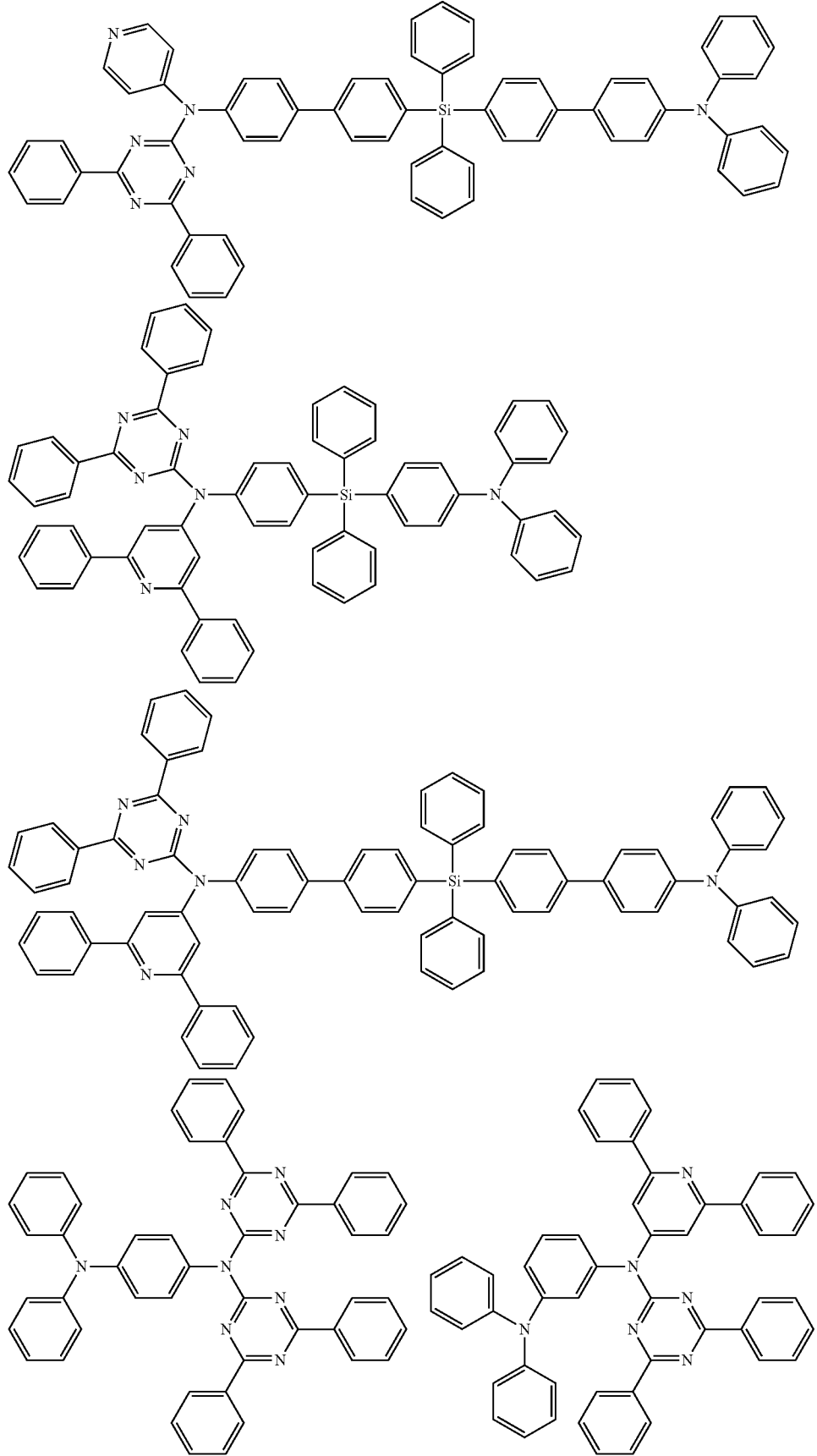

-continued
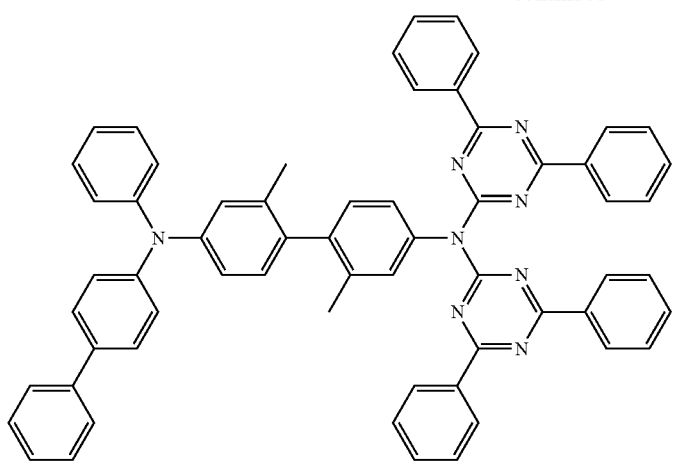
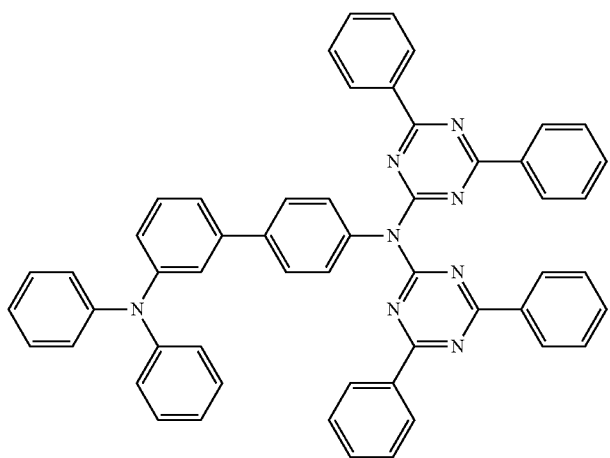
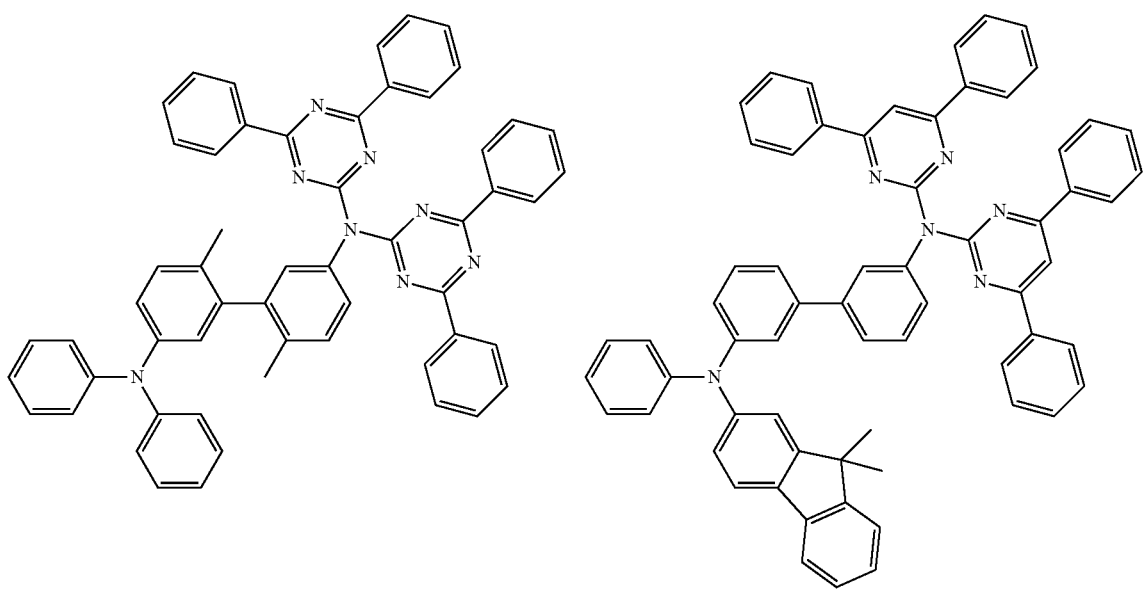

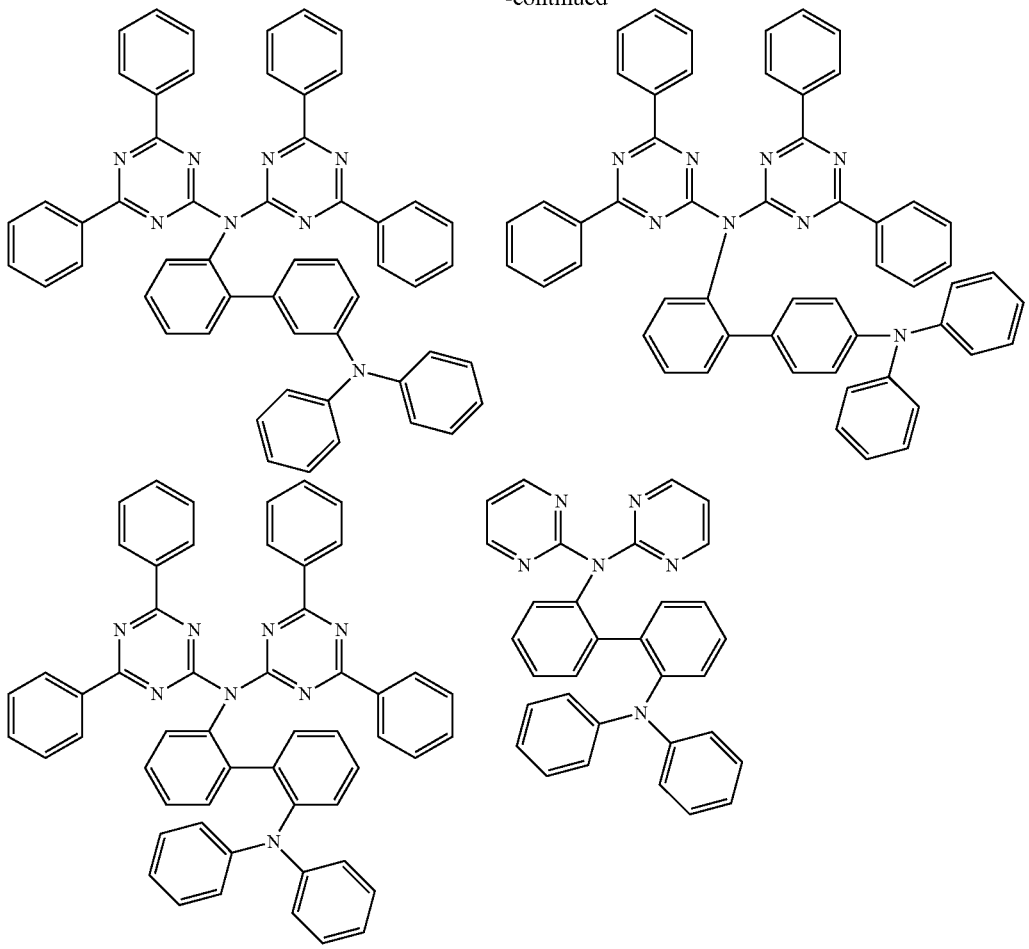

The compounds according to the invention can be prepared by synthetic steps known to the person skilled in the art, such as, for example, bromination, Ullmann arylation, Hartwig-Buchwald coupling, etc., as depicted for two example compounds in Scheme 1 and 2. Further derivatives of the compounds according to the invention can be prepared entirely analogously. Thus, for example, a group L, L-Ar$^4$, Ar$^4$ or Ar$^3$-L-Ar$^4$ which is simultaneously substituted by a reactive leaving group, for example chlorine, bromine or iodine, and by an amino group can be reacted with a derivative of the group Ar$^5$ which is substituted by a reactive leaving group, for example fluorine, chlorine, bromine or iodine. This reaction can be carried out either as a nucleophilic aromatic substitution, if necessary with addition of a base, or in a metal-catalysed coupling reaction, for example a Hartwig-Buchwald coupling. The group Ar$^6$ can be introduced entirely analogously in a further step. The reactive leaving group on Ar$^3$ or L can then be reacted, in a subsequent step, with a compound Ar$^1$Ar$^2$NH in a metal-promoted coupling reaction, for example an Ullmann coupling or a Hartwig-Buchwald coupling. The reactive leaving group on L can furthermore be reacted, in a subsequent step, with a compound Ar$^1$Ar$^2$NAr$^4$, or the reactive leaving group on Ar$^4$ can be reacted, in a subsequent step, with a compound Ar$^1$Ar$^2$NAr$^3$ or Ar$^1$Ar$^2$NAr$^3$L, which is substituted by a reactive group, for example a boronic acid or a boronic acid ester, to give the compound of the formula (1) according to the invention. Suitable coupling reactions are, for example, Suzuki coupling or Stille coupling.

Scheme 1

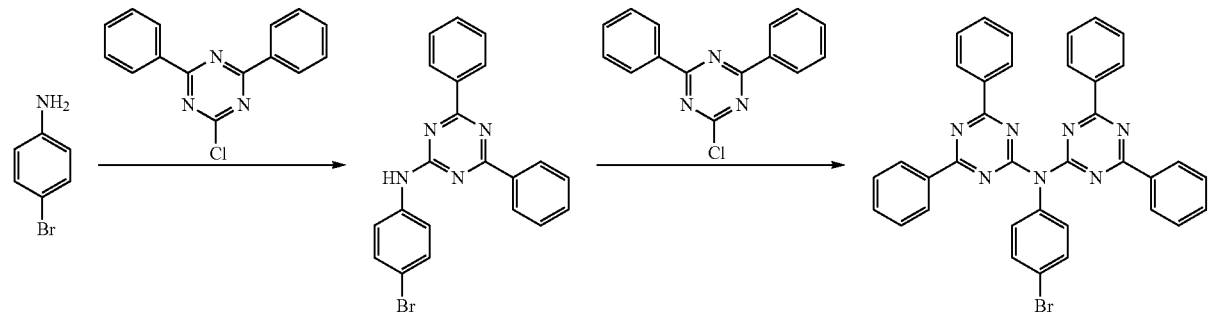

83 84
-continued
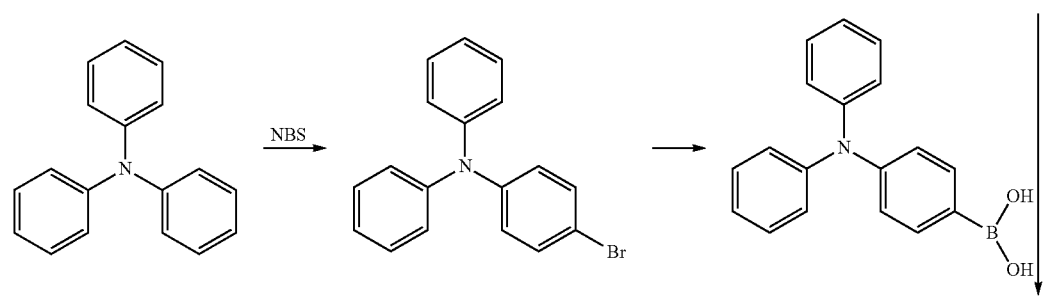
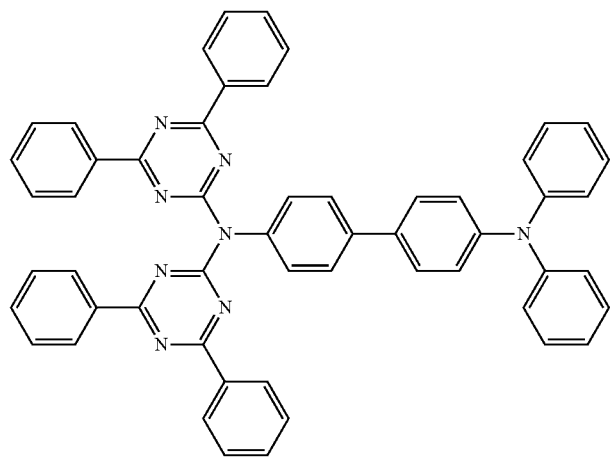
Scheme 2
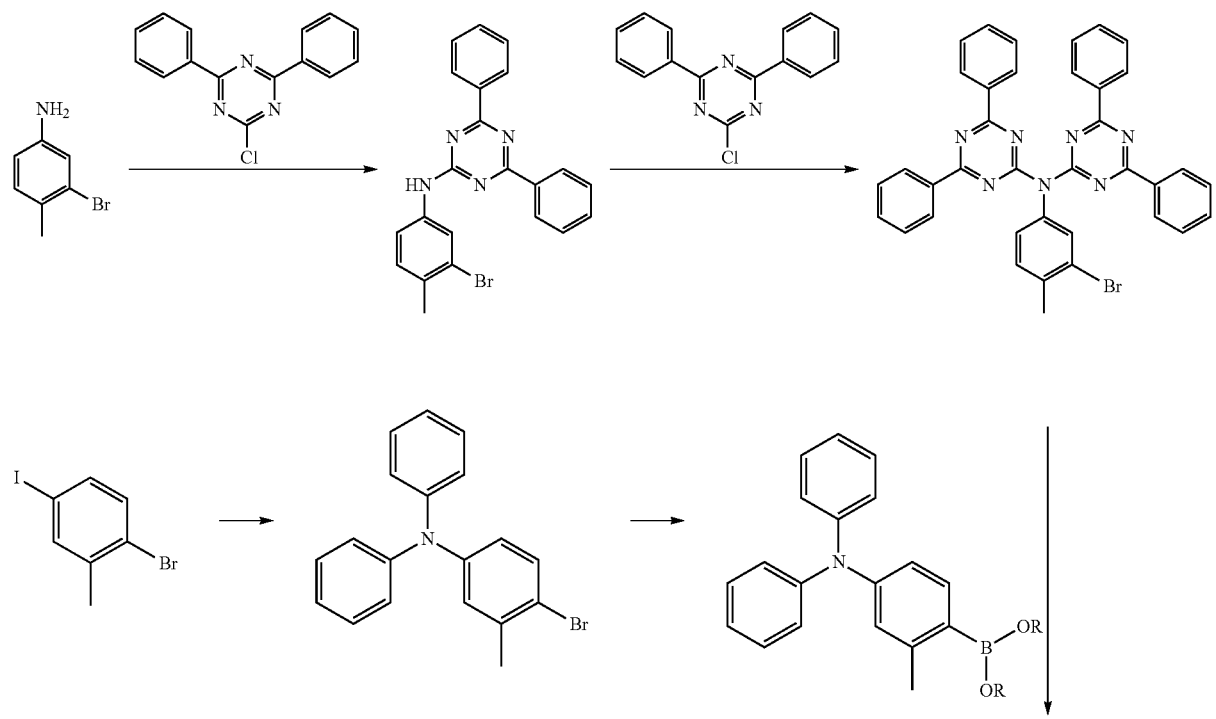

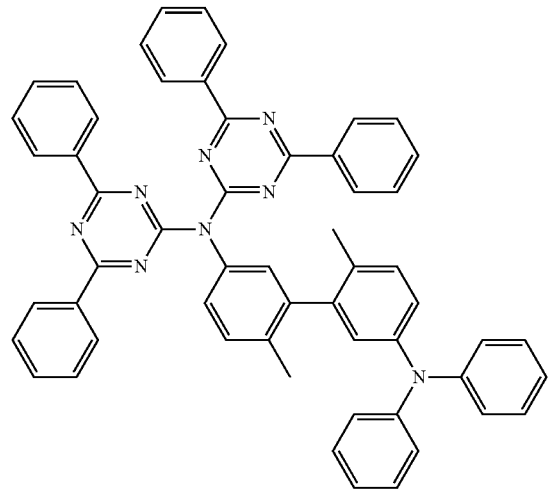

The present invention therefore furthermore relates to a process for the preparation of a compound of the formula (1), comprising the reaction steps:
a) synthesis of a compound G-(Ar³)$_n$-L-(Ar⁴)$_m$—NAr⁵Ar⁶ by reaction of a compound G-(Ar³)$_n$-L-(Ar⁴)$_m$—NH$_2$ with a compound G-Ar⁵ and G-Ar⁶, optionally with addition of a base and/or a catalyst, where G stands for a reactive leaving group, in particular fluorine, chlorine, bromine or iodine; and
b) introduction of the group Ar¹Ar²N— by coupling a group Ar¹Ar²NH to Ar³ or L, for example by Ullmann or Hartwig-Buchwald coupling, or by coupling a group Ar¹Ar²—N—Ar³-G to L, for example by Suzuki coupling.

The reactive leaving group in step b) is preferably selected from Cl, Br, I, boronic acid or boronic acid derivatives, in particular boronic acid esters, triflate or tosylate.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the preparation of corresponding oligomers, dendrimers or polymers. The oligomerisation or polymerisation here is preferably carried out via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers comprising one or more of the compounds according to the invention mentioned above, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers, where the units of the formula (1) are present in a proportion of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also comprise further units, for example hole-transport units, in particular those based on triarylamines, and/or electron-transport units. In addition, the polymers can either comprise triplet emitters in copolymerised form or mixed in as a blend. Precisely the combination of units of the formula (1) with triplet emitters gives particularly good results.

Furthermore, the compounds of the formula (1) may also be functionalised further and thus converted into extended structures. An example which may be mentioned here is the reaction with arylboronic acids by the Suzuki method or with primary or secondary amines by the Hartwig-Buchwald method. Thus, the compounds of the formula (1) can also be bonded directly to phosphorescent metal complexes or also to other metal complexes.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds according to the invention mentioned above in an electronic device, in particular in an organic electroluminescent device.

The present invention again furthermore relates to an electronic device comprising at least one of the compounds according to the invention mentioned above. The preferences stated above likewise apply to the electronic devices.

The electronic device is preferably selected from the group consisting of organic electroluminescent devices (organic light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells (ODSSCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), but preferably organic electroluminescent devices (OLEDs), particularly preferably phosphorescent OLEDs.

The organic electroluminescent devices and the light-emitting electrochemical cells can be used for various applications, for example for monochromatic or polychromatic displays, for lighting applications or for medical or cosmetic applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present.

The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 05/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed in various layers, depending on the precise structure. Preference is given to an organic electroluminescent device comprising a compound of the formula (1) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a particularly preferred embodiment of the invention, the compound of the formula (1) is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state>1, in particular from an excited triplet state. For the purposes of this application, all luminescent complexes containing transition metals or lanthanoids, in particular all luminescent iridium, platinum and copper complexes, are to be regarded as phosphorescent compounds.

The mixture of the compound of the formula (1) and the emitting compound comprises between 99 and 1% by weight, preferably between 98 and 10% by weight, particularly preferably between 97 and 60% by weight, in particular between 95 and 80% by weight, of the compound of the formula (1), based on the entire mixture comprising emitter and matrix material. Correspondingly, the mixture comprises between 1 and 99% by weight, preferably between 2 and 90% by weight, particularly preferably between 3 and 40% by weight, in particular between 5 and 20% by weight, of the emitter, based on the entire mixture comprising emitter and matrix material.

A further preferred embodiment of the present invention is the use of the compound of the formula (1) as matrix material for a phosphorescent emitter in combination with a further matrix material. Particularly suitable matrix materials which can be employed in combination with the compounds of the formulae (1) are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP(N,N-biscarbazolylbiphenyl), m-CBP or the carbazole derivatives disclosed in WO 05/039246, US 2005/0069729, JP 2004/288381, EP 1205527 or WO 2008/086851, indolocarbazole derivatives, example in accordance with WO 2007/063754 or WO 2008/056746, indenocarbazole derivatives, for example in accordance with the unpublished applications DE 102009023155.2 or DE 102009031021.5, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with the unpublished application DE 102008036982.9, WO 2007/063754 or WO 2008/056746, zinc complexes, for example in accordance with EP 652273 or WO 2009/062578, fluorene derivatives, for example in accordance with WO 2009/124627, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779 or in accordance with the unpublished application DE 102009048791.3. It is furthermore possible to use an electronically neutral co-host which has neither hole-transporting nor electron-transporting properties, as described, for example, in WO 2010/108579.

It is likewise possible to use two or more phosphorescent emitters in the mixture. The emitter, which emits at relatively short wavelength, is used here as co-host in the mixture.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373, US 2005/0258742, WO 2009/146770, WO 2010/015307, WO 2010/031485, WO 2010/054731, WO 2010/054728, WO 2010/086089, WO 2010/099852 and WO 2010/102709. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent compounds are listed in the following table.

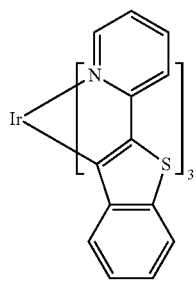

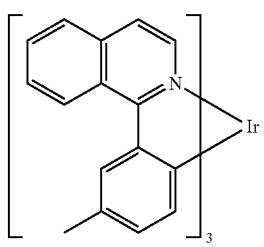

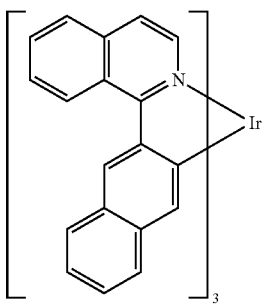

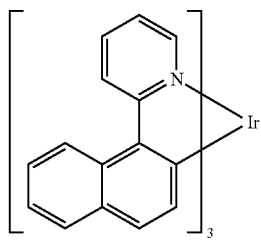

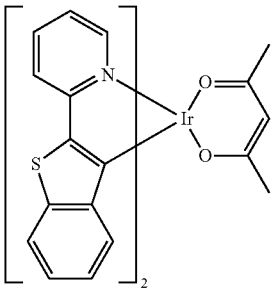

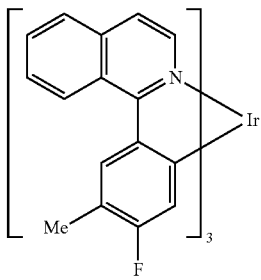

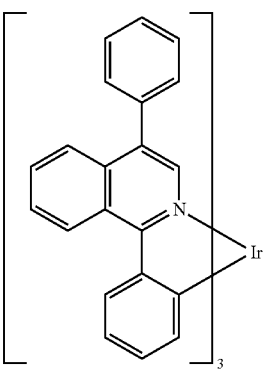

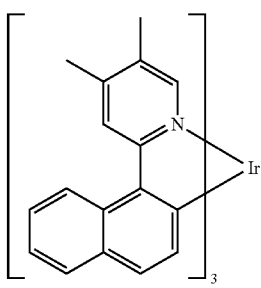

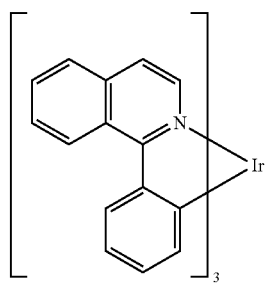
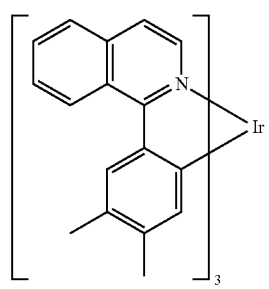
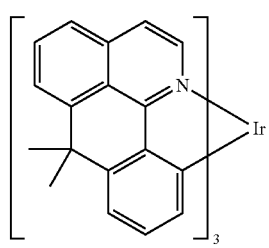
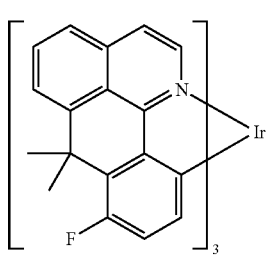
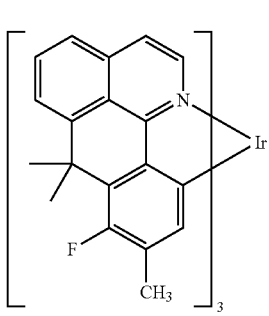
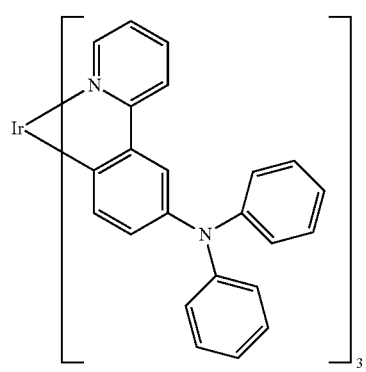
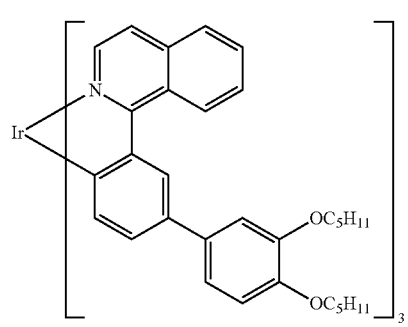
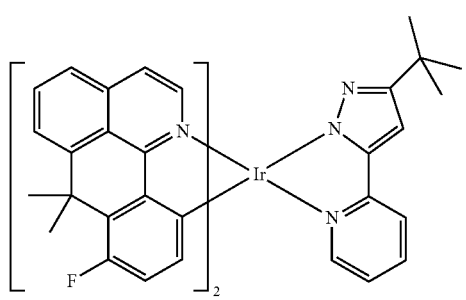
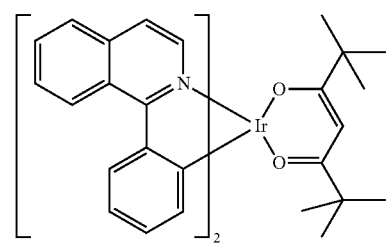
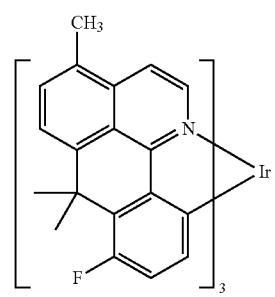

93
-continued
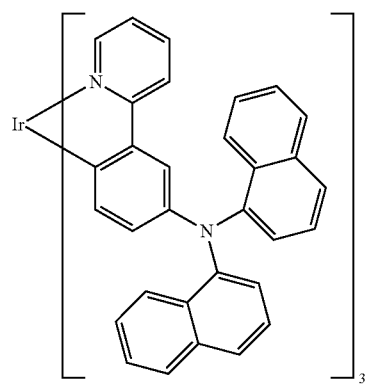
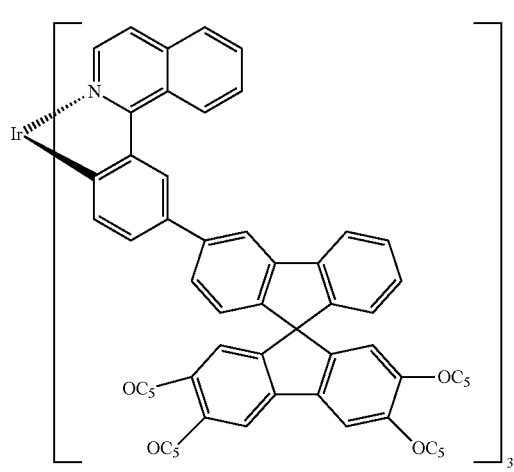
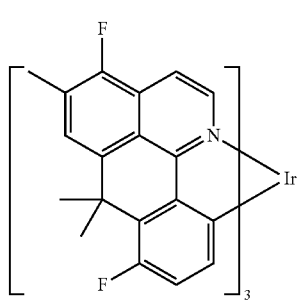
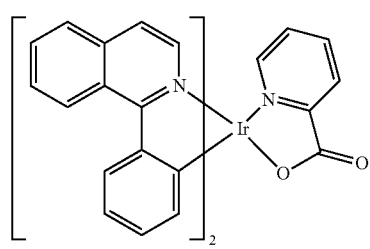
94
-continued
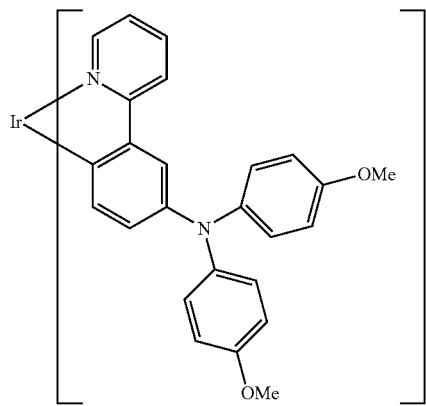
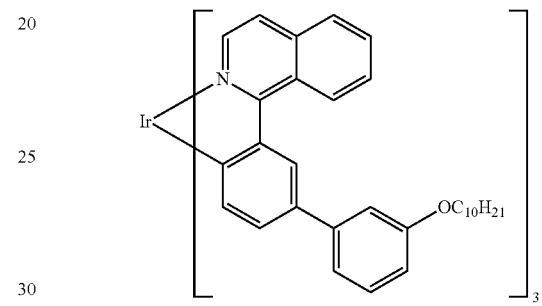
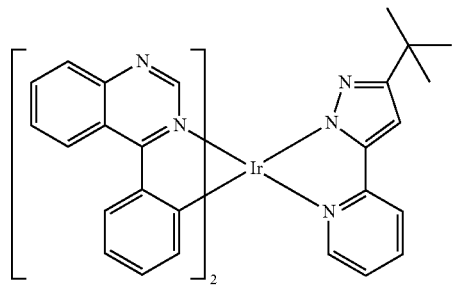
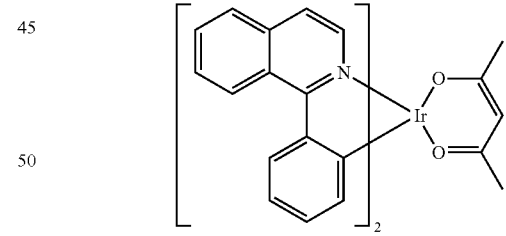
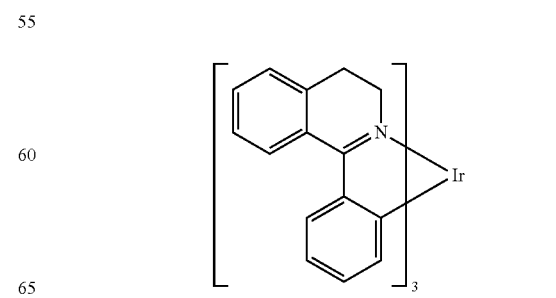

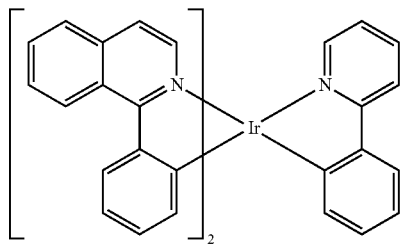
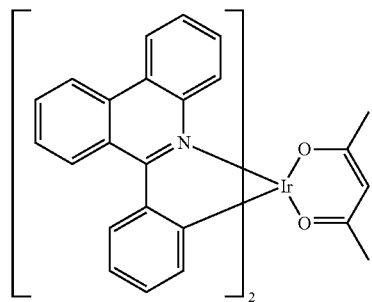
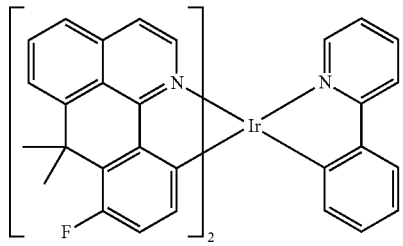
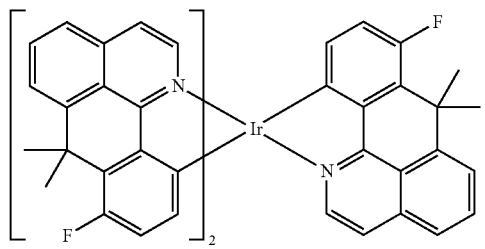
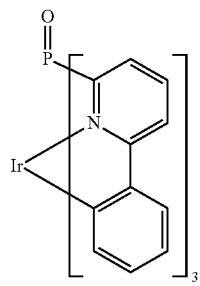
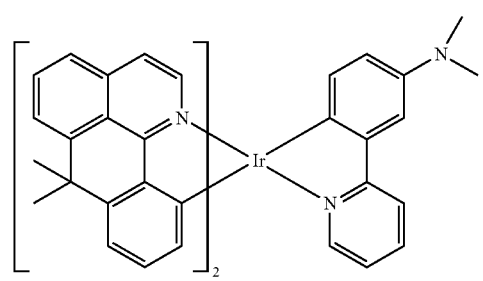
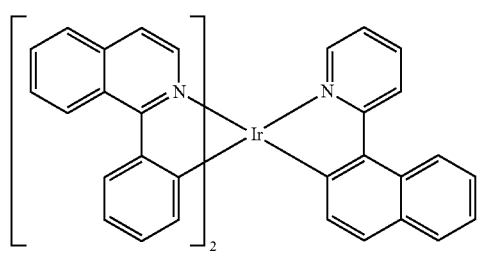
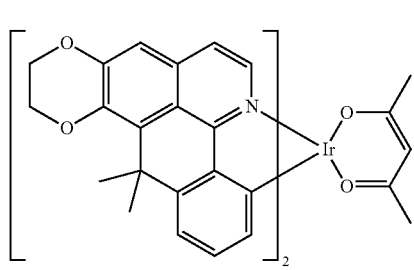
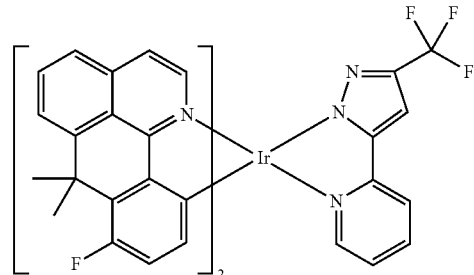
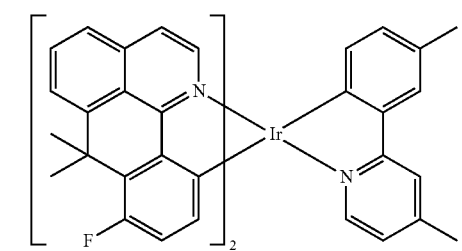
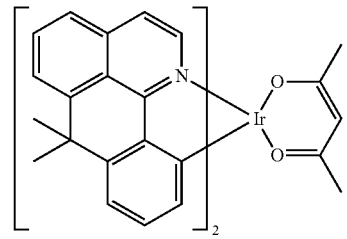
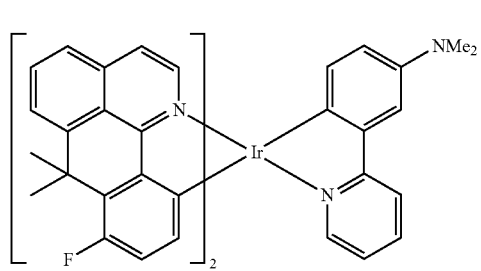

97
-continued
98
-continued
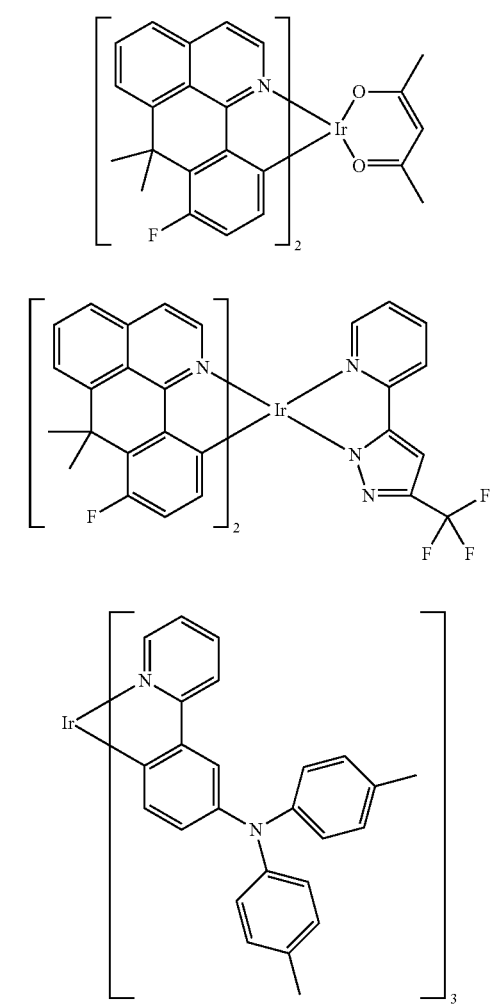
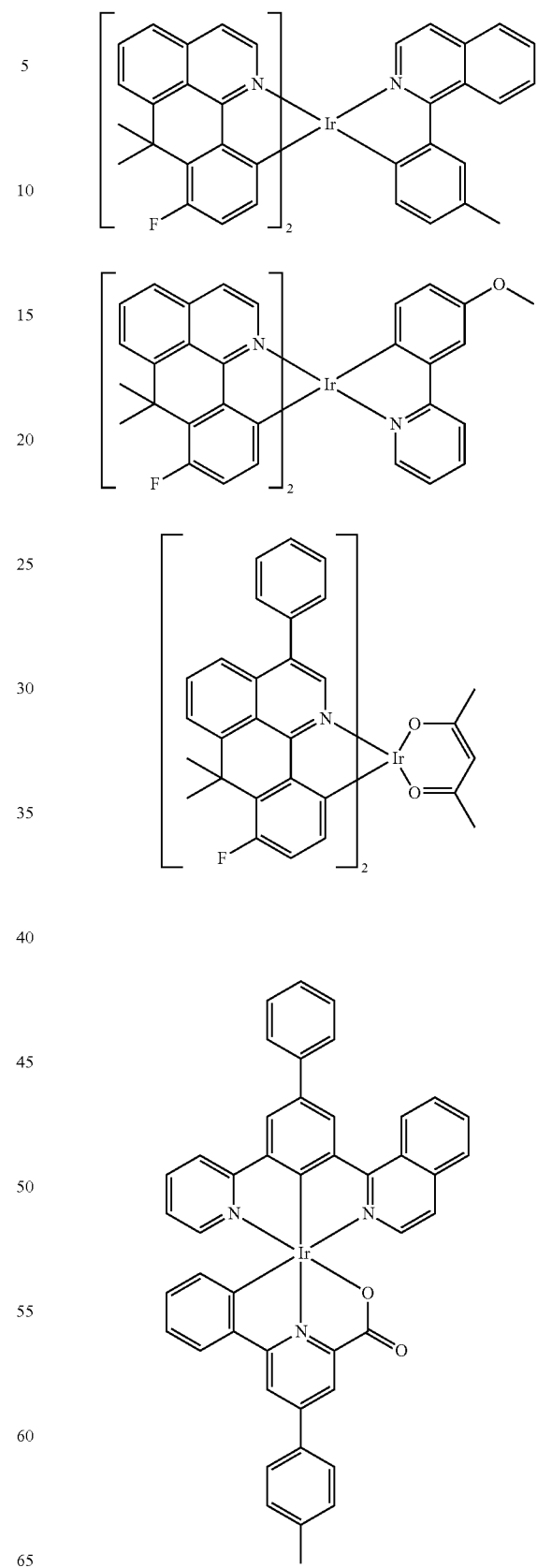

99
-continued
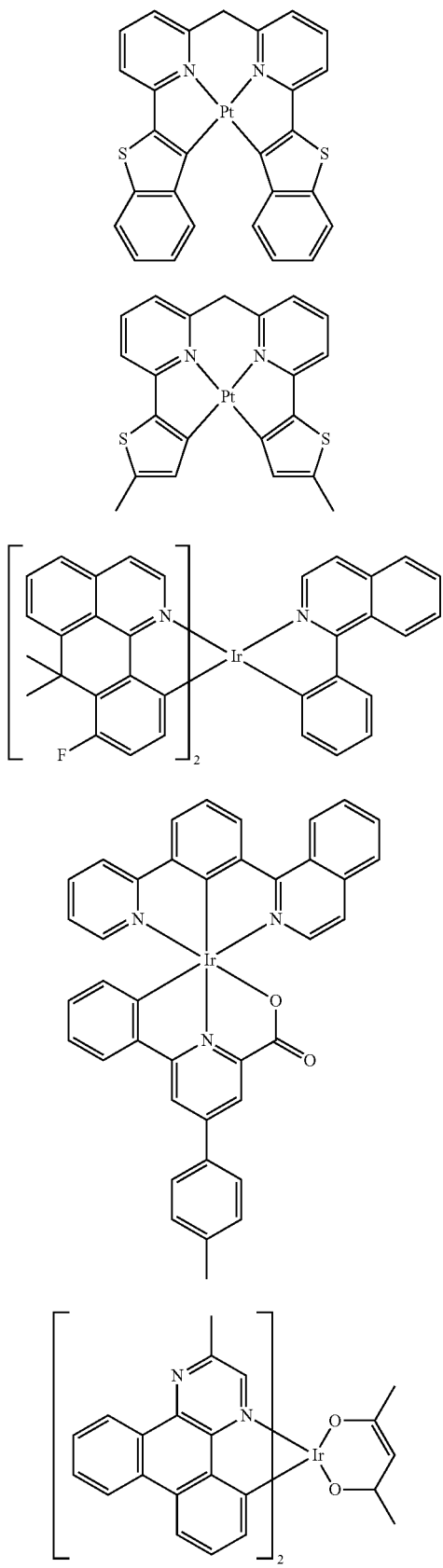
100
-continued
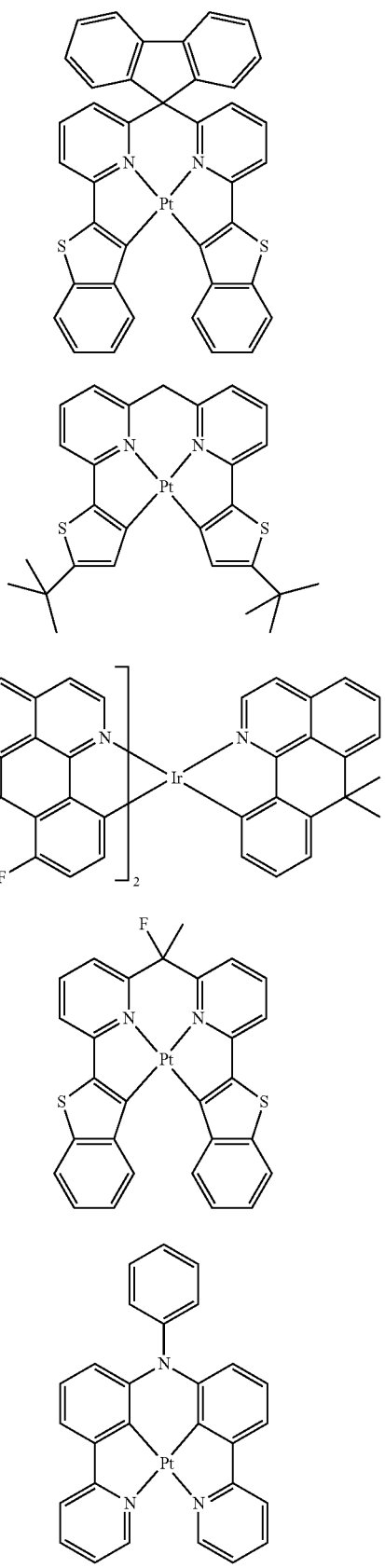

101
-continued
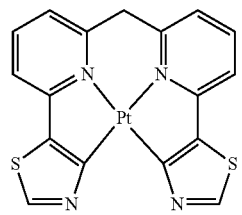
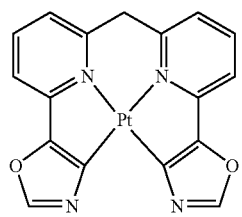
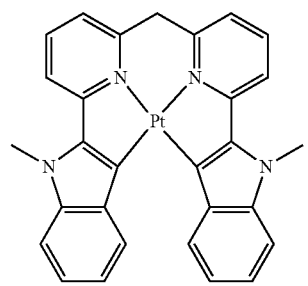
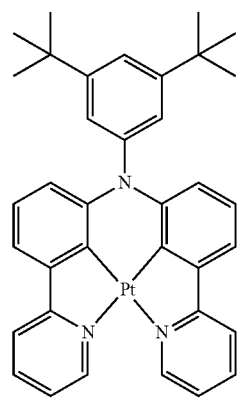
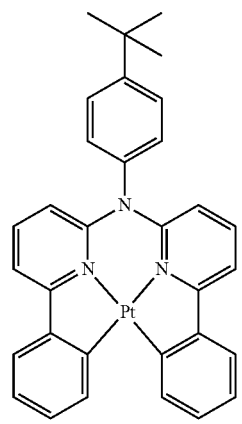
102
-continued
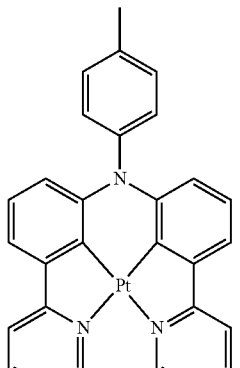
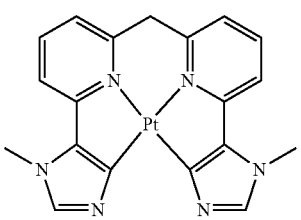
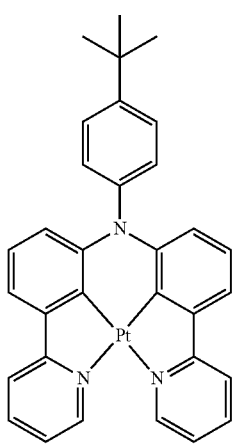
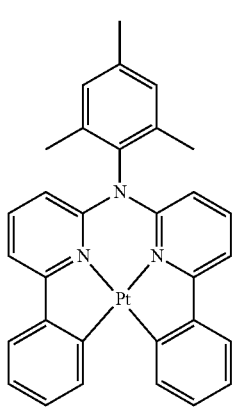

103
-continued
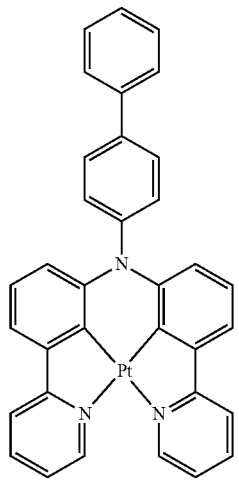
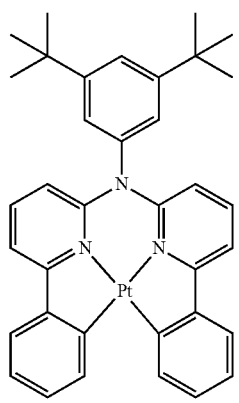
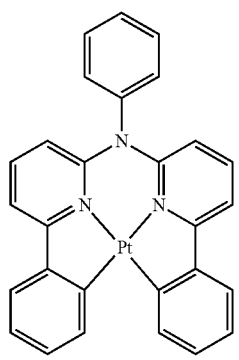
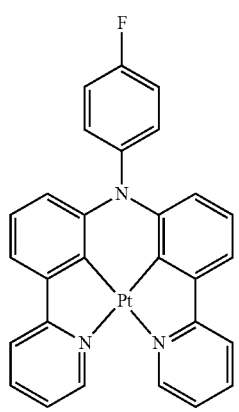
104
-continued
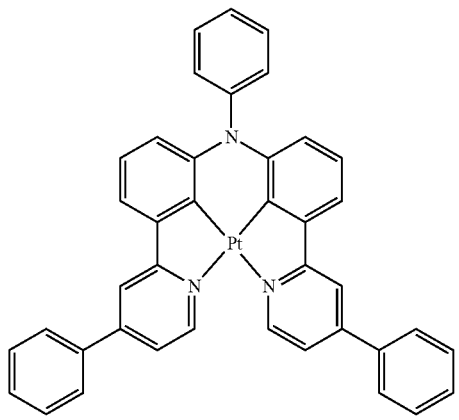
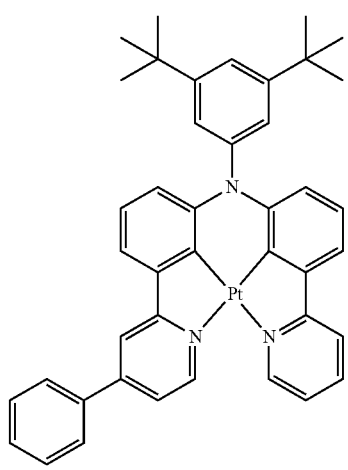
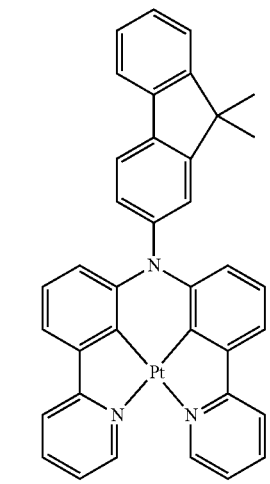

105
-continued
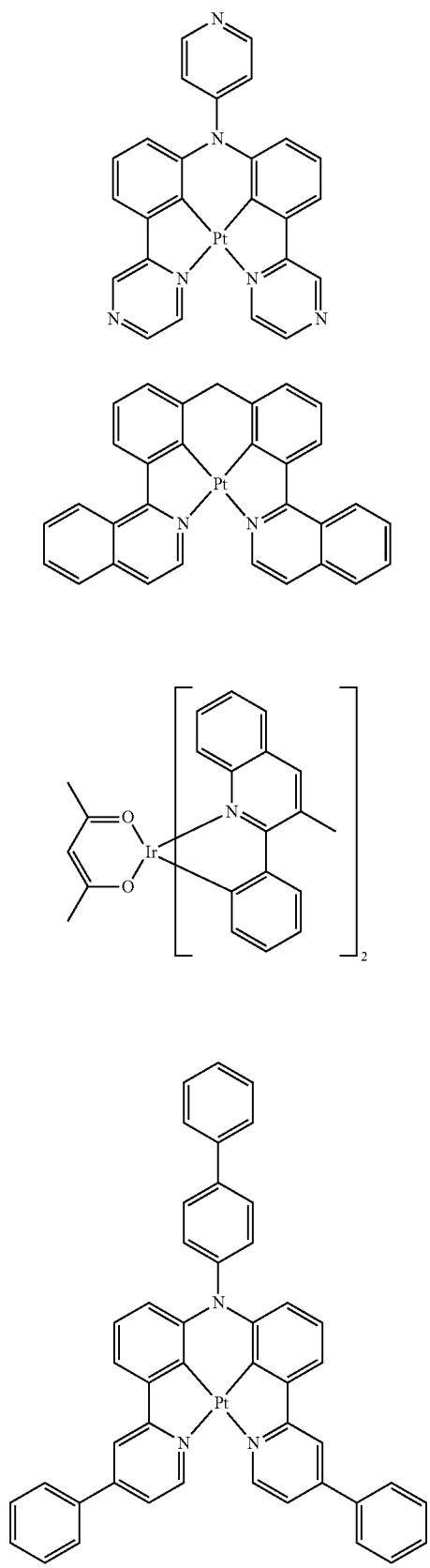
106
-continued
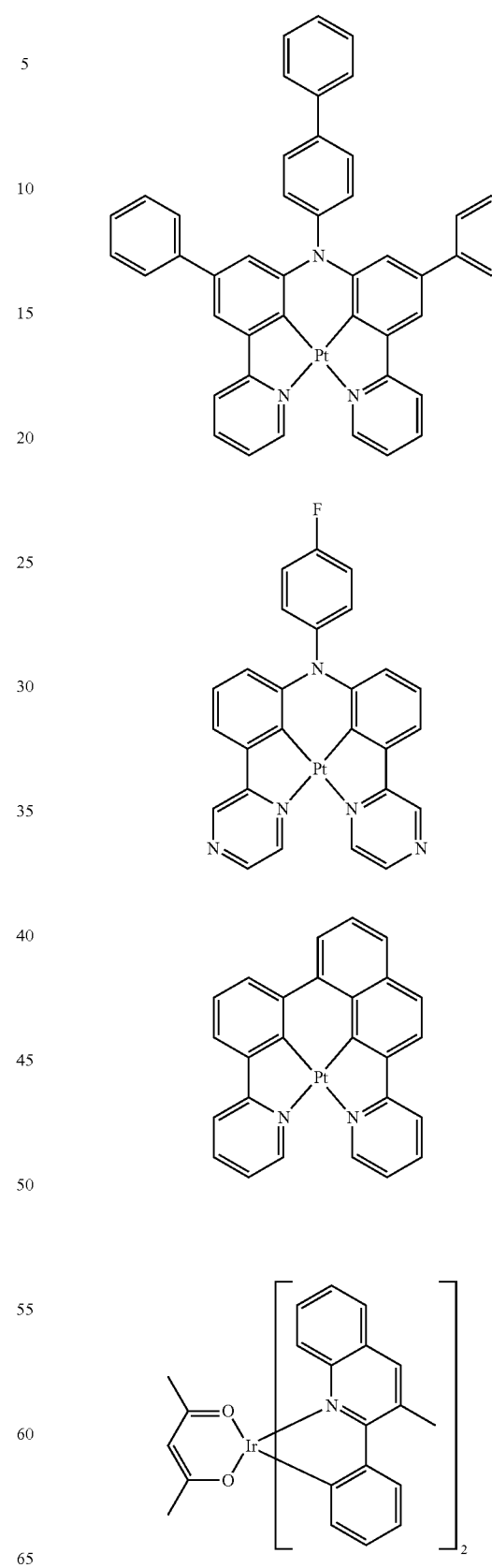

107
-continued
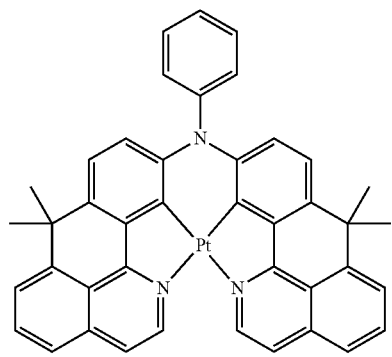
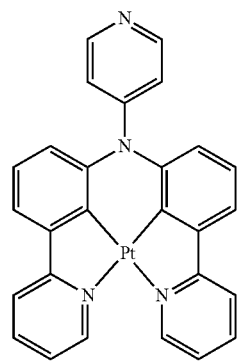
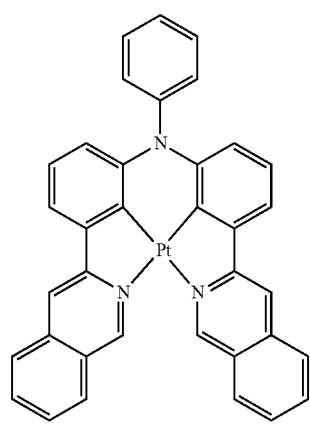
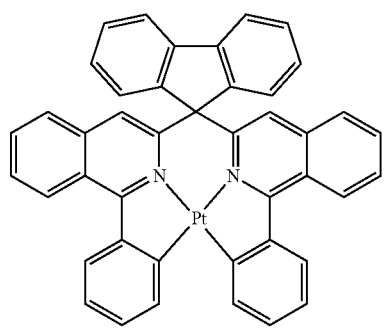
108
-continued
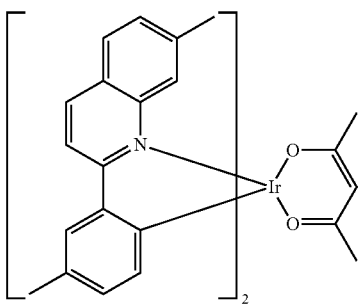
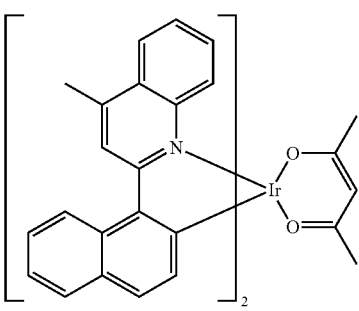
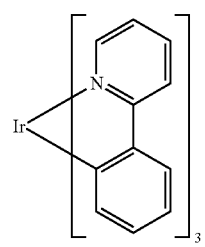
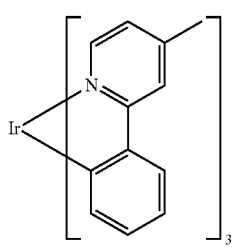
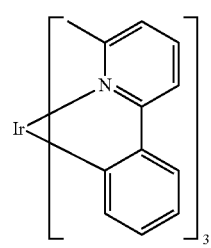

| 109 -continued | 110 -continued |
|---|---|
| 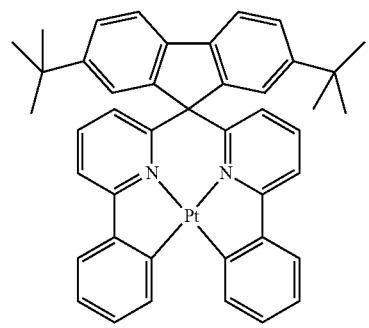<br><br>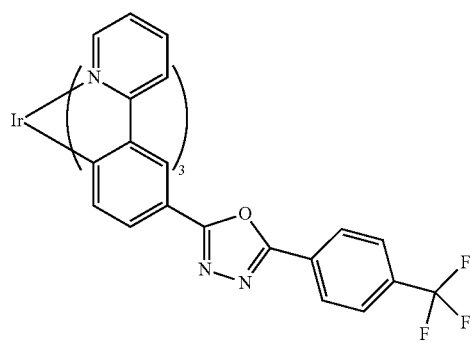<br><br>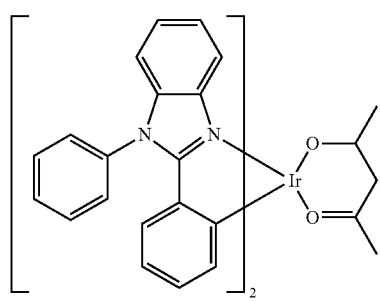<br><br>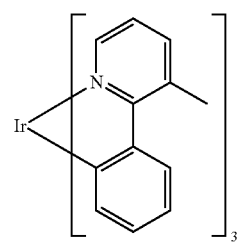<br><br>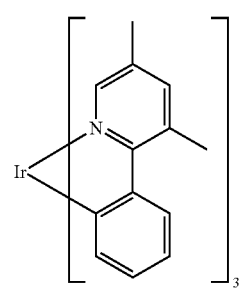 | 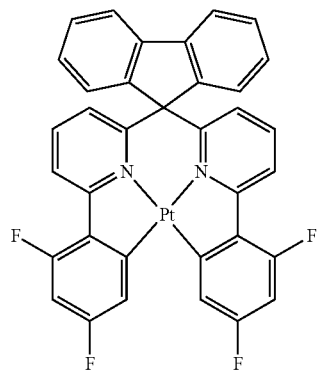<br><br>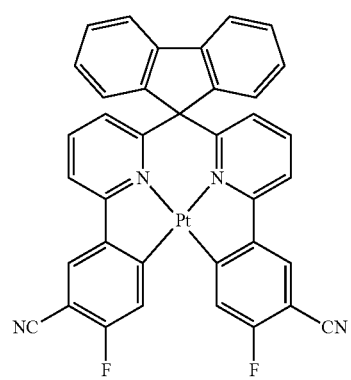<br><br>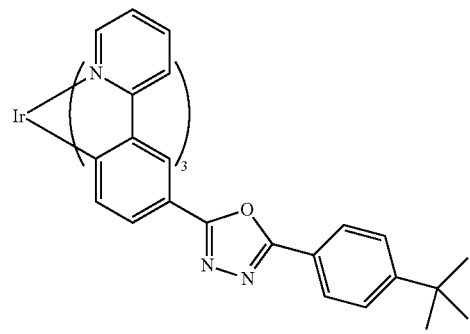<br><br>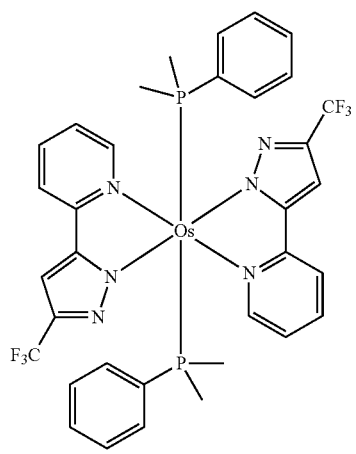 |

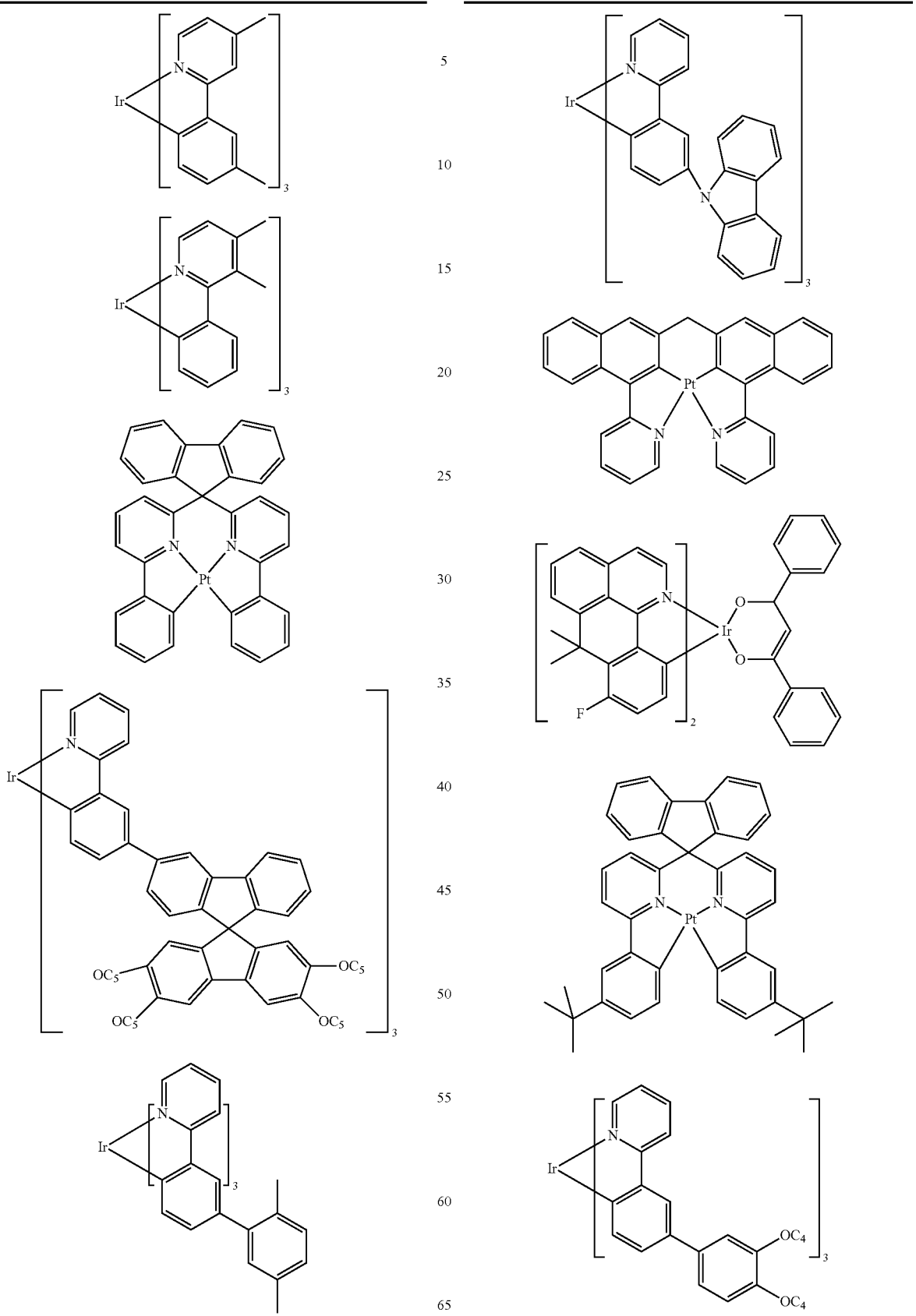

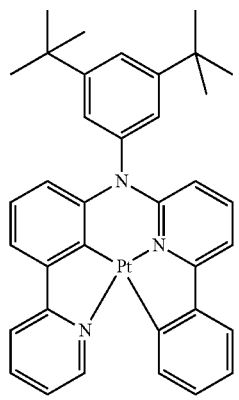
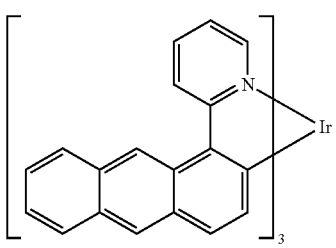
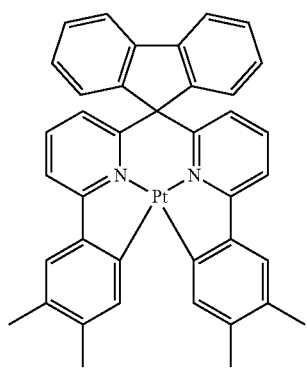
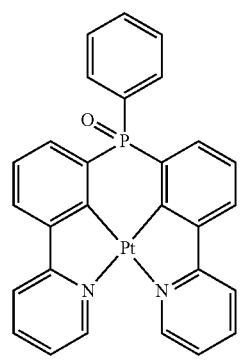
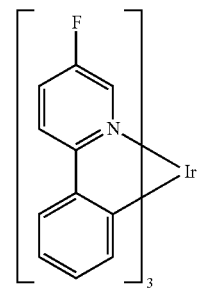
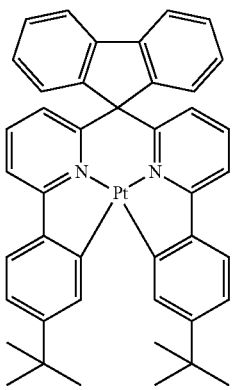
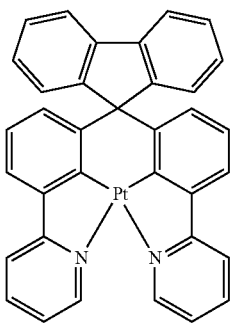
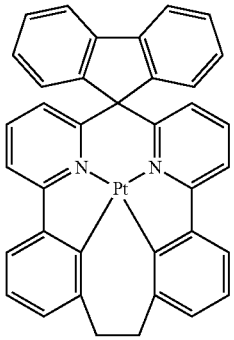

115
-continued
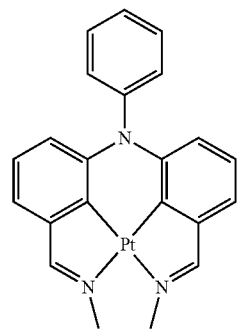
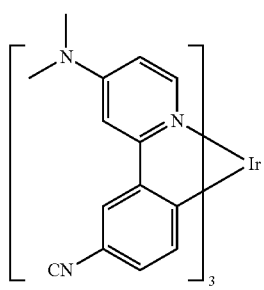
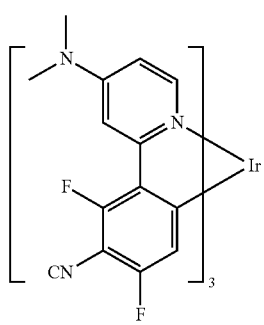
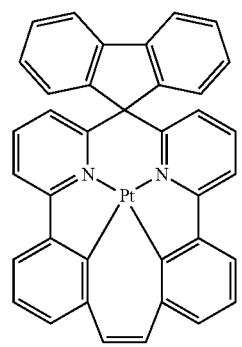
116
-continued
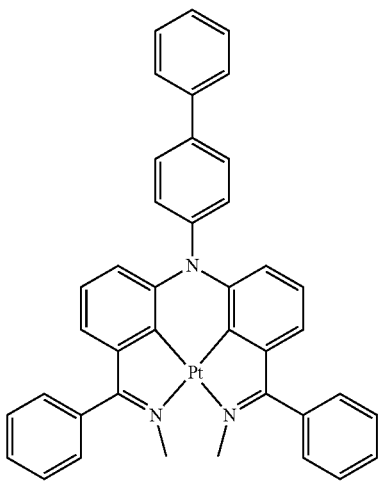
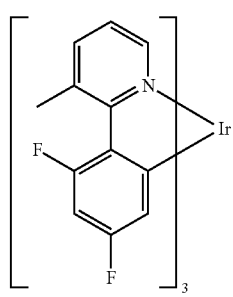
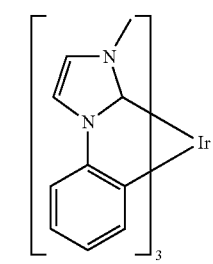
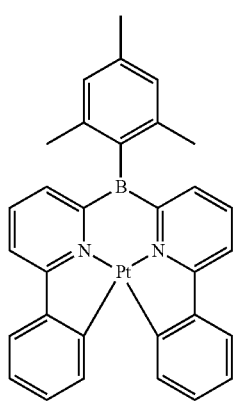

| 117 -continued | 118 -continued |
|---|---|
| 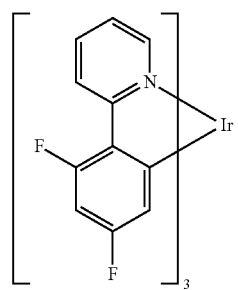 | 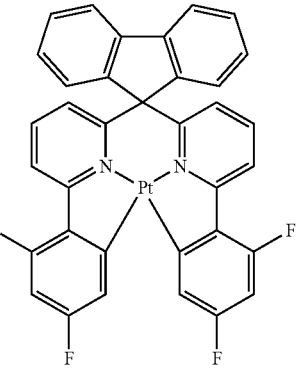 |
| 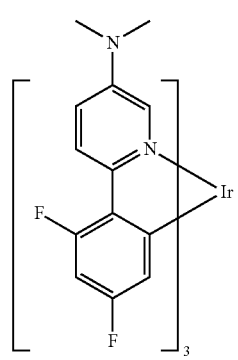 | 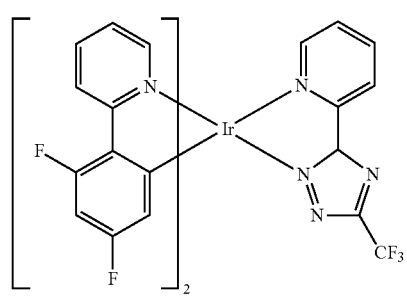 |
| 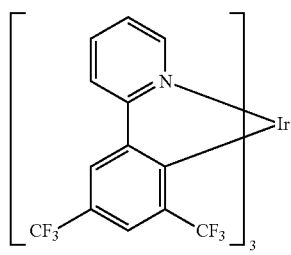 | 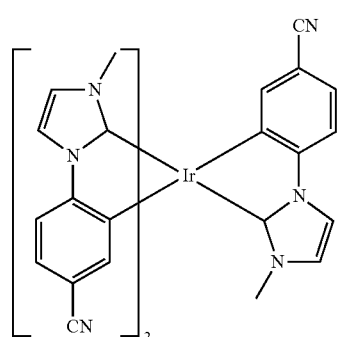 |
| 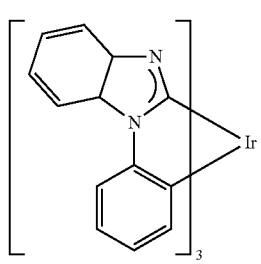 | 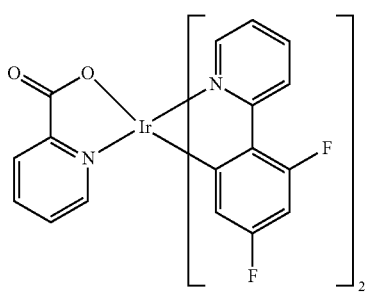 |
| 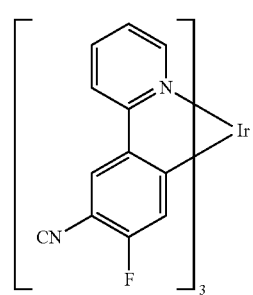 | 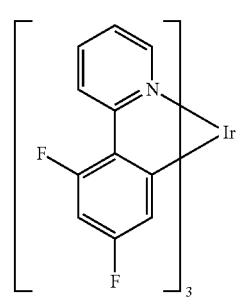 |

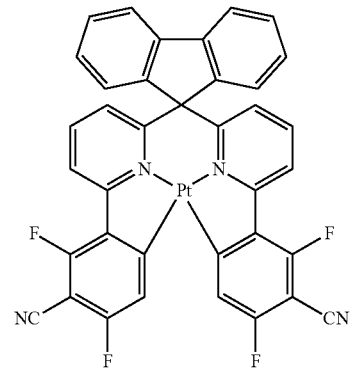

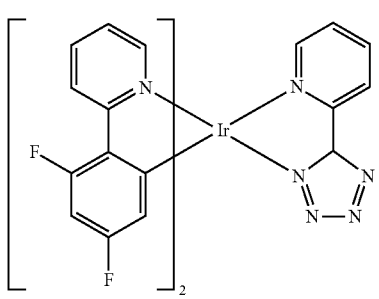

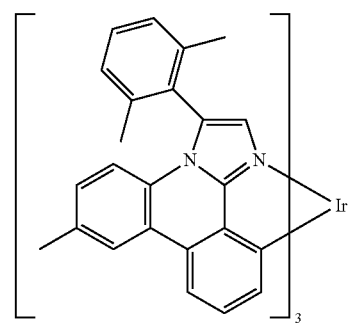

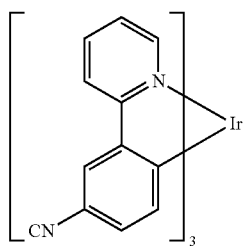

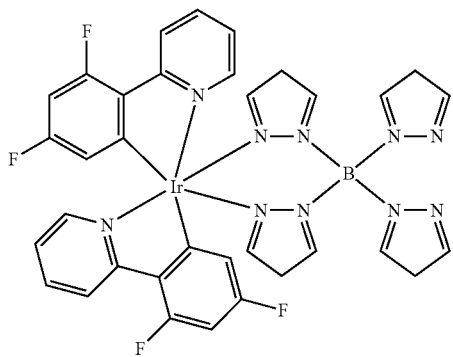

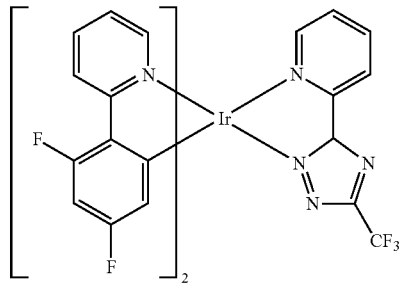

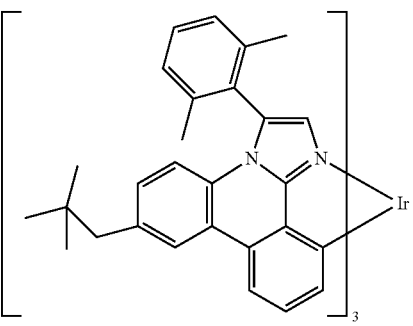

In a further embodiment of the invention, the organic electroluminescent device does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, Liq (lithium hydroxyquinolinate).

In yet a further preferred embodiment of the invention, the compound of the formula (1) is employed in a hole-blocking layer. A hole-blocking layer is taken to mean a layer which is directly adjacent to an emitting layer on the cathode side.

It is furthermore possible to use the compound of the formula (1) both in a hole-blocking layer or electron-transport layer and as matrix in an emitting layer.

In the further layers of the organic electroluminescent device according to the invention, it is possible to use all materials as usually employed in accordance with the prior art. The person skilled in the art will therefore be able, without an inventive step, to employ all materials known for organic electroluminescent devices in combination with the compounds of the formulae (1) according to the invention.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing), ink-jet printing, screen printing, flexographic printing or offset printing. Soluble compounds, which are obtained, for example, by suitable substitution, are necessary for this purpose. These processes are also suitable for oligomers, dendrimers and polymers. These processes are also particularly suitable for the compounds according to the invention, since they generally have very good solubility in organic solvents.

Also possible are hybrid processes, in which, for example, one or more layers are applied from solution and one or more further layers are applied by vapour deposition. Thus, for example, the emitting layer can be applied from solution and the electron-transport layer can be applied by vapour deposition.

These processes are generally known to the person skilled in the art and can be applied by him without inventive step to organic electroluminescent devices comprising the compounds according to the invention.

Formulations of the compounds according to the invention are necessary for the processing of the compounds according to the invention from the liquid phase, for example by spin coating or by printing processes. These formulations can be, for example, solutions, dispersions or mini emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, dispersion or mini emulsion, comprising at least one compound of the formula (1) or a corresponding oligomer, polymer or dendrimer according to the invention and at least one solvent, in particular an organic solvent. The way in which such solutions can be prepared is known to the person skilled in the art and is described, for example, in WO 2002/072714, WO 2003/019694 and the literature cited therein.

The present invention furthermore relates to mixtures comprising at least one compound of the formula (1) or a corresponding oligomer, polymer or dendrimer according to the invention and at least one further compound. The further compound can be, for example, a fluorescent or phosphorescent dopant if the compound according to the invention is used as matrix material. Suitable fluorescent and phosphorescent dopants are mentioned above in connection with the organic electroluminescent devices and are also preferred for the mixtures according to the invention.

The compounds according to the invention and the organic electroluminescent devices according to the invention are distinguished by the following surprising advantages over the prior art:

1. The compounds according to the invention or compounds of the formulae (1), employed as matrix material for fluorescent or phosphorescent emitters, result in very high efficiencies and long lifetimes. This applies, in particular, if the compounds are employed as matrix material for a phosphorescent emitter.
2. The compounds according to the invention or compounds of the formulae (1) are suitable not only as matrix for red- and green-phosphorescent compounds, but also for blue-phosphorescent compounds.
3. The compounds according to the invention or compounds of the formula (1) have a very small separation between the $S_1$ level, i.e. the first excited singlet level, and the $T_1$ level, i.e. the first excited triplet level, and are therefore particularly suitable for use as matrix in phosphorescent OLEDs.
4. The compounds according to the invention, employed in organic electroluminescent devices, result in high efficiencies and in steep current/voltage curves with low use and operating voltages.

These above-mentioned advantages are not accompanied by an impairment in the other electronic properties.

The invention is explained in greater detail by the following examples, without wishing to restrict it thereby. The person skilled in the art will be able to use the descriptions to carry out the invention throughout the range disclosed and to prepare further compounds according to the invention without inventive step and use them in electronic devices or use the process according to the invention.

EXAMPLES

The following syntheses are carried out under a protective-gas atmosphere in dried solvents, unless indicated otherwise.

Example 1

Synthesis of TMM2

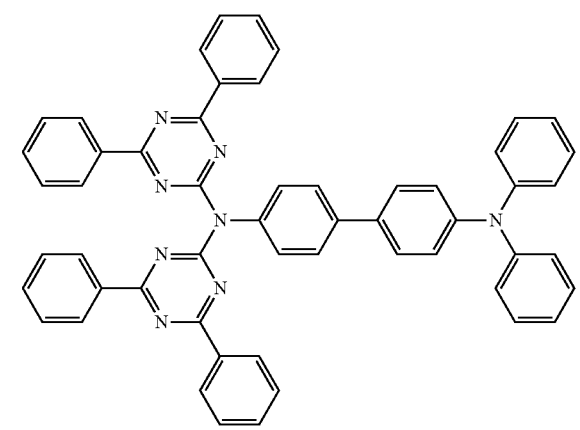 [SMILES: c1ccc(-c2nc(-c3ccccc3)nc(N(c3ccc(-c4ccc(N(c5ccccc5)c5ccccc5)cc4)cc3)c3nc(-c4ccccc4)nc(-c4ccccc4)n3)n2)cc1]

a) (4-Bromophenyl)-(4,6-diphenyl-1,3,5-triazin-2-yl)amine

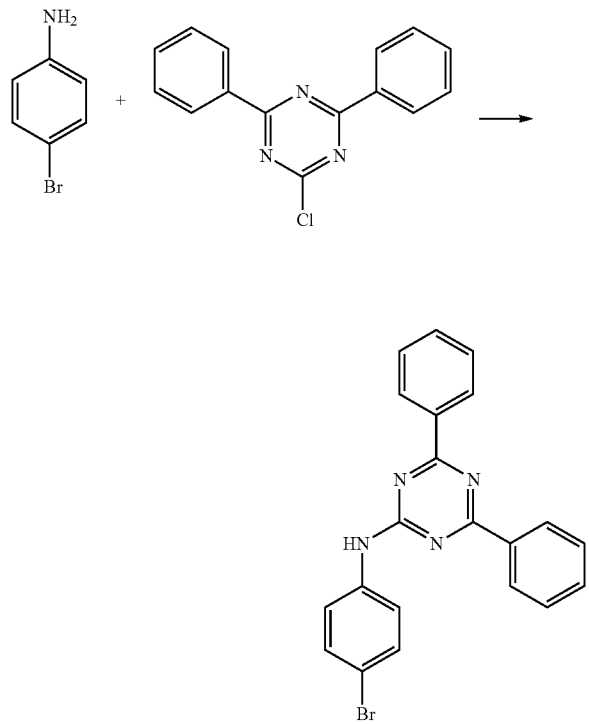

23.4 g (87.2 mmol) of 2-chloro-4,6-diphenyl-1,3,5-triazine in 400 ml of toluene are added to a well-stirred solution of 15.0 g (87.2 mmol) of 4-bromoaniline in 280 ml of pyridine and 400 ml of toluene, and the mixture is subsequently stirred at room temperature for 16 h. The solvent is subsequently removed in vacuo, and the residue is purified by chromatography (heptane/ethyl acetate 20:1). Yield: 21.1 g (52.3 mmol), 60%.

b) (4-Bromophenyl)bis-(4,6-diphenyl-1,3,5-triazin-2-yl)amine

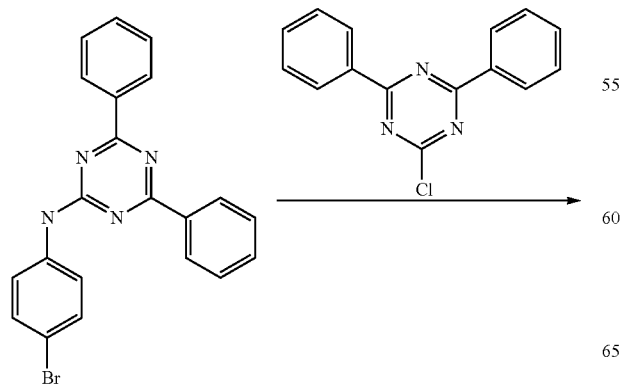

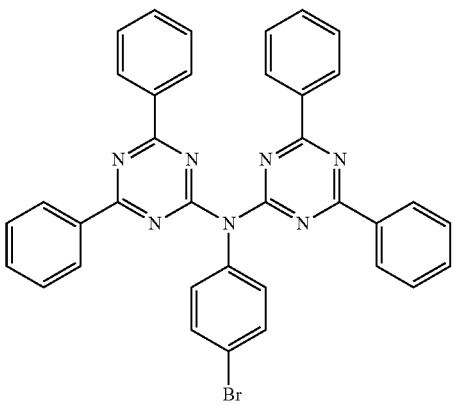

0.32 g (8 mmol) of NaH (60% in oil) is initially introduced in 100 ml of THF. A solution of 2.00 g (5 mmol) of the product from a) in 50 ml of THF is added dropwise at room temperature. After 1 h, 1.35 g (5 mmol) of 2-chloro-4,6-diphenyl-1,3,5-triazine are added, the mixture is heated under reflux for 8 h and stirred at RT for 12 h. The solvent is subsequently removed in vacuo, and the residue is purified by chromatography (heptane/ethyl acetate 20:1). Yield: 0.71 g (1.2 mmol), 22%.

c) TMM2

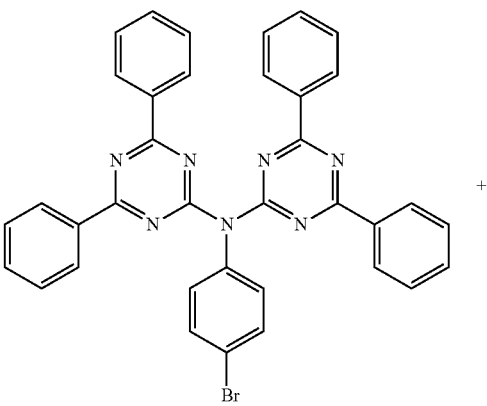

+

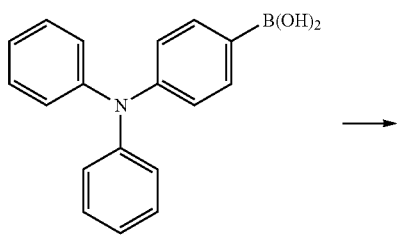

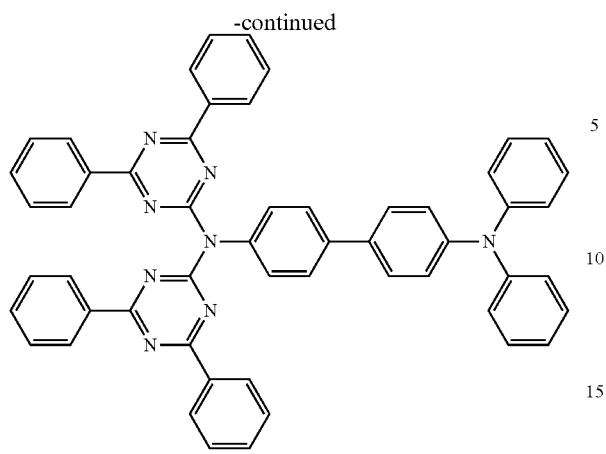

0.95 g (1.5 mmol) of the product from b), 0.45 g (1.7 mmol) of 4-diphenylaminophenylboronic acid and 0.81 g (3.75 mmol) of tripotassium phosphate are suspended in 50 ml of toluene, 50 ml of dioxane and 50 ml of water. 45.6 mg (0.15 mmol) of tri-o-tolylphosphine and then 17 mg (0.075 mmol) of palladium(II) acetate are added to this suspension, and the reaction mixture is heated under reflux for 16 h. After cooling, the organic phase is separated off, filtered through silica gel, washed three times with 20 ml of water each time and subsequently evaporated to dryness. The residue is recrystallised from toluene and from dichloromethane/isopropanol. The yield is 0.59 g (0.74 mmol), corresponding to 49% of theory.

Example 2

Synthesis of TMM3

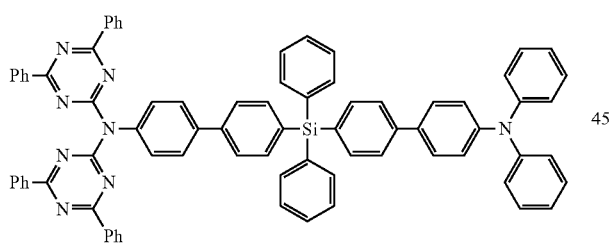

a) Bis(4-bromophenyl)diphenylsilane

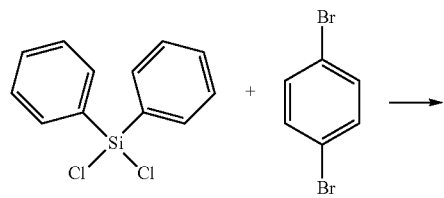

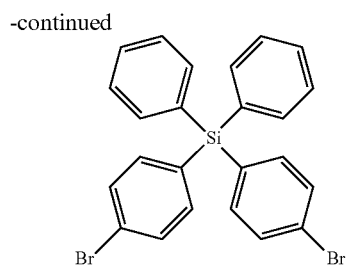

10.81 g (50 mmol) of 1,4-dibromobenzene are dissolved in 400 ml of dry THF and cooled to −78° C. 20 ml (50 mmol) of n-butyllithium are subsequently added dropwise at −78° C., and, when the addition is complete, the mixture is stirred at 78° C. for a further 1 h. 6.3 g (25 mmol) of dichlorodiphenylsilane, dissolved in 80 ml of dry THF, are then slowly added dropwise and allowed to come to room temperature overnight. The reaction mixture is evaporated to dryness in a rotary evaporator, and the solid is recrystallised from toluene and then from n-butanol. The yield is 10 g (0.21 mmol), corresponding to 81% of theory.

b) 2,2'-[(Diphenylsilylene)di-1,4-phenylene]bis(4,4,5,5-tetramethyl-1,3,2-dioxaborolane)

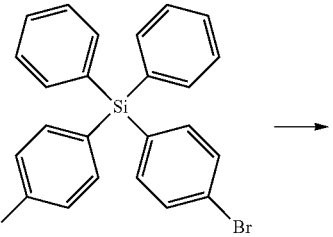

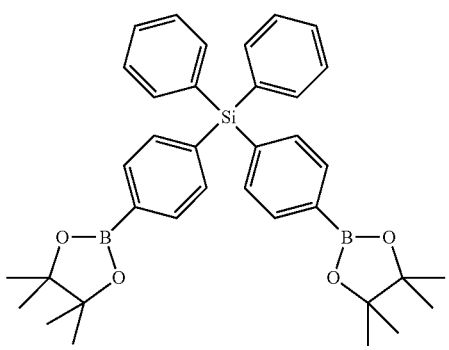

A mixture of bis(4-bromophenyl)diphenylsilane (28.2 g, 57 mmol), bis(pinacolato)diboron (16.0 g, 63 mmol), potassium acetate (18.6 g, 0.19 mol), $PdCl_2(dppf) \times CH_2Cl_2$ (0.75 g, 1 mmol) and dioxane (400 ml) is degassed for 30 min. The reaction mixture is heated under reflux for 6 h. After cooling to room temperature, the mixture is poured into ice-water (80 ml) and extracted with toluene. The combined organic phases are dried over sodium sulfate, and the solvent is distilled off under reduced pressure, leaving a brown liquid. The end product is isolated as pale-brown solid (30.2 g, 90%).

c) TMM3

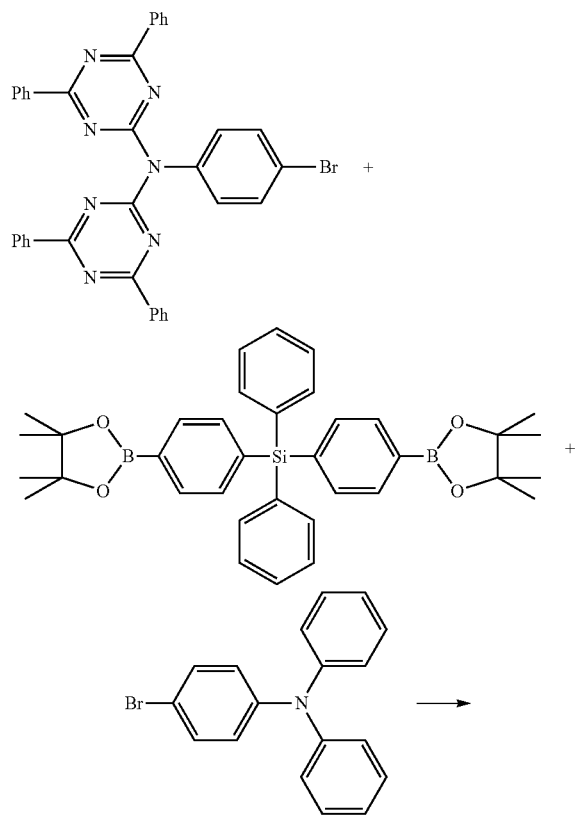

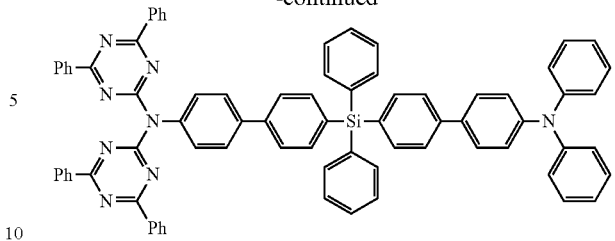

A mixture of 13.18 g (22.4 mmol) of 2'-[(diphenylsilylene)di-1,4-phenylene]-bis(4,4,5,5-tetramethyl-1,3,2-dioxaborolane), 7.2 g (11.2 mmol) of (4-bromophenyl)bis(4,6-diphenyl-1,3,5-triazin-2-yl)amine and 3.9 g (11.7 mmol) of (4-bromophenyl)diphenylamine in 250 ml of toluene and 250 ml of dioxane is degassed by passing-through of $N_2$ for 30 min. 252 mg (1.12 mmol) of $Pd(OAc)_2$ and 1.34 g (4.48 mmol) of tris-o-tolylphosphine are then added, and the mixture is heated at 80° C. for 8 h. After cooling to room temperature, the mixture is diluted with 100 ml of water and extracted with ethyl acetate (3×50 ml). The combined organic phases are dried over sodium sulfate, and the solvent is removed under reduced pressure. The crude product is purified by flash chromatography over silica and crystallisation (17 g, 67%).

Example 3

Synthesis of TMM4

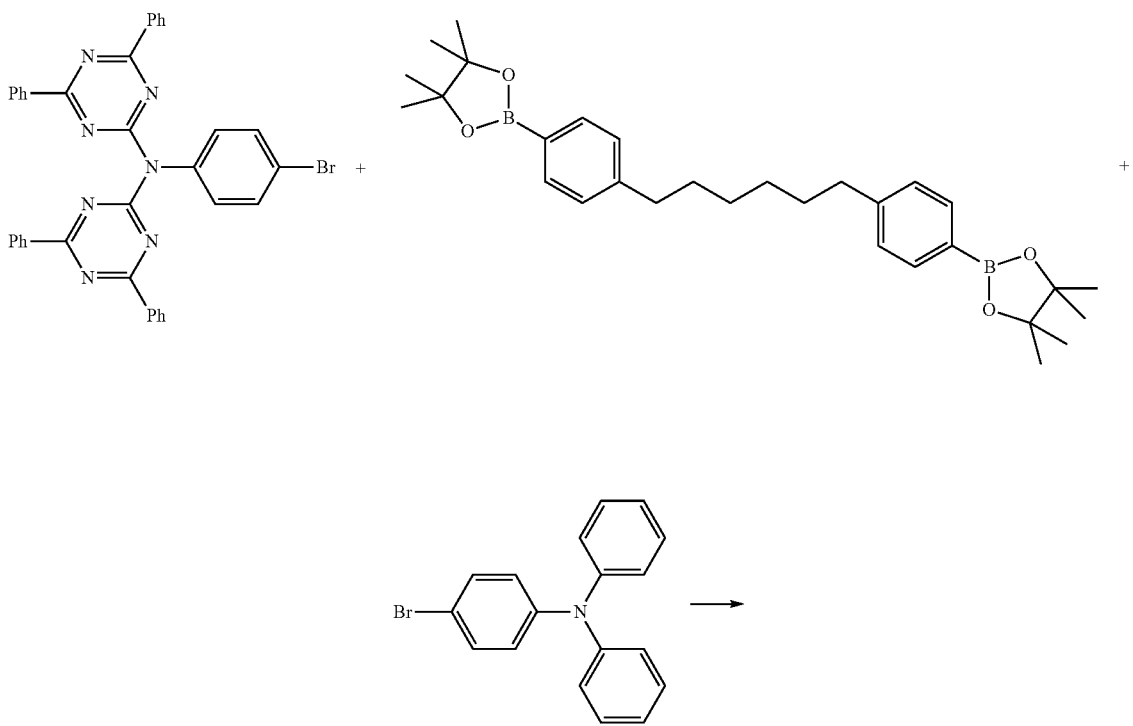

-continued

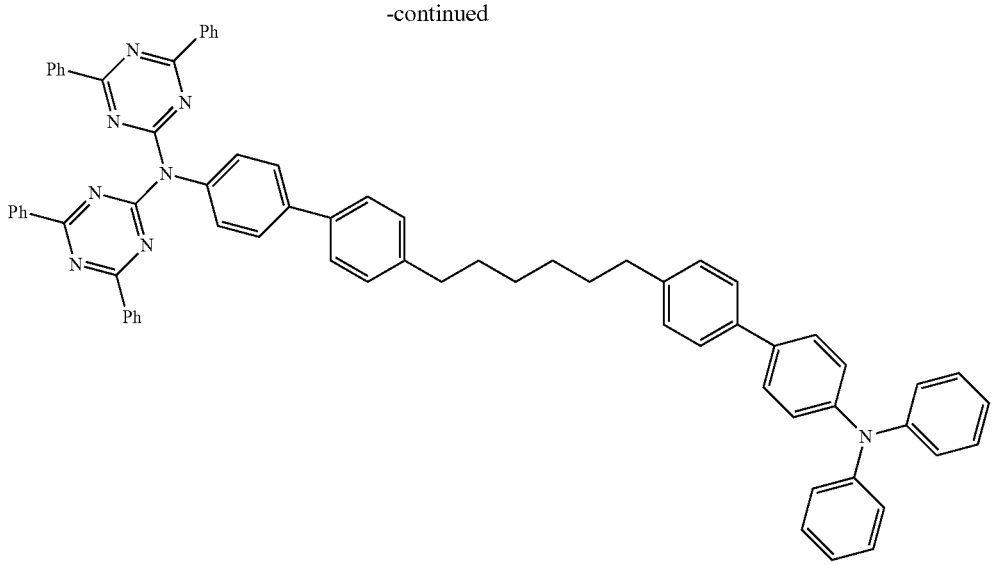

A mixture of 1,6-bis(p-bis[4,4,5,5-tetramethyl-1,3,2-dioxaborolane]phenyl)hexane (11 g, 22.4 mmol), (4-bromophenyl)bis-(4,6-diphenyl-1,3,5-triazin-2-yl)amine (7.2 g, 11.2 mmol) and (4-bromophenyl)diphenylamine (3.9 g, 11.7 mmol) in 250 ml of toluene and 250 ml of dioxane is degassed using $N_2$ for 30 min. $Pd(OAc)_2$ (252 mg, 1.12 mmol) and tris-o-tolylphosphine (1.34 g, 4.48 mmol) is then added, and the mixture is heated at 80° C. for 24 h. After cooling to room temperature, the mixture is diluted with 100 ml of water and extracted with ethyl acetate (3×50 ml). The combined organic phases are dried over sodium sulfate, and the solvent is removed under reduced pressure. The crude product is purified by flash chromatography over silica and crystallisation (15 g, 64%).

Use Examples

Materials Used

The following materials are used in the present invention: TMM1 is a reference matrix material in accordance with the prior art (WO 2008/086851). TMM2, TMM3 and TMM4 are matrix materials according to the invention, the syntheses of which are described in Examples 1 to 3. The abbreviation TMM here stands for triplet matrix material. TEG1 is a phosphorescent emitter, where TEG stands for triplet emitter green.

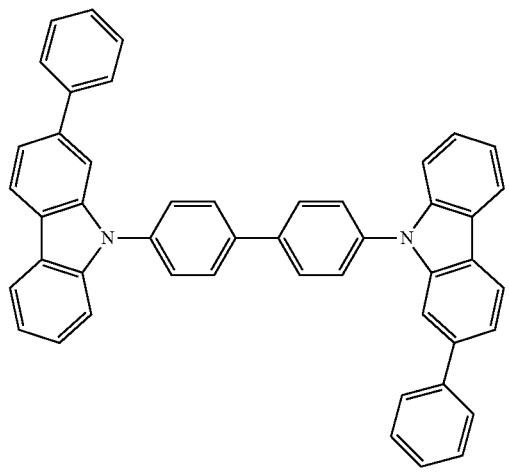

TMM1

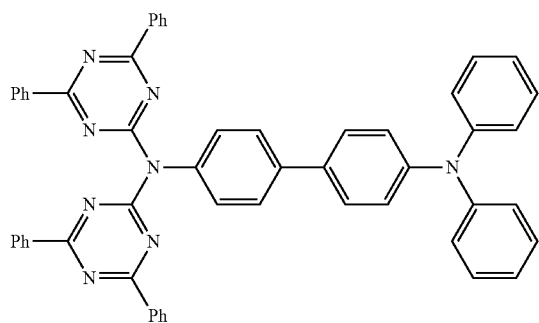
TMM2
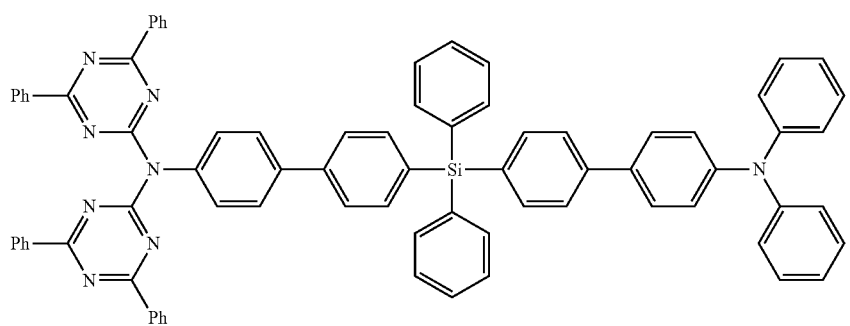
TMM3
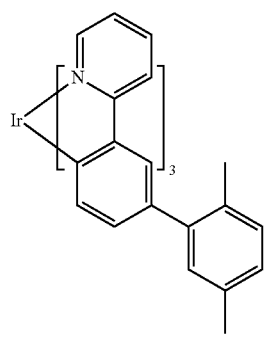
TEG1
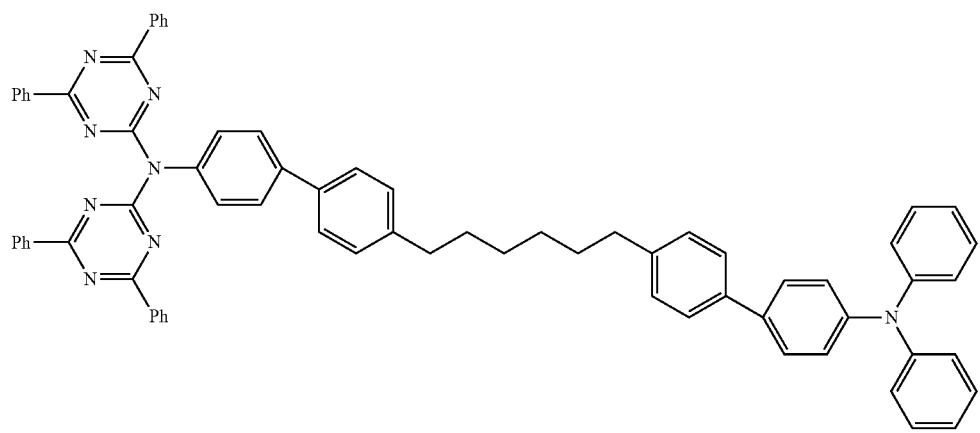
TMM4

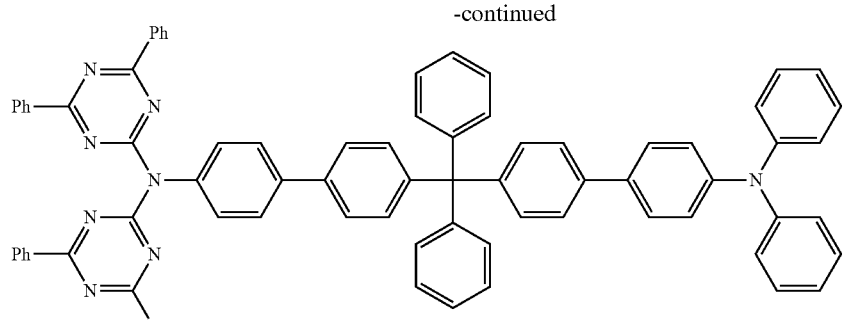

TMM5

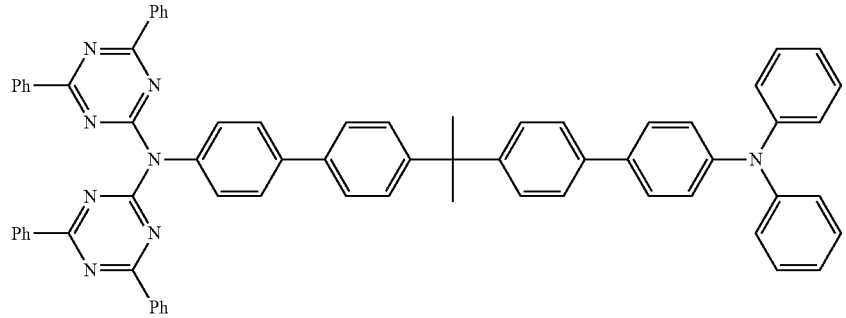

TMM6

Polymer IL1, which is used as interlayer, is a copolymer of the following monomers, which is synthesised by Suzuki coupling, as disclosed in WO 2003/048225:

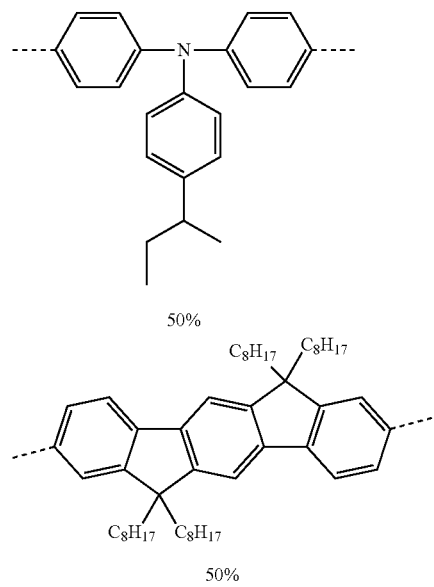

Example 4

Measurement of the Triplet Level and Quantum-Chemical Simulations for TMM1 to TMM6 and TEG1

The quantum-chemical simulations for TMM1 to TMM6 and TEG1 are carried out in Gaussian 03W (Gaussian Inc.): firstly, AM1 is used in order to optimise the molecular geometry, and TD-DFT (time-dependent density function theory) with correction functional B3PW9 and base set 6-31 G(d) is used for the energy calculation, which include the positions of HOMO and LUMO and the energies of the triplet state and the excited singlet state. The first triplet state and the first excited singlet state are the most important states. These are denoted below by T1 and S1. The HOMO and LUMO values are corrected by cyclic voltammetry (CV) as follows: a series of materials are measured by CV and also calculated by Gaussian 03W using the same method, for example using B3PW91 and the same base set 6-31G(d). The calculated values are then calibrated in accordance with the measured values. This calibration factor is used for the further calculations.

The T1 levels of TMM1 to TMM4 are furthermore measured by time-resolved spectroscopy at low temperature as follows: a film of TMM1 to TMM4 is coated onto quartz in a thickness of 100 nm and then excited using a YAG laser (355 nm) or an $N_2$ laser (337 nm) at liquid-helium temperature (10 K). The delayed photoluminescence spectrum after 10 μs is recorded. The T1 level is then determined by the onset of delayed photoluminescence.

The simulated and measured energy levels are summarised in Table 1. The T1 level of TEG1 is derived from the onset of the photoluminescence spectrum of TEG1 in toluene. The T1 levels of TMM1 to TMM6, both the simulated and calculated values, are higher than those of TEG1, which indicates that all these materials are suitable matrix materials for TEG1.

However, the reference matrix TMM1 has a large band separation and a large S1-T1 gap (about 0.43 eV), which can result in difficulties with charge injection. TMM2 to TMM6 have a much smaller S1-T1 separation (only about 0.2 eV), and their HOMO and LUMO levels are more suitable for charge injection.

TABLE 1

Summary of the energy levels of TMM1 to TMM6 and TEG1

| | TD-DFT | | | | Measured |
|---|---|---|---|---|---|
| | Homo Corr. [eV] | Lumo Corr. [eV] | T1 [eV] | S1 [eV] | T1 [eV] |
| TMM1 | −5.69 | −2.39 | 2.85 | 3.28 | 2.82 |
| TMM2 | −5.37 | −2.75 | 2.70 | 2.94 | 2.73 |
| TMM3 | −5.33 | −2.80 | 2.72 | 2.95 | 2.71 |
| TMM4 | −5.28 | −2.79 | 2.75 | 2.96 | 2.72 |
| TMM5 | −5.29 | −2.79 | 2.71 | 2.92 | |
| TMM6 | −5.29 | −7.28 | 2.74 | 2.92 | |
| TEG1 | −5.33 | −2.41 | 2.68 | 2.91 | 2.52 |

Example 5

Solutions and Compositions Comprising TMM1 to TMM4 and TEG1

Solutions as summarised in Table 2 are prepared as follows: firstly, 200 mg of the TMM and 50 mg of TEG1 are dissolved in 10 ml of chlorobenzene and stirred until the solution is clear. The solution is filtered using a Millipore Millex LS, hydrophobic PTFE 5.0 μm filter.

TABLE 2

Composition of the solutions

| | Composition | Ratio (based on weight) | Solvent | Concentration |
|---|---|---|---|---|
| Solution 1 | TMM1 + TEG1 | 75%:25% | chlorobenzene | 25 mg/ml |
| Solution 2 | TMM2 + TEG1 | 75%:25% | chlorobenzene | 25 mg/ml |
| Solution 3 | TMM3 + TEG1 | 75%:25% | chlorobenzene | 25 mg/ml |
| Solution 4 | TMM4 + TEG1 | 75%:25% | chlorobenzene | 25 mg/ml |

Solutions 1 to 4 are used to coat the emitting layer of OLEDs. The corresponding solid composition can be obtained by evaporating the solvent from the solutions. This can be used for the preparation of further formulations.

Example 6

Production of OLEDs

OLED1 to OLED4 having a structure in accordance with the prior art, as depicted in FIG. 1, are produced using the corresponding solutions, as summarised in Table 2, in accordance with the following procedure:

1) Coating of 80 nm of PEDOT (Baytron P AI4083) onto an ITO-coated glass substrate by spin coating.
2) Coating of a 20 nm interlayer IL1 by spin coating a toluene solution of IL1 (concentration 0.5% by weight) in a glove box.
3) Heating of the interlayer IL1 at 180° C. for 1 h in a glove box.
4) Coating of an 80 nm emitting layer by spin coating of a solution in accordance with Table 2.
5) Heating of the device at 120° C. for 20 min.
6) Application of a Ba/Al cathode (3 nm+150 nm) by vapour deposition.
7) Encapsulation of the device.

Example 7

Measurements and Comparison of the Results

The OLEDs obtained in this way are characterised by standard methods. The following properties are measured: UIL characteristic, electroluminescence spectrum, colour coordinates, efficiency, operating voltage and lifetime. The results are summarised in Table 3, where OLED1 serves as comparison in accordance with the prior art. In Table 3, $U_{on}$ stands for the use voltage, U(100) stands for the voltage at 100 cd/m$^2$ and U(1000) stands for the voltage at 1000 cd/m$^2$.

TABLE 3

Measurement results with OLED1 to OLED4

| | Max. eff. [cd/A] | $U_{on}$ [V] | U(100) [V] | U(1000) [V] | CIE @ 100 cd/m$^2$ |
|---|---|---|---|---|---|
| OLED1 (comp.) | 8.15 | 3.85 | 6.60 | 8.80 | 0.33/0.62 |
| OLED2 | 31.79 | 2.64 | 4.06 | 5.80 | 0.34/0.62 |
| OLED3 | 32.34 | 2.61 | 3.99 | 5.70 | 0.34/0.62 |
| OLED4 | 35.12 | 2.57 | 3.91 | 5.65 | 0.34/0.62 |

As can be seen from Table 3, significantly improved phosphorescent OLEDs with respect to operating voltage and efficiency are obtained using matrix materials TMM2, TMM3 and TMM4 according to the invention. All OLEDs exhibit comparable colour coordinates. The high operating voltage and the low efficiency of OLED1 may be due to the low HOMO and high LUMO of matrix material TMM1.

The invention claimed is:

1. A compound of the formula (1),

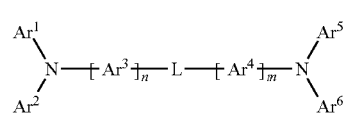

formula (1)

where the following applies to the symbols and indices used:

Ar$^1$ and Ar$^2$ is on each occurrence, identically or differently, an aromatic or heteroaromatic ring system having 5 to 60 aromatic ring atoms, which is optionally substituted by one or more radicals R; Ar$^1$ and Ar$^2$ here may also be connected to one another by a single bond and thus form a carbazole;

Ar$^3$ and Ar$^4$ is on each occurrence, identically or differently, a divalent aromatic or heteroaromatic ring system having 5 to 30 aromatic ring atoms, which is optionally substituted by one or more radicals R, with the proviso that Ar$^3$ and Ar$^4$ do not contain any aryl groups having more than two aromatic six-membered rings condensed directly onto one another;

$Ar^5$ is selected from a group of formulae (3), (4), or (6),

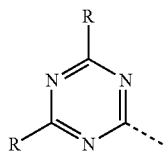
formula (3)

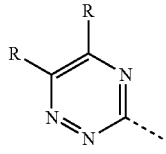
formula (4)

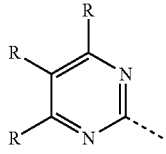
formula (6)

$Ar^6$ is selected from any one group of formulae (3) to (15),

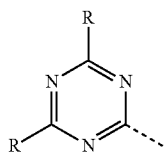
formula (3)

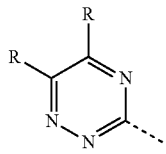
formula (4)

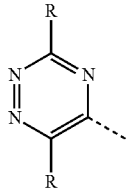
formula (5)

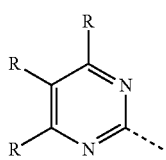
formula (6)

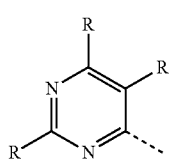
formula (7)

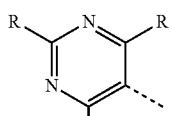
formula (8)

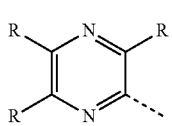
formula (9)

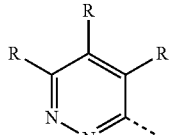
formula (10)

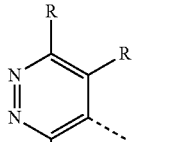
formula (11)

formula (12)

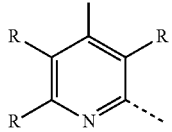
formula (12)

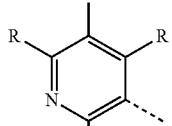
formula (13)

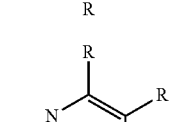
formula (14)

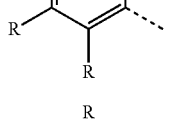
formula (15)

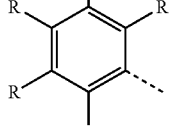

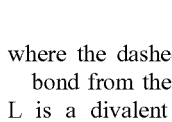

where the dashed bond indicates the position of the bond from the group to the nitrogen;

L is a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which is optionally substituted in each case by one or more radicals R, where one or more $CH_2$ groups, is optionally replaced by $Si(R)_2$, $Ge(R)_2$, $Sn(R)_2$, C=O, C=S, C=Se, C=NR, P(=O)R, S=O, $SO_2$, —O—, —S— or —CONR— and where one or more H atoms is optionally replaced by D, F, Cl, Br, I, CN or $NO_2$, or a divalent aromatic ring system having 5 to 30 aromatic ring atoms, which is optionally substituted by one or more radicals R, where L does not contain any aryl groups having more than two sequentially condensed aromatic six-membered rings, or L is $Si(R)_2$, $Ge(R)_2$, O, S, C(=O), S(=O), $SO_2$, $SF_4$, PR, P(=O)(R), $PF_3$, P(=S)(R), AsR, As(=O)(R), As(=S)(R), Sb, Sb(=O)(R), Sb(=S)(R), N(Ar) or L is a combination of two, three, four or five of these systems;

R is on each occurrence, identically or differently, a H, D, F, Cl, Br, I, CN, $NO_2$, $N(Ar)_2$, $N(R^1)_2$, C(=O)Ar, C(=O)$R^1$, P(=O)$(Ar)_2$, $B(R^1)_2$, $B(OR^1)_2$, $Si(R^1)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^1$, where one or more non-adjacent $CH_2$ groups is optionally replaced by $R^1C=CR^1$, C≡C, $Si(R^1)_2$, $Ge(R^1)_2$, $Sn(R^1)_2$, C=O, C=S, C=Se, C=$NR^1$, P(=O)$(R^1)$, SO, $SO_2$, $NR^1$, O, S or $CONR^1$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^1$, an aryloxy or heteroaryloxy group having 5 to 60 aromatic ring atoms, which is optionally substituted by one or more radicals $R^1$, or an aralkyl or heteroaralkyl group having 5 to 60 aromatic ring atoms, which may in each case be substituted by one or more radicals $R^1$, where two or more adjacent substituents R may optionally form a mono- or polycyclic, aliphatic, aromatic or heteroaromatic ring system, which is optionally substituted by one or more radicals $R^1$;

$R^1$ is on each occurrence, identically or differently, a H, D, F, Cl, Br, I, CN, $NO_2$, $N(Ar)_2$, $N(R^2)_2$, C(=O)Ar, C(=O)$R^2$, P(=O)$(Ar)_2$, $B(R^2)_2$, $B(OR^2)_2$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, C=$NR^2$, P(=O)$(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which is optionally substituted by one or more radicals $R^2$, where two or more adjacent substituents $R^1$ may optionally form a mono- or polycyclic, aliphatic, aromatic or heteroaromatic ring system, which is optionally substituted by one or more radicals $R^2$;

Ar is on each occurrence, identically or differently, an aromatic or heteroaromatic ring system having 5-30 aromatic ring atoms, which is optionally substituted by one or more non-aromatic radicals $R^2$; two radicals Ar which are bonded to the same N atom or P atom may also be bridged to one another by a single bond or a bridge selected from $N(R^2)$, $C(R^2)_2$, O or S;

$R^2$ is a H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^2$ may form a mono- or polycyclic, aliphatic, aromatic or heteroaromatic ring system with one another;

m and n are on each occurrence, identically or differently, 0 or 1, where m=n=1 if L stands for O, S or N(Ar).

2. The compound according to claim 1, wherein L is a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which is optionally substituted in each case by one or more radicals R, where one or more $CH_2$ groups, which are not adjacent, is optionally replaced by $Si(R)_2$, $Ge(R)_2$, $Sn(R)_2$, C=O, C=S, C=Se, C=NR, P(=O)R, S=O, $SO_2$, —O—, —S— or —CONR— and where one or more H atoms is optionally replaced by D, F, Cl, Br, I, CN or $NO_2$, or a divalent aromatic ring system having 5 to 30 aromatic ring atoms, which is optionally substituted by one or more radicals R, where L does not contain any aryl groups having more than two sequentially condensed aromatic six-membered rings, or L is $Si(R)_2$, $Ge(R)_2$, O, S, C(=O), S(=O), $SO_2$, $SF_4$, PR, P(=O)(R), $PF_3$, P(=S)(R), AsR, As(=O)(R), As(=S)(R), Sb, Sb(=O)(R), Sb(=S)(R), N(Ar) or L is a combination of two, three, four or five of these systems.

3. The compound according to claim 1, wherein $Ar^6$ is selected from formulae (12), (13), or (14).

4. The compound according to claim 1, wherein $Ar^6$ is selected from any one of formulae (3) to (11).

5. The compound according to claim 1, wherein the unit —$NAr^5Ar^6$ is selected from any one group of formulae (16) to (20), (22), (24), or (25);

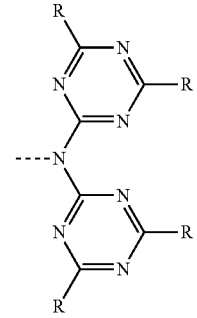

formula (16)

-continued

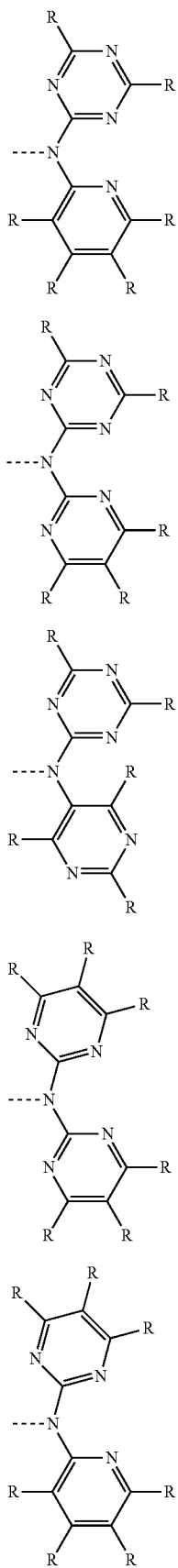

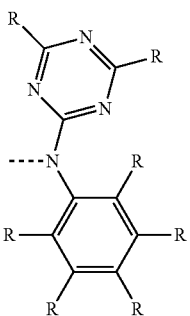
formula (17)

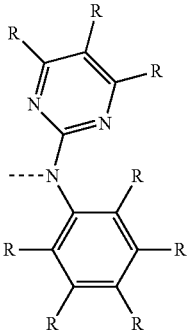
formula (18)

formula (19)

formula (20)

formula (22)

formula (24)

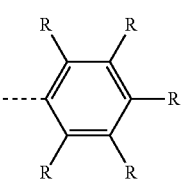
formula (25)

where the symbols used have the meanings given in claim 1, and the dashed bond indicates the bond from this group to L or Ar⁴.

6. The compound according to claim 1, wherein Ar¹ and Ar² stand, identically or differently on each occurrence, for an aromatic or heteroaromatic ring system having 5 to 30 aromatic ring atoms, which may in each case also be substituted by one or more radicals R.

7. The compound according to claim 1, wherein Ar¹ and Ar² stand, identically or differently on each occurrence, for an aromatic or heteroaromatic ring system having 5 to 24 aromatic ring atoms, which may in each case also be substituted by one or more radicals R.

8. The compound according to claim 1, wherein the groups Ar¹ and Ar² are selected, identically or differently on each occurrence, from the formulae (28) to (42),

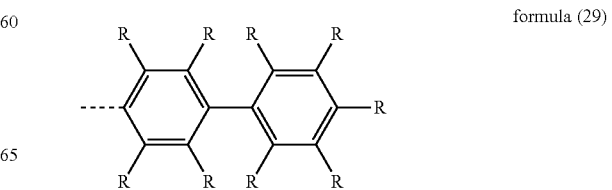
formula (28)

formula (29)

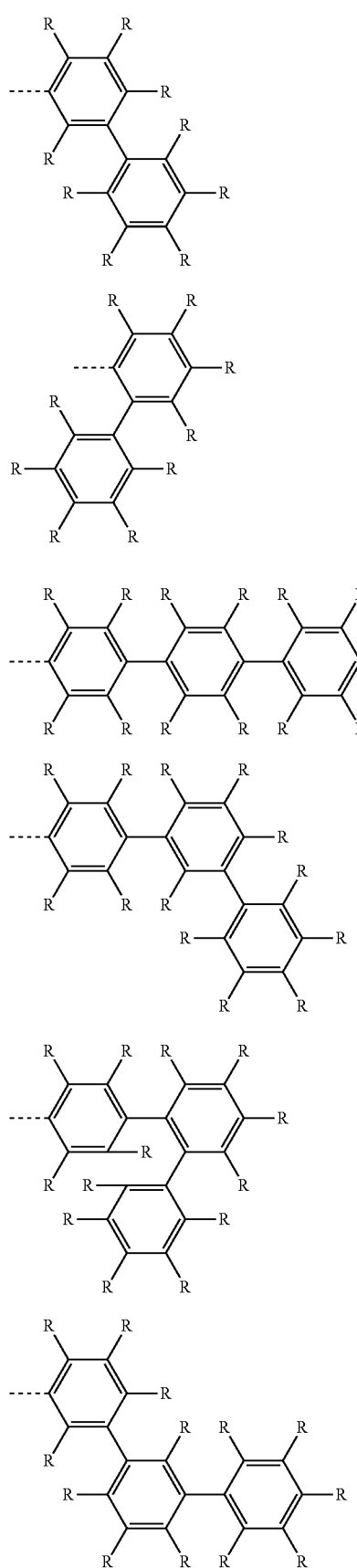
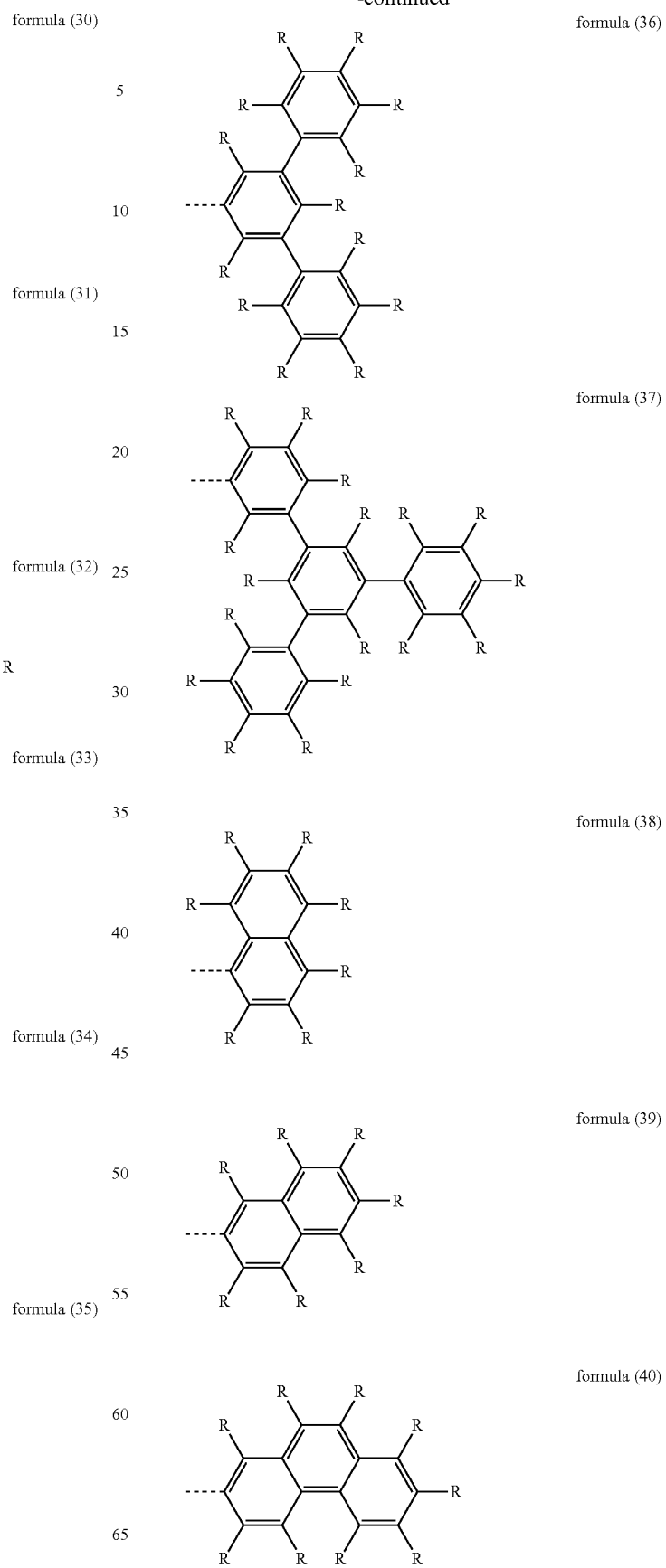

-continued

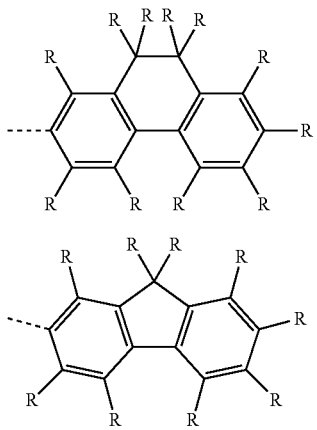

formula (41)

formula (42)

where the symbols used have the meanings given in claim 1, and the dashed bond indicates the bond from this group to the nitrogen.

9. The compound according to claim 1, wherein, if n=0 and/or m=0, L is a divalent straight-chain alkylene or alkylidene group having 1 to 5 C atoms, or a branched or cyclic alkylene or alkylidene group having 3 to 6 C atoms, which is optionally substituted by in each case one or more radicals R, where one or more $CH_2$ groups which are not bonded directly to N and are not adjacent is optionally replaced by $Si(R)_2$, C=O, P(=O)R, S=O, $SO_2$, —O—, —S— or —CONR— and where one or more H atoms is optionally replaced by D or F, or a divalent aromatic ring system having 5 to 24 aromatic ring atoms, which may also be substituted by one or more radicals R, or $Si(R)_2$, C(=O), S(=O), $SO_2$, P(=O)R or a combination of two or three of these systems; and in that, if m=n=1, L is selected from the above-mentioned embodiments or from O, S or N(Ar).

10. The compound according to claim 1, wherein m and n=1, and the bridging unit L has a structure of the formula (145):

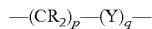   formula (145)

where R has the meaning given in claim 1, and furthermore:
Y is, identically or differently on each occurrence, $CR_2$, $SiR_2$, $GeR_2$, S, O or NR;
p is a number from 0 to 14;
q is 0, 1, 2, 3 or 4;
p+q>0; with the proviso that a plurality of heteroatoms are not bonded directly to one another.

11. The compound according to claim 1, wherein
p is 0, 1, 2, 3, 4, 5 or 6;
q is 0, 1 or 2.

12. A process for the preparation of a compound according to claim 1, comprising the reaction steps:
a) synthesising a compound G-$(Ar^3)_n$-L-$(Ar^4)_m$—$NAr^5Ar^6$ by reaction of a compound G-$(Ar^3)_n$-L-$(Ar^4)_m$—$NH_2$ with a compound G-$Ar^5$ and G-$Ar^6$, optionally with addition of a base and/or a catalyst, where G stands for a reactive leaving group, in particular fluorine, chlorine, bromine or iodine; and
b) introducing the group $Ar^1Ar^2N$— by coupling a group $Ar^1Ar^2NH$ to $Ar^3$ or L or by coupling a group $Ar^1Ar^2$—N—$Ar^3$-G to L.

13. An oligomer, polymer or dendrimer comprising one or more compounds according to claim 1, where one or more bonds are present from the compound according to the invention to the polymer, oligomer or dendrimer.

14. An electronic device comprising the compound according to claim 1.

15. The electronic device according to claim 14, selected from the group consisting of organic electroluminescent device (organic light-emitting diode, OLED), organic integrated circuit (O-IC), organic field-effect transistor (O-FET), organic thin-film transistor (O-TFT), organic light-emitting transistor (O-LET), organic solar cell (O-SC), organic dye-sensitised solar cell (ODSSC), organic optical detector, organic photoreceptor, organic field-quench device (O-FQD), light-emitting electrochemical cell (LEC), organic laser diode (O-laser) and organic plasmon emitting device.

16. An organic electroluminescent device comprising the compound according to claim 1 is used as a matrix material for fluorescent or phosphorescent emitters and/or in a hole-blocking layer and/or in an electron-transport layer and/or in an electron-blocking or exciton-blocking layer and/or in a hole-transport layer.

17. A solution, dispersion or mini emulsion comprising at least one compound according to claim 1 and at least one solvent.

18. A mixture comprising at least one compound according to claim 1 and at least one further compound.

19. A compound of the formula (1),

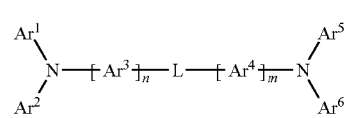

formula (1)

where the following applies to the symbols and indices used:

$Ar^1$ and $Ar^2$ are selected, identically or differently on each occurrence, from the formulae (28) to (42), and the dashed bond indicates the bond from this group to the nitrogen,

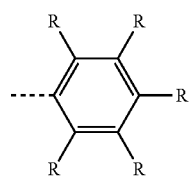

formula (28)

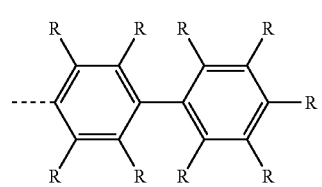

formula (29)

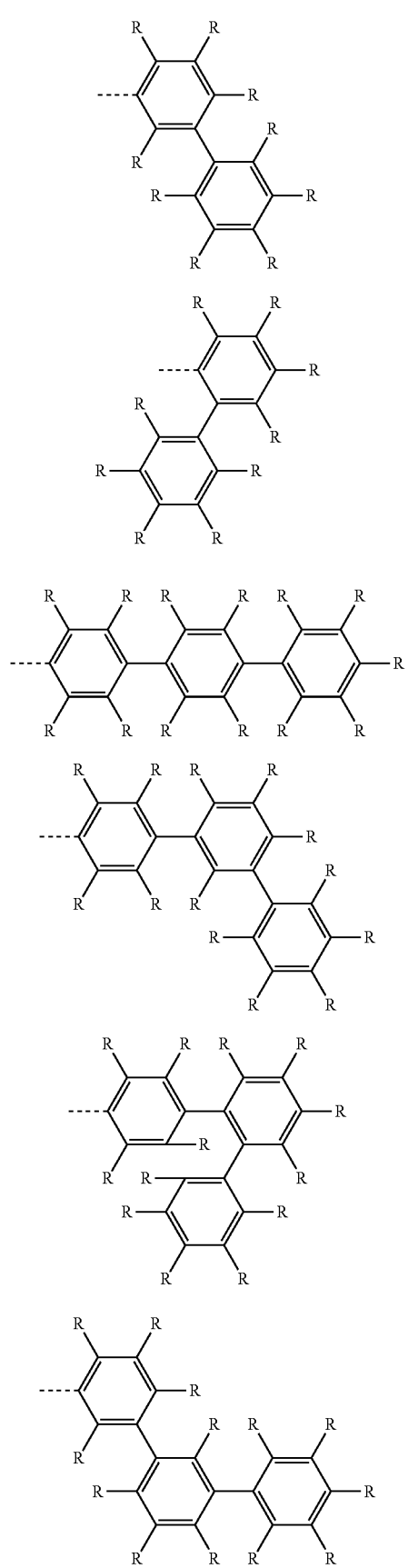
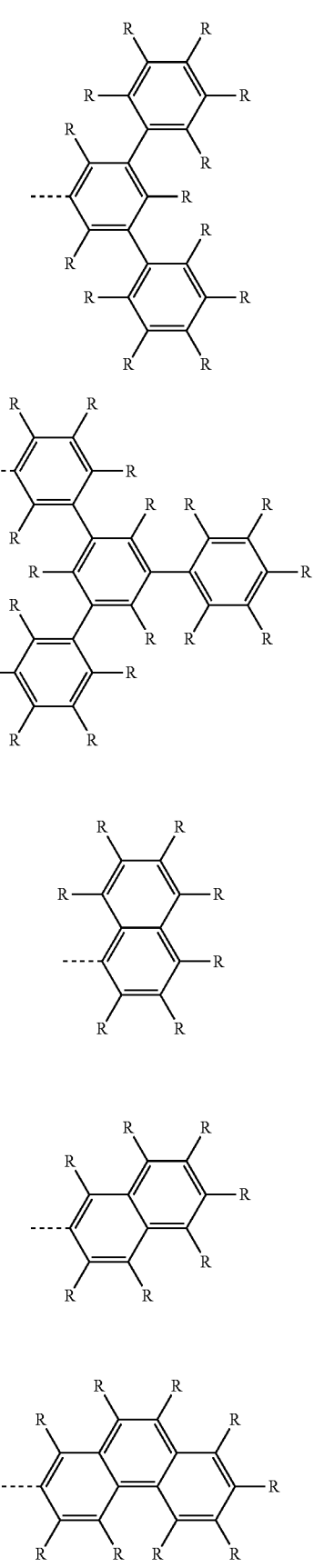
formula (30)
formula (31)
formula (32)
formula (33)
formula (34)
formula (35)
formula (36)
formula (37)
formula (38)
formula (39)
formula (40)

formula (41)
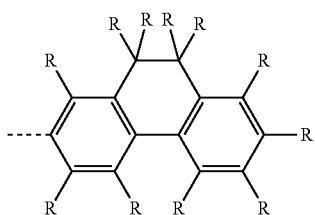

formula (42)
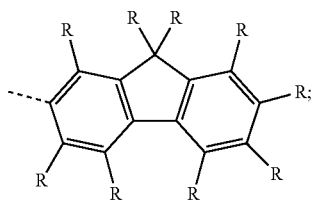

Ar³ and Ar⁴ is on each occurrence, identically or differently, a divalent aromatic or heteroaromatic ring system having 5 to 30 aromatic ring atoms, which is optionally substituted by one or more radicals R, with the proviso that Ar³ and Ar⁴ do not contain any aryl groups having more than two aromatic six-membered rings condensed directly onto one another;

Ar⁵ is selected from the formulae (3), (4) or (6)

formula (3)
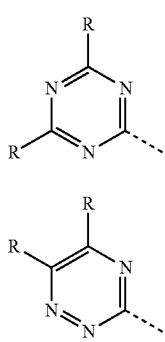

formula (4)
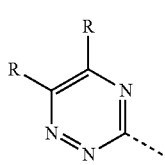

formula (6)
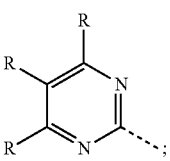

Ar⁶ is selected from the group consisting of formulae (3) to (11), the dashed bond here indicates the position of the bond from the group to the nitrogen formula (3)
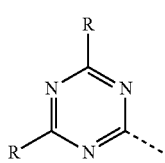

formula (4)
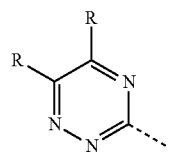

formula (5)
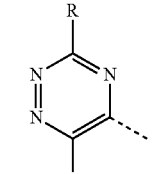

formula (6)
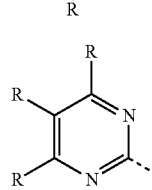

formula (7)
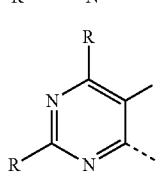

formula (8)
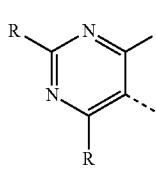

formula (9)
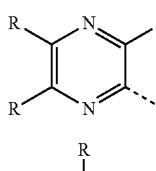

formula (10)
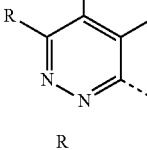

formula (11)
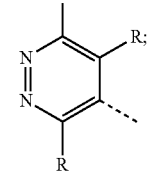

L is a divalent aromatic ring system having 5 to 30 aromatic ring atoms, which is optionally substituted by one or more radicals R, where L does not contain any aryl groups having more than two sequentially condensed aromatic six-membered rings;

R is on each occurrence, identically or differently, a H, D, F, Cl, Br, I, CN, NO₂, N(Ar)₂, N(R¹)₂, C(=O)Ar, C(=O)R¹, P(=O)(Ar)₂, B(R¹)₂, B(OR¹)₂, Si(R¹)₃, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^1$, where one or more non-adjacent $CH_2$ groups is optionally replaced by $R^1C=CR^1$, $C≡C$, $Si(R^1)_2$, $Ge(R^1)_2$, $Sn(R^1)_2$, $C=O$, $C=S$, $C=Se$, $C=NR^1$, $P(=O)(R^1)$, $SO$, $SO_2$, $NR^1$, $O$, $S$ or $CONR^1$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^1$, an aryloxy or heteroaryloxy group having 5 to 60 aromatic ring atoms, which is optionally substituted by one or more radicals $R^1$, or an aralkyl or heteroaralkyl group having 5 to 60 aromatic ring atoms, which may in each case be substituted by one or more radicals $R^1$, where two or more adjacent substituents R may optionally form a mono- or polycyclic, aliphatic, aromatic or heteroaromatic ring system, which is optionally substituted by one or more radicals $R^1$;

$R^1$ is on each occurrence, identically or differently, a H, D, F, Cl, Br, I, CN, $NO_2$, $N(Ar)_2$, $N(R^2)_2$, $C(=O)Ar$, $C(=O)R^2$, $P(=O)(Ar)_2$, $B(R^2)_2$, $B(OR^2)_2$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, $SO$, $SO_2$, $NR^2$, $O$, $S$ or $CONR^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which is optionally substituted by one or more radicals $R^2$, where two or more adjacent substituents $R^1$ may optionally form a mono- or polycyclic, aliphatic, aromatic or heteroaromatic ring system, which is optionally substituted by one or more radicals $R^2$;

Ar is on each occurrence, identically or differently, an aromatic or heteroaromatic ring system having 5-30 aromatic ring atoms, which is optionally substituted by one or more non-aromatic radicals $R^2$; two radicals Ar which are bonded to the same N atom or P atom may also be bridged to one another by a single bond or a bridge selected from $N(R^2)$, $C(R^2)_2$, O or S;

$R^2$ is a H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^2$ may form a mono- or polycyclic, aliphatic, aromatic or heteroaromatic ring system with one another;

m and n are on each occurrence, identically or differently, 0 or 1, where m=n=1 if L stands for O, S or N(Ar).

20. The compound according to claim 19, wherein L is selected from one of formula (51) to formula (136)

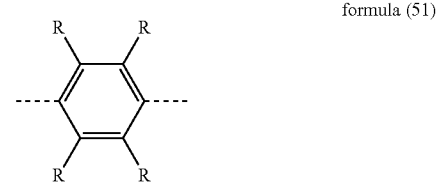

formula (51)

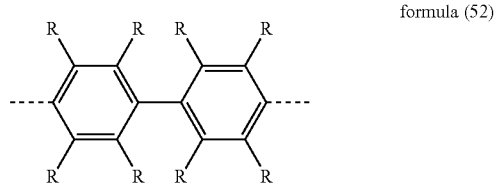

formula (52)

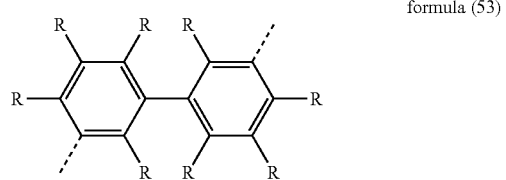

formula (53)

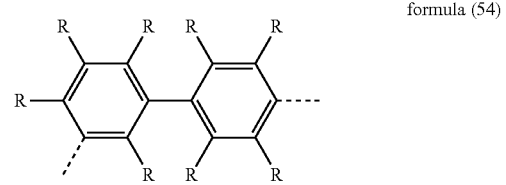

formula (54)

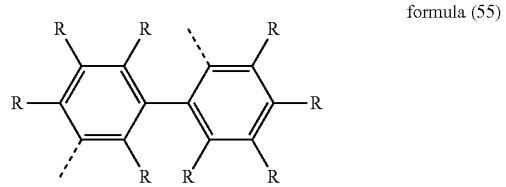

formula (55)

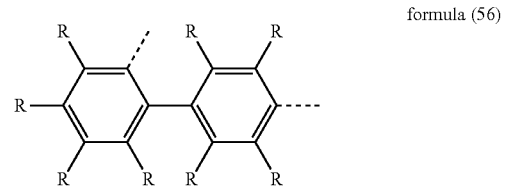

formula (56)

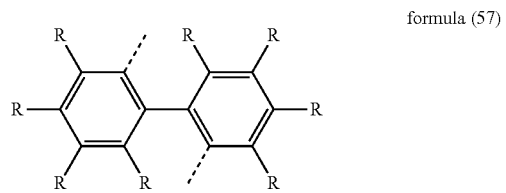

formula (57)

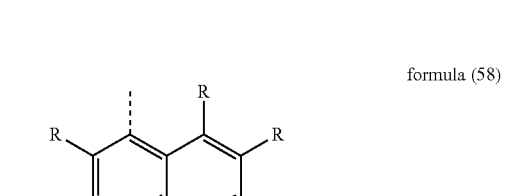

formula (58)

-continued
formula (59)
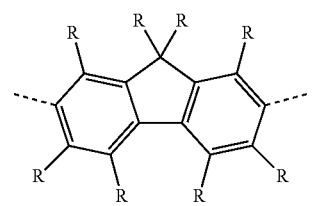
formula (60)
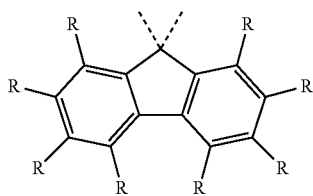
formula (61)
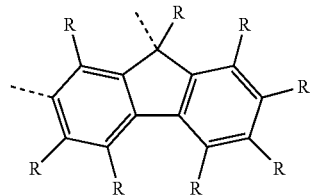
formula (62)
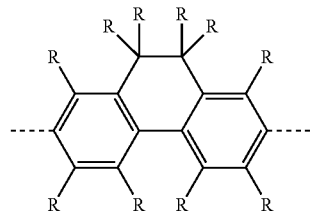
formula (63)
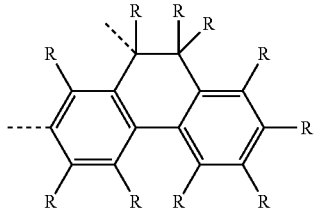
formula (64)
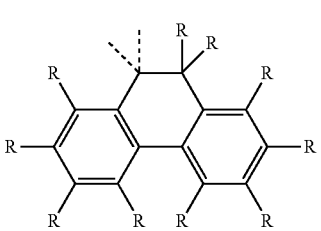
formula (65)
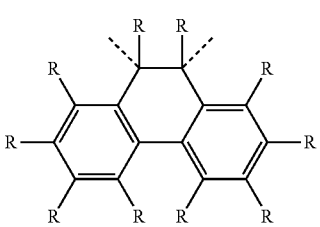
-continued
formula (66)
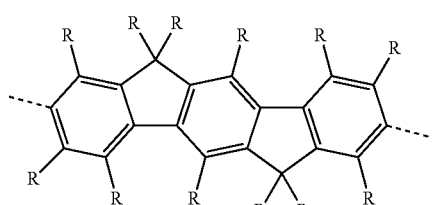
formula (67)
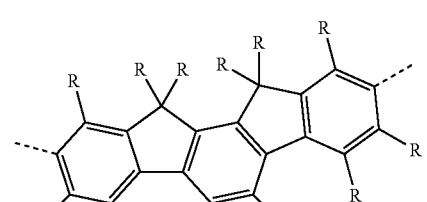
formula (68)
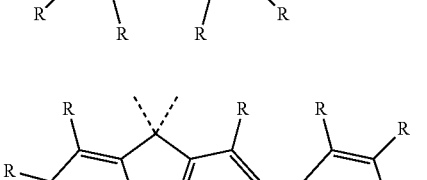
formula (69)
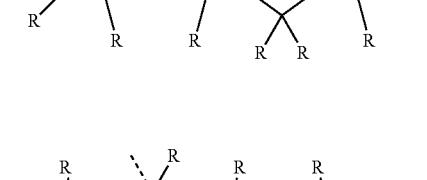
formula (70)
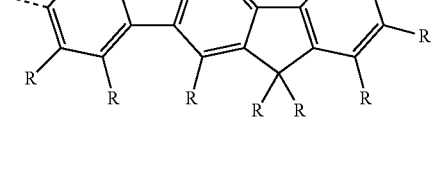
formula (71)
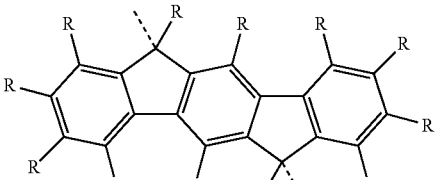

-continued
formula (72)
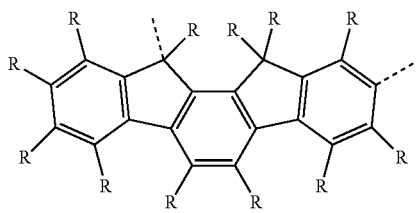
formula (73)
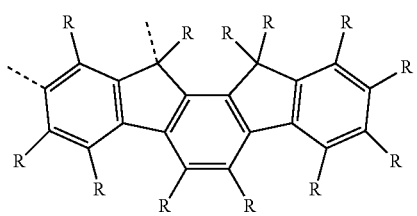
formula (74)
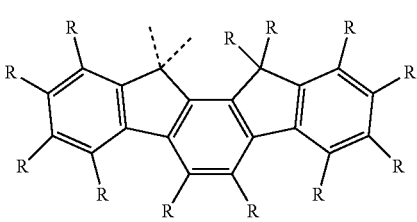
formula (75)
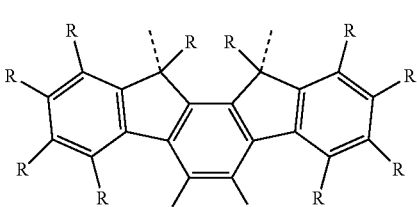
formula (76)
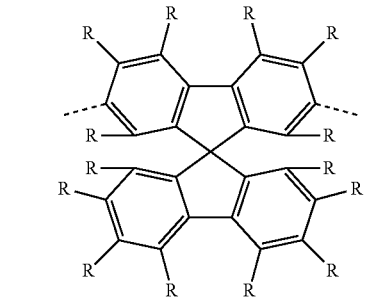
formula (77)
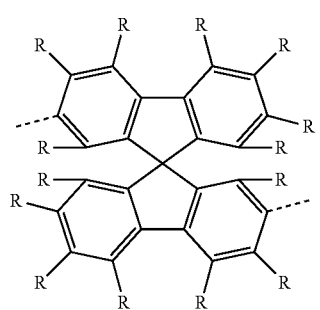
-continued
formula (78)
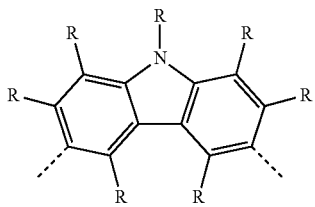
formula (79)
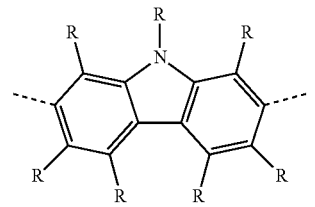
formula (80)
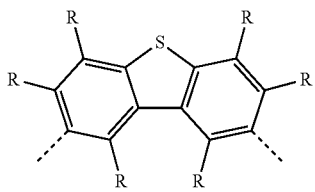
formula (81)
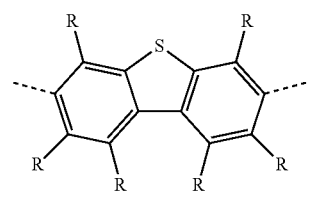
formula (82)
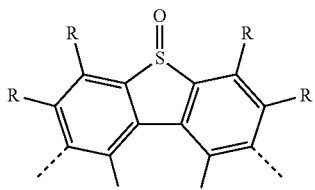
formula (83)
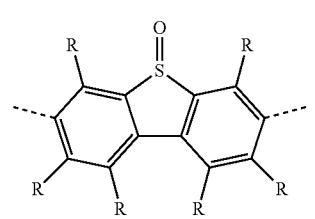
formula (84)
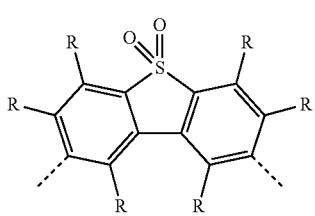

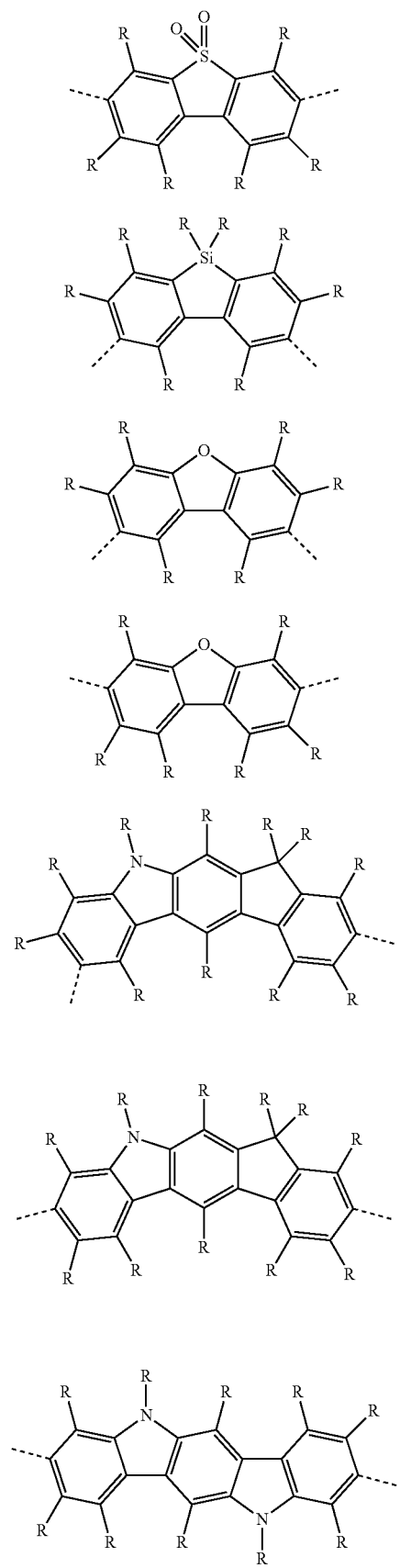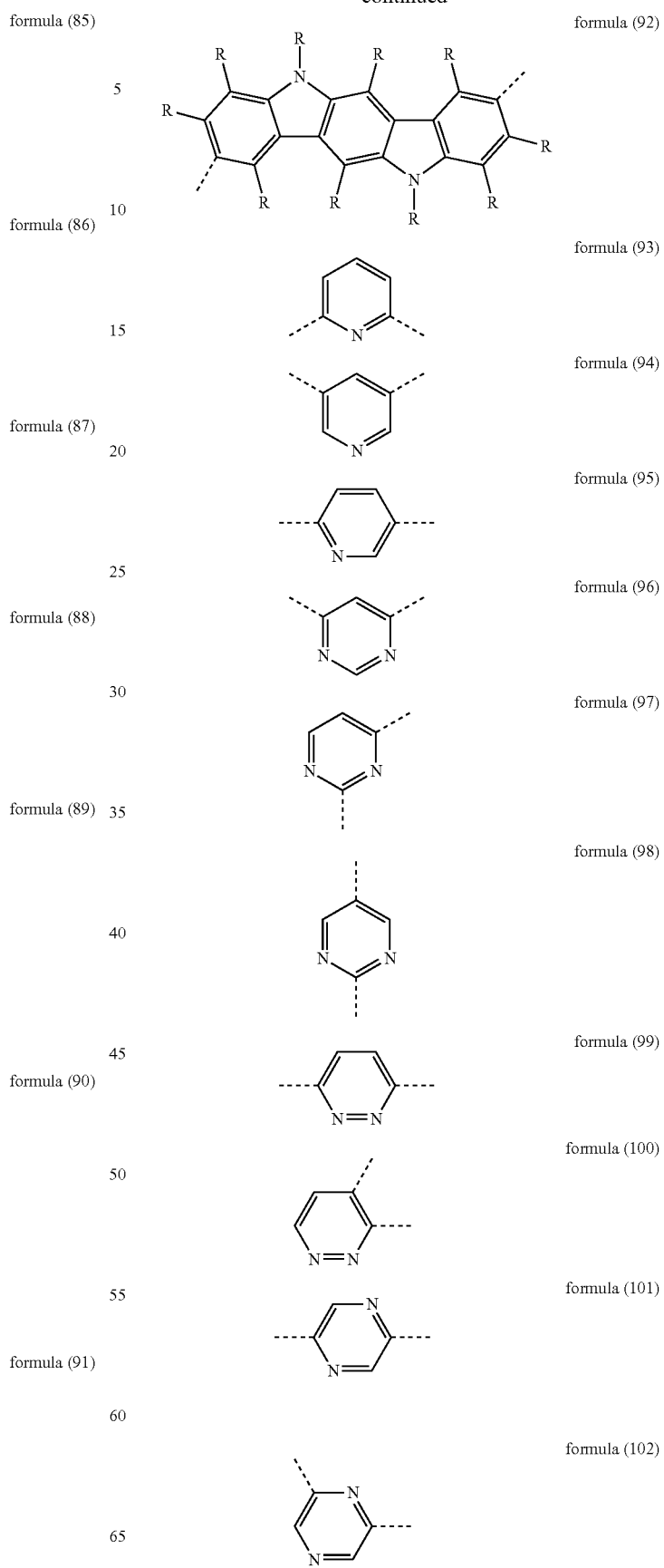

formula (103)
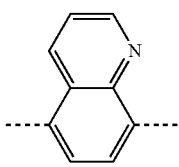
formula (104)
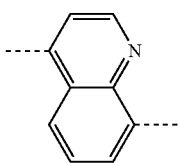
formula (105)
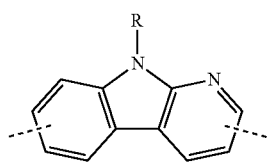
formula (106)
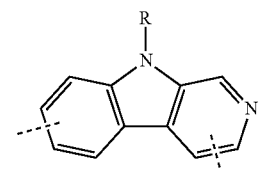
formula (107)
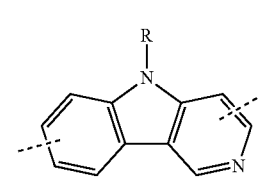
formula (108)
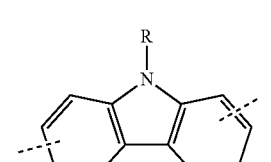
formula (109)
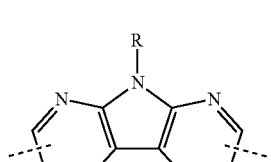
formula (110)
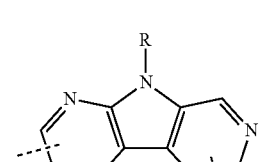
formula (111)
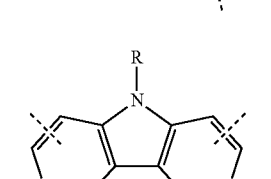
formula (112)
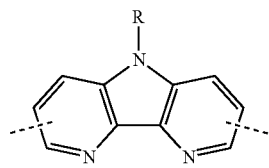
formula (113)
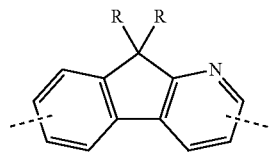
formula (114)
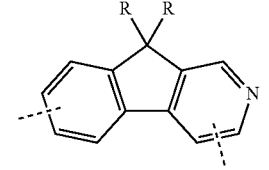
formula (115)
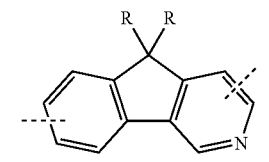
formula (116)
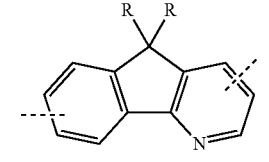
formula (117)
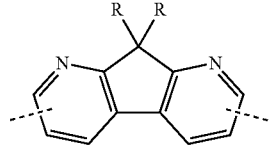
formula (118)
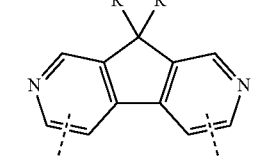
formula (119)
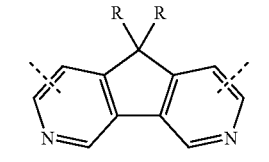
formula (120)
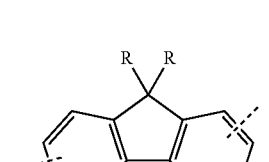

-continued

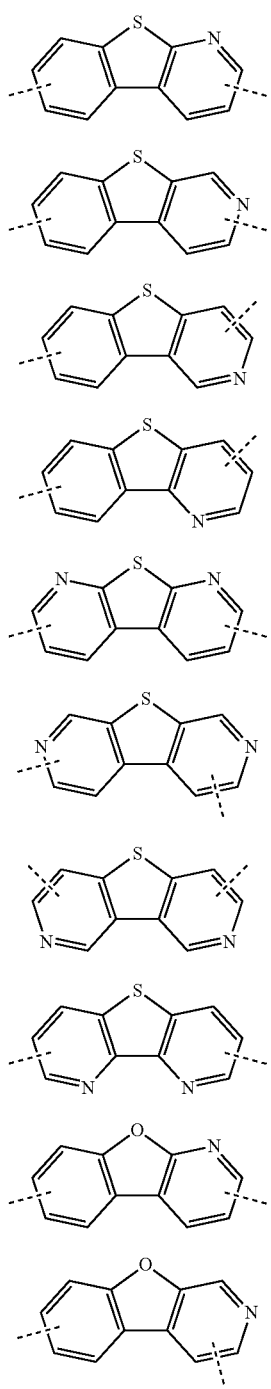

formula (121)
formula (122)
formula (123)
formula (124)
formula (125)
formula (126)
formula (127)
formula (128)
formula (129)
formula (130)

-continued

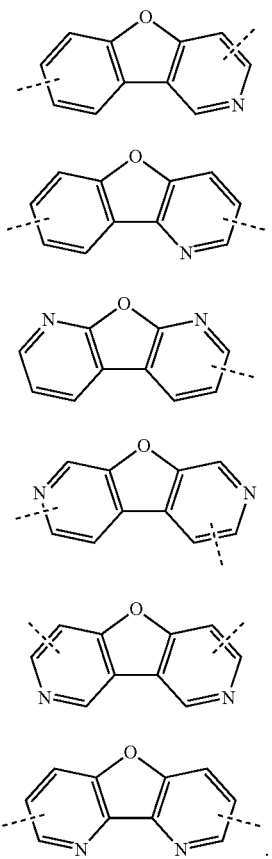

formula (131)
formula (132)
formula (133)
formula (134)
formula (135)
formula (136)

21. The compound according to claim 1, wherein, if n=0 and/or m=0, L is a divalent straight-chain alkylene or alkylidene group having 1 to 10 C atoms or a branched or cyclic alkylene or alkylidene group having 3 to 10 C atoms, which is optionally substituted by in each case one or more radicals R, where one or more $CH_2$ groups which are not bonded directly to N and are not adjacent is optionally replaced by $Si(R)_2$, C=O, P(=O)R, S=O, $SO_2$, —O—, —S— or —CONR— and where one or more H atoms is optionally replaced by D or F, or a divalent aromatic ring system having 5 to 24 aromatic ring atoms, which may also be substituted by one or more radicals R, or $Si(R)_2$, C(=O), S(=O), $SO_2$, P(=O)R or a combination of two or three of these systems; and in that, if m=n=1, L is selected from the above-mentioned embodiments or from O, S or N(Ar).

* * * * *